United States Patent
Shigaki et al.

(10) Patent No.: US 8,022,294 B2
(45) Date of Patent: Sep. 20, 2011

(54) DYE-SENSITIZED PHOTOELECTRIC CONVERSION DEVICE

(75) Inventors: Koichiro Shigaki, Kita-ku (JP); Masayoshi Kaneko, Kita-ku (JP); Akira Maenosono, Kita-ku (JP); Takayuki Hoshi, Kita-ku (JP); Teruhisa Inoue, Kita-ku (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 741 days.

(21) Appl. No.: 11/922,062

(22) PCT Filed: Jun. 13, 2006

(86) PCT No.: PCT/JP2006/311867
§ 371 (c)(1), (2), (4) Date: Dec. 12, 2007

(87) PCT Pub. No.: WO2006/134939
PCT Pub. Date: Dec. 21, 2006

(65) Prior Publication Data
US 2009/0165858 A1 Jul. 2, 2009

(30) Foreign Application Priority Data
Jun. 14, 2005 (JP) .................. 2005-173429
Jun. 17, 2005 (JP) .................. 2005-177087

(51) Int. Cl.
*H01L 31/0216* (2006.01)

(52) U.S. Cl. ........ 136/263; 136/256; 136/250; 429/111; 257/431

(58) Field of Classification Search .................. 136/263, 136/256, 250; 429/111; 257/431
See application file for complete search history.

(56) References Cited

U.S. PATENT DOCUMENTS

| | | | |
|---|---|---|---|
| 2,803,640 | A | 8/1957 | Heckert |
| 4,927,721 | A | 5/1990 | Gratzel et al. |
| 5,084,365 | A | 1/1992 | Gratzel et al. |
| 5,670,091 | A | 9/1997 | Marder et al. |
| 6,084,176 | A | 7/2000 | Shiratsuchi et al. |
| 6,291,763 | B1 | 9/2001 | Nakamura |
| 6,335,481 | B1 | 1/2002 | Watanabe |
| 6,376,765 | B1 | 4/2002 | Wariishi et al. |
| 7,141,735 | B2 * | 11/2006 | Ikeda et al. ............ 136/263 |
| 7,728,222 | B2 | 6/2010 | Ikeda et al. |
| 7,851,701 | B2 | 12/2010 | Ikeda et al. |
| 7,977,570 | B2 | 7/2011 | Shigaki et al. |
| 2002/0010969 | A1 | 1/2002 | Goettel et al. |
| 2003/0152827 | A1 | 8/2003 | Ikeda et al. |
| 2004/0074532 | A1 | 4/2004 | Ikeda et al. |
| 2004/0099306 | A1 | 5/2004 | Hara et al. |
| 2004/0187918 | A1 | 9/2004 | Ikeda et al. |
| 2006/0130249 | A1 * | 6/2006 | Ikeda et al. ............ 8/550 |
| 2007/0191455 | A1 | 8/2007 | Hiyoshi et al. |
| 2008/0067476 | A1 | 3/2008 | Shigaki et al. |
| 2008/0087327 | A1 | 4/2008 | Horiuchi et al. |

FOREIGN PATENT DOCUMENTS

| | | |
|---|---|---|
| CN | 1861740 | 11/2006 |
| EP | 0 566 077 A2 | 10/1993 |
| EP | 0 566 081 A2 | 10/1993 |
| EP | 0 566 082 A1 | 10/1993 |
| EP | 0 692 800 A2 | 1/1996 |
| EP | 0 892 411 A2 | 1/1999 |
| EP | 0 911 841 A2 | 4/1999 |
| EP | 0 924 724 A2 | 6/1999 |
| EP | 1 075 005 A2 | 2/2001 |
| EP | 1 311 001 A1 | 5/2003 |
| EP | 1 339 129 A | 8/2003 |

(Continued)

OTHER PUBLICATIONS

Nature, vol. 353, p. 737 (1991); B. O'Regan and M. Gratzel; "A low-cost, high-efficiency solar cell based on dye-sensitized colloidal TiO2 films".
J.Am.Chem.Soc. 1993, vol. 115, p. 6382 (1993); M.K. Nazeeruddin et al.; "Conversion of Light to Electricity by cis-X2Bis(2,2'-bipyridyl-4,4'-dicarboxylate)ruthenium(II) Charge-Transfer Sensitizers (X=Cl-,Br-, I-, CN-, and SCN-) on Nanocrystalline TiO2 Electrodes".
Chemistry Letters, p. 1241 91998); Wataru Kubo et al.; "Fabrication of Quasi-solid-state Dye-sensitized TiO2 Solar Cells Using Low Molecular Weight Gelators".
International Search Report dated Dec, 20, 2005 in co-pending U.S. Appl. No. 11/661,843.

(Continued)

*Primary Examiner* — Ling Choi
(74) *Attorney, Agent, or Firm* — Nields, Lemack & Frame, LLC

(57) ABSTRACT

The present invention relates to a photoelectric conversion device sensitized by supporting a methine based dye represented by the following formula (1):

[KA 1]

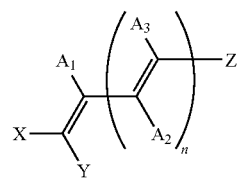

(1)

(in the above formula, n represents an integer of 0 to 7; X and Y each represent a hydrogen atom, an optionally substituted aromatic residue, an optionally substituted aliphatic hydrocarbon residue and the like. In addition, X and Y may combine together to form an optionally substituted ring. $A_1$, $A_2$ and $A_3$ represent each independently an optionally substituted aromatic residue, an optionally substituted aliphatic hydrocarbon residue and the like. In addition, when n is other than 0, a plural number of $A_1$ and/or $A_2$ and/or $A_3$ may form an optionally substituted ring. The benzene ring "a" may have substituent selected from a halogen atom, an amide group, a hydroxyl group, a cyano group and the like);
on a thin film of oxide semiconductor fine particles provided on a substrate, and has features that the device can be manufactured at low cost and has high conversion efficiency.

12 Claims, No Drawings

FOREIGN PATENT DOCUMENTS

| | | |
|---|---|---|
| EP | 1 422 782 A1 | 5/2004 |
| EP | 1 628 356 A1 | 2/2006 |
| JP | 48-3115 B1 | 1/1973 |
| JP | 8-81222 A | 3/1996 |
| JP | 2664194 B2 | 6/1997 |
| JP | 11-67285 A | 3/1999 |
| JP | 11-158395 | 6/1999 |
| JP | 11-163378 | 6/1999 |
| JP | 11-176489 | 7/1999 |
| JP | 11-214731 A | 8/1999 |
| JP | 2000-26487 A | 1/2000 |
| JP | 2000-195569 | 7/2000 |
| JP | 2000-223167 | 8/2000 |
| JP | 2000-268892 A | 9/2000 |
| JP | 2000-285977 | 10/2000 |
| JP | 2000-285978 | 10/2000 |
| JP | 2001-042524 | 2/2001 |
| JP | 2001-52766 A | 2/2001 |
| JP | 2001-0645529 | 3/2001 |
| JP | 2002-164089 A | 6/2002 |
| JP | 2003-59547 | 2/2003 |
| JP | 2004-22222 | 1/2004 |
| JP | 2004-146421 A | 5/2004 |
| JP | 2004-207224 A | 7/2004 |
| JP | 2004-227825 | 8/2004 |
| JP | 2005-5026 | 1/2005 |
| JP | 2005-11800 | 1/2005 |
| JP | 2005-19251 A | 1/2005 |
| JP | 2005-123013 * | 5/2005 |
| JP | 2005-129329 A | 5/2005 |
| JP | 2005-129429 A | 5/2005 |
| JP | 2005-129430 A | 5/2005 |
| JP | 2005-209682 | 8/2005 |
| JP | 2005-227376 A | 8/2005 |
| JP | 2006-93284 A | 4/2006 |
| JP | 2006-156212 | 6/2006 |
| JP | 2006-188582 A | 7/2006 |
| JP | 2006-190534 A | 7/2006 |
| WO | 02/11213 A1 | 2/2002 |
| WO | WO 02/11213 A1 * | 2/2002 |
| WO | 2004/011555 A1 | 2/2004 |
| WO | 2004/082061 A1 | 9/2004 |
| WO | WO 2004/082061 A1 * | 9/2004 |
| WO | 2005/077956 A1 | 8/2005 |
| WO | 2006/028087 A1 | 3/2006 |

OTHER PUBLICATIONS

Solar Energy Materials & Solar Cells 80 (2003) 47-71; K.Sayama et al.; "Efficient sensitization of nanocrystalline TiO2 films with cyanine and merocyanine organic dyes".
Supplemental European Search Report dated May 25, 2009 in co-pending foreign application (EP05782209).
Office Action dated Jun. 21, 2010 in co-pending U.S. Appl. No. 11/661,843.
International Search Report dated Sep. 5, 2006 in co-pending U.S. Appl. No. 11/920,899.
Office Action dated Jun. 21, 2010 in co-pending U.S. Appl. No. 11/920,899.
J. Mater. Chem., 2000, 10, 1-25; Yasuhiko Shirota; "Organic materials for electronic and optoelectronic devices".
J. Am. Chem. Soc. 2006, 128, p. 16701-16707; Sanghoon Kim et al.; "Molecular Engineering of Organic Sensitizers for Solar Cell Applications".
Thin Solid Films 438-439 (2003) p. 147-152; Keiichi Miyairi et al.; "Photovoltaic properties of double layer devices consisting of titanium dioxide and porphyrin dispersed hole transporting material layer".
Chem. Commun., 2004, p. 68-69; Sanghoon Kim et al.; "The role of borole in a fully conjugated electron-rich system".
International Search Report dated Sep. 17, 2002 in a co-pending foreing application.
International Search Report dated May 25, 2004 in a co-pending foreing application.
Supplementary European Search Report dated Feb. 13, 2006 in a co-pending foreign application.
Supplementary European Search Report dated Feb. 21, 2007 in a co-pending foreign application.
International Search Report dated May 22, 2007 in a co-pending foreign application.
European communication dated Jun. 7, 2010 in a co-pending foreign application.
Office Actions dated Sep. 17, 2009 and May 25, 2010 in co-pending U.S. Appl. No. 11/10/548,858.
Office Action dated May 7, 2010 in co-pending U.S. Appl. No. 12/224,350.
Final Rejection in co-pending U.S. Appl. No. 12/224,350, filed Aug. 25, 2008.
International Search Report dated Jun. 4, 2002 in co-pending U.S. Appl. No. 10/482,425, filed Dec. 29, 2003, now US Patent 7,851,701.
European communication dated Aug. 4, 2010 in corresponding foreign application (EP06757302.2).
Office Action dated Oct. 8, 2010 in co-pending U.S. Appl. No. 11/920,899.
Office Action dated Oct. 7, 2010 in co-pending U.S. Appl. No. 11/661,843.
Notice of Allowance dated Mar. 16, 2011 in co-pending U.S. Appl. No. 11/920,899.
Final Rejection dated Mar. 16, 2011 in co-pending U.S. Appl. No. 11/661,843.
Notice of Allowance dated Jun. 22, 2011 in co-pending U.S. Appl. No. 11/661,843.

* cited by examiner

DYE-SENSITIZED PHOTOELECTRIC CONVERSION DEVICE

TECHNICAL FIELD

The present invention relates to a photoelectric conversion device sensitized with an organic dye and a solar battery, and more specifically, a photoelectric conversion device characterized by using oxide semiconductor fine particles sensitized with a methine based dye having a specific skeletal structure and a solar battery utilizing the same.

BACKGROUND ART

As an energy resource replaceable to fossil fuels such as oil, coal, etc., solar battery utilizing the solar light has been attracting attention. Currently, concerning silicon solar battery using crystalline or amorphous silicon, or compound semiconductor solar battery or the like, using gallium, arsenic, etc., development and study such as high-efficiency improvement are actively promoted. However, there is a problem that versatile use of these batteries is difficult due to too high energy and cost required for manufacturing. In addition, photoelectric conversion device using dye-sensitized semiconductor particles or solar battery using the same has been known, and materials and manufacturing technology to produce this has been disclosed (see Patent Literature 1, Non-Patent Literature 1 and Non-Patent Literature 2). This photoelectric conversion device is manufactured using an oxide semiconductor such as titanium oxide, etc., which is comparatively low in cost, as a raw material, and attracts attention because of a possibility that a photoelectric conversion device having lower cost compared with that of conventional solar battery using silicon, etc. can be obtained, and also that a colorful solar battery can be obtained, and the like. However, since a ruthenium based complex is used as a sensitizing dye to obtain a device having high conversion efficiency, cost of the dye itself is high and its supply problems remain. In addition, use of an organic dye as a sensitizing dye has been already tried, but its practical use has not been realized at present due to low conversion efficiency, stability and endurance, etc., and further improvement in conversion efficiency is desired (see Patent Literature 2). In addition, until now, a case of manufacturing photoelectric conversion device using a methine based dye has been disclosed, and comparatively large number of study cases on coumarin based dyes (see Patent Literature 3) and merocyanine based dyes have been disclosed (see Patent Literatures 4, 5, 6 and 7), but further cost reduction and improvements in stability and conversion efficiency were desired.

Patent Literature 1: JP No. 2664194;
Patent Literature 2: WO No. 2002011213;
Patent Literature 3: JP-A-2002-164089;
Patent Literature 4: JP-A-08-81222;
Patent Literature 5: JP-A-11-214731;
Patent Literature 6: JP-A-2001-52766;
Patent Literature 7: JP-A-2003-59547;
Non-Patent Literature 1: B. O'Regan and M. Graetzel, Nature, V 353, 737 (1991);
Non-Patent Literature 2: M. K. Nazeeruddin, A. Kay, I. Rodicio, R. Humphry-Baker, E. Muller, P. Liska, N. Vlachopoulos, M. Graetzel, J. Am. Chem. Soc., V 115, 6382 (1993);
Non-Patent Literature 3: W. Kubo, K. Murakoshi, T. Kitamura, K. Hanabusa, H. Shirai, and S. Yanagida, Chem. Lett., 1241 (1998);

DISCLOSURE OF INVENTION

Problem to be Solved by the Invention

In the photoelectric conversion device using a semiconductor sensitized with an organic dye, development of a photoelectric conversion device using an organic dye of low cost and having high stability, conversion efficiency and practicability, has been demanded.

Means for Solving the Problem

The inventors of the present invention have, after studying intensively a way to solve the above problem, found that a photoelectric conversion device having high stability and conversion efficiency can be obtained by manufacturing a photoelectric conversion device using semiconductor particles, which are sensitized with a specified methine based dye, and thereby accomplished the present invention.

Namely, the present invention relates to the following aspects:

(1) a photoelectric conversion device characterized by using oxide semiconductor fine particles sensitized with a methine based dye represented by the following formula (1):

[KA1]

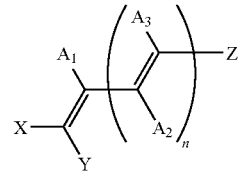

(1)

(in the formula (1), n represents an integer of 0 to 7; X and Y represent each independently a hydrogen atom, an optionally substituted aromatic residue, an optionally substituted aliphatic hydrocarbon residue, a carboxyl group, a phosphoric acid group, a sulfonic acid group, a cyano group, an optionally substituted alkylsulfonyl group having 1 to 5 carbon atoms, an acyl group, an optionally substituted amide group or an alkoxycarbonyl group; in addition, X and Y may combine together to form an optionally substituted ring (provided that when Z represents a group represented by the following formula (3), pyrazolone ring is excluded); $A_1$, $A_2$ and $A_3$ represent each independently a hydrogen atom, an optionally substituted aromatic residue, an optionally substituted aliphatic hydrocarbon residue, a hydroxyl group, a phosphoric acid group, a cyano group, a halogen atom, a carboxyl group, a carbonamide group, an optionally substituted alkoxy group, an aryloxy group, an alkoxycarbonyl group, an arylcarbonyl group, or an acyl group; in addition, when n is 2 or more and each of $A_2$ and $A_3$ exists plurally, each of $A_2$ and $A_3$ may be same or different from each other; in addition, when n is other than 0, a plural number of $A_1$ and/or $A_2$ and/or $A_3$ may form an optionally substituted ring; Z represents a group represented by the following formula (2) or (3)):

[KA 2]

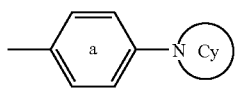

(2)

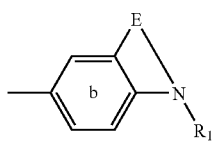

(3)

[KA 3]

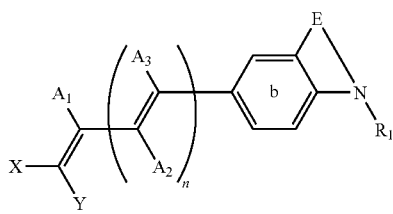

(1a)

(the benzene ring "a" in the formula (2) may optionally have, besides the substituent described in the formula (2), 1 to 4 substituents selected from the group consisting of a halogen atom, an amide group, a hydroxyl group, a cyano group, a nitro group, an optionally substituted alkoxy group, an acyl group, a substituted or unsubstituted amino group, an optionally substituted aliphatic hydrocarbon residue and an optionally substituted aromatic residue; in addition, when a plural number of substituents exist, these substituents may combine together to form an optionally substituted ring; in addition, said substituents on the benzene ring "a" may combine together with said $A_1$ and/or $A_2$ and/or $A_3$ to form an optionally substituted ring;

the ring Cy in the formula (2) is 4- to 7-membered ring, and may contain a carbon atom and a hetero atom other than the nitrogen atom described in the formula (2) as a ring member atom; in addition, the ring Cy may have a substituent, and when the ring Cy has a plural number of substituents, arbitrary substituents thereof may combine together to form further a ring; the benzene ring "b" in the formula (3) may have, besides the substituent described in the formula (3), 1 to 3 substituents selected from the group consisting of a halogen atom, an optionally substituted amide group, a hydroxyl group, a cyano group, a nitro group, an optionally substituted alkoxy group, an acyl group, a substituted or unsubstituted amino group, an optionally substituted aliphatic hydrocarbon residue and an optionally substituted aromatic residue; in addition, when a plural number of substituents exist, these substituents may combine together to form an optionally substituted ring; in addition, said substituent on the benzene ring "b" may combine together with any one of the above-described $A_1$, $A_2$ and $A_3$ to form an optionally substituted ring; E in the formula (3) represents an optionally substituted saturated or unsaturated hydrocarbon residue having 2 to 4 carbon atoms; when E has a plural number of substituents, arbitrary substituents thereof may combine together to form a ring; $R_1$ represents an optionally substituted aromatic residue, an optionally substituted aliphatic hydrocarbon residue or an acyl group);

(2) a photoelectric conversion device characterized by using oxide semiconductor fine particles sensitized with a methine based dye represented by the following formula (1a):

(in the formula (1a), n represents an integer of 0 to 7; $R_1$ represents an optionally substituted aromatic residue, an optionally substituted aliphatic hydrocarbon residue or an acyl group; E represents an optionally substituted saturated or unsaturated hydrocarbon residue containing 2 to 4 carbon atoms; when E has a plural number of substituents, arbitrary substituents thereof may combine together to form a ring; Y and X represent each independently a hydrogen atom, an optionally substituted aromatic residue, an optionally substituted aliphatic hydrocarbon residue, a carboxyl group, a phosphoric acid group, a sulfonic acid group, a cyano group, an amide group, an optionally substituted alkylsulfonyl group having 1 to 5 carbon atoms or an alkoxycarbonyl group; $A_1$, $A_2$ and $A_3$ represent each independently an optionally substituted aromatic residue, an optionally substituted aliphatic hydrocarbon residue, a hydroxyl group, a phosphoric acid group, a cyano group, a hydrogen atom, a halogen atom, a carboxyl group, a carbonamide group, an alkoxycarbonyl group, an arylcarbonyl group or an acyl group; in addition, when n is 2 or more and each of $A_2$ and $A_3$ exists plurally, each of $A_2$ and each of $A_3$ may be same or different from each other; in addition, when n is other than 0, a plural number of $A_1$ and/or $A_2$ and/or $A_3$ may form an optionally substituted ring, and further they may form an optionally substituted ring together with the benzene ring "a"; the benzene ring "a" may have 1 to 3 substituents selected from the group consisting of a halogen atom, an amide group, a hydroxyl group, a cyano group, a nitro group, an alkoxyl group, an acyl group, a substituted or unsubstituted amino group, an optionally substituted aliphatic hydrocarbon residue and an optionally substituted aromatic residue; in addition, when a plural number of substituents exist, these substituents may combine each other, or together with $A_1$ and/or $A_2$ and/or $A_3$ similarly as described above to form an optionally substituted ring; and further, when E has a substituent, the substituent of E may combine together with the substituent on the benzene ring "a" to form an optionally substituted ring);

(3) the photoelectric conversion device according to (1) or (2), wherein the methine based dye represented by the formula (1a) according to the above (2) is a methine based dye represented by the following formula (2a):

[KA4]

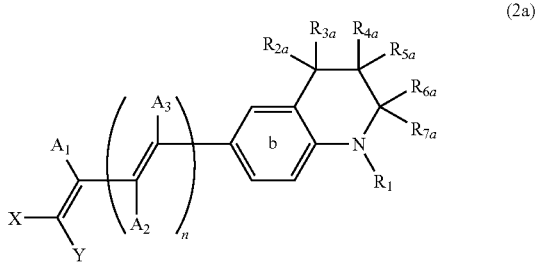

(2a)

(in the formula (2a), n, $R_1$, Y, X, $A_1$, $A_2$, $A_3$ and benzene ring "b" are each same as in the formula (1a); $R_{2a}$ to $R_{7a}$ represent a hydrogen atom, an optionally substituted aromatic residue, an optionally substituted aliphatic hydrocarbon residue or a halogen atom; in addition, $R_{2a}$ to $R_{7a}$ may combine together to form an optionally substituted ring);

(4) the photoelectric conversion device according to the above (3), wherein the methine based dye represented by the formula (2a) according to the above (3) is a methine based dye represented by the following formula (3a):

[KA 5]

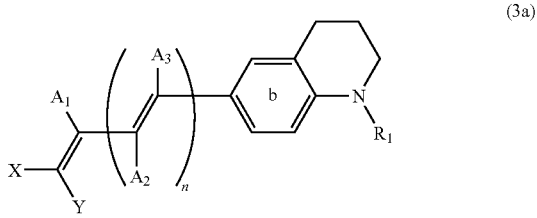

(3a)

(in the above formula, n, $R_1$, Y, X, $A_1$, $A_2$, $A_3$ and benzene ring "b" are each same as in the formula (1a));

(5) the photoelectric conversion device according to any one of the above (2) to (4), wherein X is a carboxyl group;

(6) the photoelectric conversion device according to any one of the above (1) to (5), wherein Y is a cyano group, a carboxyl group or an acyl group;

(7) the photoelectric conversion device according to any one of the above (1) to (6), wherein n is 0 to 6;

(8) the photoelectric conversion device according to any one of the above (1) to (7), wherein $R_1$ is an optionally substituted aliphatic hydrocarbon residue;

(9) the photoelectric conversion device according to the above (8), wherein the optionally substituted aliphatic hydrocarbon residue is an optionally substituted aliphatic hydrocarbon residue having 5 to 36 carbon atoms;

(10) the photoelectric conversion device according to any one of the above (1) to (9), wherein $R_1$ is an optionally substituted aromatic hydrocarbon residue;

(11) the photoelectric conversion device according to the above (10), wherein the optionally substituted aromatic hydrocarbon residue is an aromatic hydrocarbon residue having a substituent of an optionally substituted aliphatic hydrocarbon residue having 1 to 36 carbon atoms;

(12) a photoelectric conversion device characterized by using oxide semiconductor fine particles sensitized with one or more types of the methine based dye represented by the formula (1a) according to the above (2) and a metal complex and/or an organic dye having a structure other than the formula (1a);

(13) the photoelectric conversion device according to any one of the above (1) to (12), wherein the oxide semiconductor fine particles are those containing titanium dioxide, zinc oxide or tin oxide;

(14) the photoelectric conversion device according to any one of the above (2) to (13), wherein the oxide semiconductor fine particles are those sensitized by supporting a methine based dye represented by the formula (1a) according to the above (2) in the presence of an inclusion compound;

(15) the photoelectric conversion device according to any one of the above (1) to (14), wherein the oxide semiconductor fine particles are those sensitized by supporting a methine based dye on a thin film of oxide semiconductor fine particles;

(16) a solar battery characterized by using the photoelectric conversion device according to any one of the above (1) to (14);

(17) a methine based dye represented by the formula (1a) according to the above (2);

(18) the methine based dye according to the above (17), wherein the methine based dye represented by the formula (1a) according to the above (2) is a methine based dye represented by the formula (2a) according to the above (3);

(19) the methine based dye according to the above (18), wherein the methine based dye represented by the formula (2a) according to the above (3) is a methine based dye represented by the formula (3a) according to the above (4);

(20) a photoelectric conversion device, wherein the methine based dye represented by the formula (1a) according to the above (2) is supported on a semiconductor thin film of an oxide semiconductor thin film electrode;

(21) the photoelectric conversion device according to the above (1), wherein in the formula (1) according to the above (1), X is a carboxyl group; Y is a cyano group, a carboxyl group or an acyl group; Z is a group represented by the formula (3) and said group of formula (3) is a N—$R_1$-substituted tetrahydroquinoline-6-yl group or a N—$R_1$-substituted carbazol-3-yl group ($R_1$ is same as in the formula (3));

(22) the photoelectric conversion device according to the above (1), wherein in the formula (1) according to the above (1), X is a carboxyl group; Y is a cyano group; Z is a group represented by the formula (3): and said group of formula (3) is a N—$R_1$-substituted tetrahydroquinoline-6-yl group or a N—$R_1$-substituted carbazol-3-yl group ($R_1$ is same as in the formula (3));

(23) the photoelectric conversion device according to the above (22), wherein Y is a cyano group; and $R_1$ is an optionally substituted, saturated or unsaturated, linear or branched alkyl group having 1 to 18 carbon atoms;

(24) a methine based dye represented by the following formula:

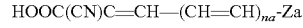

(in the formula, Za is an N—$(C_1$-$C_{18})$alkyl-substituted tetrahydroquinoline-6-yl group or an N—$(C_1$-$C_{18})$alkyl-substituted carbazol-3-yl group, and na represents an integer of 0 to 3);

(25) a photoelectric conversion device comprising supporting a methine based dye represented by the following formula (1b):

[KA6]

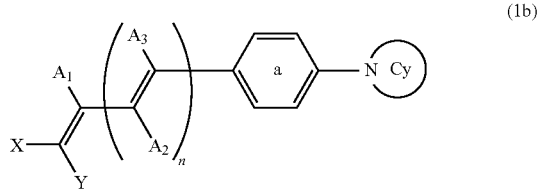

(1b)

(in the formula (1b), n represents an integer of 0 to 7; X and Y represent each independently a hydrogen atom, an optionally substituted aromatic residue, an optionally substituted aliphatic hydrocarbon residue, a carboxyl group, a phosphoric acid group, a sulfonic acid group, a cyano group, an acyl group, an amide group or an alkoxycarbonyl group; in addition, X and Y may combine together to form an optionally substituted ring; $A_1$, $A_2$ and $A_3$ represent each independently an optionally substituted aromatic residue, an optionally substituted aliphatic hydrocarbon residue, a hydroxyl group, a phosphoric acid group, a cyano group, a hydrogen atom, a halogen atom, a carboxyl group, a carbonamide group, an alkoxycarbonyl group, an arylcarbonyl group or an acyl group; in addition, when n is 2 or more and each of $A_2$ and $A_3$ exists plurally, each of $A_2$ and each of $A_3$ may be same or different from each other; in addition, when n is other than 0, a plural number of $A_1$ and/or $A_2$ and/or $A_3$ may form an optionally substituted ring, and further form an optionally substituted ring together with the benzene ring "a"; the benzene ring "a" may have 1 to 4 substituents selected from the group consisting of a halogen atom, an amide group, a hydroxyl group, a cyano group, a nitro group, an alkoxyl group, an acyl group, a substituted or unsubstituted amino group, an optionally substituted aliphatic hydrocarbon residue and an optionally substituted aromatic residue; in addition, when a plural number of substituents exist, these substituents combine each other or together with $A_1$ and/or $A_2$ and/or $A_3$ as described above to form an optionally substituted ring; the ring Cy is a 4- to 7-membered ring, may contain a carbon atom and a hetero atom other than the nitrogen atom described in the formula (1b) as a ring member atom, and may have substituent; when Cy has a plural number of substituents, arbitrary substituents thereof may further form a ring); on a thin film of oxide semiconductor fine particles provided on a substrate;

(26) a photoelectric conversion device comprising supporting a methine based dye represented by the following formula (2b):

[KA7]

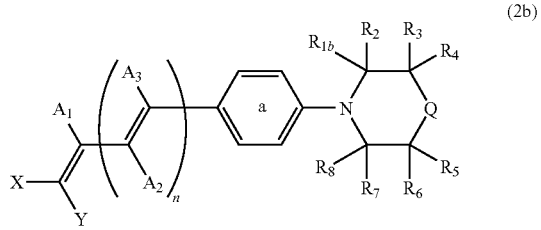

(2b)

(in the formula (2b), n, X, Y, $A_1$, $A_2$, $A_3$ and benzene ring "a" are each same as in the above formula (1b); $R_{1b}$ to $R_{8b}$ represent each independently a hydrogen atom, an optionally substituted aliphatic hydrocarbon residue, an optionally substituted aromatic hydrocarbon residue, a halogen atom or a hydroxyl group; in addition, each of $R_{1b}$ to $R_{4b}$ and $R_{5b}$ to $R_{8b}$ may combine together to form an optionally substituted ring; Q represents $CR_9R_{10}$, $NR_{11}$, an oxygen atom, a sulfur atom, a selenium atom or $SO_2$; $R_9$ to $R_{11}$ represent each independently a hydrogen atom, an optionally substituted aliphatic hydrocarbon residue or an optionally substituted aromatic hydrocarbon residue); on a thin film of oxide semiconductor fine particles provided on a substrate;

(27) the photoelectric conversion device according to the above (26), wherein X is a carboxyl group;

(28) the photoelectric conversion device according to the above (27), wherein Y in the formula (1b) according to the above (25) is a cyano group, a carboxyl group or an acyl group;

(29) the photoelectric conversion device according to the above (25), wherein X is a carboxyl group, Y is a cyano group, a carboxyl group or an acyl group, and n is 0 to 4;

(30) the photoelectric conversion device according to the above (26), wherein X is a carboxyl group, Y is a cyano group, a carboxyl group or an acyl group, n is 0 to 4, and Q is an oxygen atom;

(31) a photoelectric conversion device comprising supporting one or more types of methine based dyes represented by the formula (1b) according to the above (25), a metal complex and/or an organic dye having a structure other than the formula (1b) on a thin film of oxide semiconductor fine particles (hereinafter, referred to as an oxide semiconductor thin film) provided on a substrate;

(32) the photoelectric conversion device according to any one of the above (25) to (31), wherein the oxide semiconductor thin film contains titanium dioxide, zinc oxide or tin oxide;

(33) the photoelectric conversion device according to any one of the above (25) to (31), wherein the oxide semiconductor fine particles sensitized by a methine based dye is the one in which a methine based dye represented by the formula (1b) according to the above (25) is supported on the oxide semiconductor fine particles in the presence of an inclusion compound;

(34) a solar battery characterized by using a photoelectric conversion device according to any one of the above (25) to (33);

(35) the photoelectric conversion device according to the above (1), wherein in the formula (1) according to the above (1), X is a carboxyl group, Y is a cyano group, a carboxyl group or an acyl group, or X and Y combine together and X(Y)C= is a 2-phenyl-5-carboxy-3-pyrazolone-4-yl group, Z is a group represented by the formula (2) and said group of the formula (2) is a morpholinophenyl group, and n is 0;

(36) a methine based dye represented by the following formula:

X(Y)C=CH-Zb (in the formula, X represents a carboxyl group, Y represents a cyano group, a carboxyl group or an acyl group, or X and Y combine together and X(Y)C= is a 2-phenyl-5-carboxy-3-pyrazolone-4-yl group, and Zb represents a morpholinophenyl group).

EFFECT OF THE INVENTION

By using a specified methine based dye, a solar battery having high conversion efficiency and stability could be provided. In addition, by using oxide semiconductor fine particles sensitized with 2 or more types of dyes in combination, an improvement of conversion efficiency was found.

BEST MODE FOR CARRYING OUT THE INVENTION

Hereinafter, the present invention will be explained in detail.

The photoelectric conversion device of the present invention uses oxide semiconductor fine particles sensitized with a methine based dye represented by the aforementioned formula (1). Namely, the photoelectric conversion device of the present invention is the one in which the methine based dye represented by the above formula (1) is supported on a thin film of oxide semiconductor fine particles (hereinafter, also simply referred to as an oxide semiconductor thin film) provided on a substrate.

In the aforementioned formula (1), when Z is represented by the formula (3), the methine based dye is represented by the following formula (1a):

[KA8]

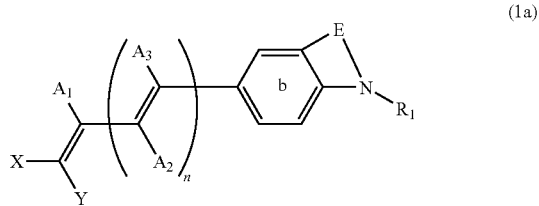

(1a)

In the formula, n represents an integer of 0 to 7, preferably 0 to 6, and particularly preferably 0 to 4;

$R_1$ in the formula (1a) represents an optionally substituted aromatic residue, an optionally substituted aliphatic hydrocarbon residue or an acyl group, and is preferably an optionally substituted aromatic residue or an optionally substituted aliphatic hydrocarbon residue.

In the above, the aromatic group in "an optionally substituted aromatic residue" means a group of aromatic ring from which one hydrogen atom is excluded, and the aromatic group includes, for example, aromatic hydrocarbon ring such as benzene, naphthalene, anthracene, phenanthrene, pyrene, perylene, terrylene, etc.; heterocyclic aromatic ring such as indene, azulene, pyridine, pyrazine, pyrimidine, pyrazol, pyrazolidine, thiazolidine, oxazolidine, pyran, chromene, pyrrol, pyrrolidine, benzimidazole, imidazoline, imidazolidine, imidazole, pyrazole, triazole, triazine, diazole, indoline, thiophene, thienothiophene, furan, oxazole, oxadiazole, thiazine, thiazole, indole, benzothiazole, benzothiadiazole, naphthothiazole, benzoxazole, naphthoxazole, indolenine, benzoindolenine, quinoline, quinazoline, etc.; condensed type aromatic ring such as fluororene, carbazole, etc.; and the like, and is preferably an aromatic residue containing an aromatic ring (an aromatic ring or a condensed ring including aromatic rings) having 5 to 6 carbon atoms.

In the above, the aliphatic hydrocarbon residue in "an optionally substituted aliphatic hydrocarbon residue" includes an optionally substituted, saturated or unsaturated, linear or branched alkyl group and a cyclic alkyl group, and is preferably an optionally substituted, saturated or unsaturated, linear or branched alkyl group having 1 to 36 carbon atoms, and further preferably an optionally substituted, saturated or unsaturated, linear or branched alkyl group having 1 to 18 carbon atoms. In addition, an optionally substituted cyclic alkyl group includes, for example, a cycloalkyl having 3 to 8 carbon atoms, etc. Those specific examples include methyl group, ethyl group, n-propyl group, iso-propyl group, n-butyl group, iso-butyl group, ter-butyl group, octyl group, octadecyl group, isopropyl group, cyclohexyl group, vinyl group, propenyl group, pentenyl group, butenyl group, hexenyl group, hexadienyl group, isopropenyl group, isohexenyl group, cyclohexenyl group, cyclopentadienyl group, ethynyl group, propynyl group, pentynyl group, hexynyl group, isohexynyl group, cyclohexynyl group, etc.

In the above, the acyl group includes, for example, alkylcarbonyl group or arylcarbonyl group having 1 to 10 carbon atoms, etc., and is preferably alkylcarbonyl group having 1 to 4 carbon atoms. The specific example includes acetyl group, trifluoromethylcarbonyl group, pentafluoroethylcarbonyl group, propionyl group, etc.

The substituent in "an optionally substituted aromatic residue" and the substituent in "an optionally substituted aliphatic hydrocarbon residue" are not particularly limited, but include a sulfonic acid group, a sulfamoyl group, a cyano group, a isocyano group, a thiocyanate group, an isothiocyanato group, a nitro group, a nitrosyl group, a halogen atom, a hydroxyl group, a phosphoric acid group, a phosphate ester group, a substituted or unsubstituted amino group, an optionally substituted mercapto group, an optionally substituted amide group, an optionally substituted alkoxy group, an optionally substituted aryloxy group, a carboxyl group, a carbamoyl group, an acyl group, an aldehyde group, a substituted carbonyl group such as an alkoxycarbonyl group, an optionally substituted aromatic residue, an optionally substituted aliphatic hydrocarbon residue, etc.

Here, the halogen atom includes an atom of fluorine, chlorine, bromine, iodine, etc.; the phosphate ester group includes a ($C_1$-$C_4$)alkyl phosphate ester, etc.; the substituted or unsubstituted amino group includes an amino group, an alkyl-substituted amino group such as mono- or di-methylamino group, mono- or di-ethylamino group, mono- or di-propylamino group, etc., an aromatic substituted amino group such as mono- or di-phenylamino group, mono- or di-naphthylamino group, etc., an amino group substituted by one alkyl group and one aromatic hydrocarbon residue each, such as monoalkylmonophenylamino group, etc. or a benzylamino group, further an acetylamino group, a phenylacetylamino group, or the like; the optionally substituted mercapto group includes a mercapto group, an alkylmercapto group, a phenylmercapto group, etc; the optionally substituted amide group includes an amide group, an alkylamide group, an arylamide group, etc., respectively. Here, the alkoxy group means a group comprising bonding of the aforementioned aliphatic hydrocarbon residue and an oxygen atom, and includes, for example, methoxy group, ethoxy group, butoxy group, tert-butoxy group, etc., and in addition, the optionally substituted aryloxy group includes phenoxy group, naphthoxy group, etc., and these groups may have the same substituent as described in the section of "an optionally substituted aromatic residue". In addition, the acyl group includes, for example, an alkylcarbonyl group or an arylcarbonyl group having 1 to 10 carbon atoms, preferably an alkylcarbonyl group having 1 to 4 carbon atoms, and specifically includes acetyl group, trifluoromethylcarbonyl group, pentafluoroethylcarbonyl group, propionyl group, etc. In addition, the alkoxycarbonyl group includes, for example, an alkoxycarbonyl group having 1 to 10 carbon atoms, etc.

In addition, the substituent in "an optionally substituted aromatic residue" includes, besides the aforementioned substituents, an optionally substituted aliphatic hydrocarbon residue as an example of preferable substituent. The optionally substituted aliphatic hydrocarbon residue includes an optionally substituted aliphatic hydrocarbon residue having 1 to 36 carbon atoms as a preferable example. Here, the substituent includes the aforementioned substituents as the substituent in "an optionally substituted aliphatic hydrocarbon residue".

E represents an optionally substituted, saturated or unsaturated hydrocarbon group having 2 to 4 carbon atoms. When E has a plural number of substituents, these substituents may combine together to form a ring. E is preferably an optionally substituted, saturated or unsaturated hydrocarbon group particularly having 2 to 3 carbon atoms, and more preferably an optionally substituted, saturated or unsaturated hydrocarbon group having 3 carbon atoms. The ring formed by the substituents on E is preferably 5- to 10-membered ring, and particularly preferably the ring includes cyclopentane, cyclohexane, benzene, naphthalene, etc. As the aforementioned formula (3) containing E, preferable one includes an N—$R_1$-substituted tetrahydropyridyl group and an N—$R_1$-substituted tetrahydropyridyl group in which the tetrahydro atom(s) are substituted, etc. A plural number of tetrahydro atoms thereof may be substituted, and said substituents may form a ring. In addition, another preferable example includes an N—$R_1$-substituted carbazole-3-yl group, etc. In these cases, $R_1$ includes a ($C_1$-$C_{36}$) aliphatic hydrocarbon residue, and preferably an alkyl group or a substituted phenyl group (the substituent is a ($C_1$-$C_{36}$) aliphatic hydrocarbon residue, preferably an alkyl group). The ($C_1$-$C_{36}$) aliphatic hydrocarbon residue in $R_1$ is preferably a ($C_1$-$C_{18}$) alkyl group. In the case of N—$R_1$-substituted tetrahydropyridyl group, $R_1$ is further preferably a ($C_5$-$C_{18}$) alkyl group. $R_1$ in N—$R_1$-substituted carbazole-3-yl group is preferably a ($C_1$-$C_{18}$) alkyl group, and also in certain instances, preferably an around ($C_1$-$C_6$) alkyl group.

Y represents a hydrogen atom, an optionally substituted aromatic residue, an optionally substituted aliphatic hydrocarbon residue, a carboxyl group, a phosphoric acid group, a sulfonic acid group, a cyano group, an optionally substituted amide group and an optionally substituted alkylsulfonyl group or alkoxycarbonyl group having 1 to 5 carbon atoms, and is preferably a carboxyl group, a phosphoric acid group, a sulfonic acid group, a cyano group, an optionally substituted amide group and an optionally substituted alkylsulfonyl group or alkoxycarbonyl group having 1 to 5 carbon atoms, and is particularly preferably a cyano group. The optionally substituted alkylsulfonyl group having 1 to 5 carbon atoms is preferably trifluoromethylsulfonyl, pentafluoroethylsulfonyl, etc. The optionally substituted aromatic residue, the optionally substituted aliphatic hydrocarbon residue, the optionally substituted amide group and alkoxycarbonyl group are each same to those described for the substituent in "an optionally substituted aromatic residue" and "an optionally substituted aliphatic hydrocarbon residue".

X represents a hydrogen atom, an optionally substituted aromatic residue, an optionally substituted aliphatic hydrocarbon residue, a carboxyl group, a phosphoric acid group, a sulfonic acid group, a cyano group, an optionally substituted amide group and an optionally substituted alkylsulfonyl group or alkoxycarbonyl group having 1 to 5 carbon atoms, and is preferably a carboxyl group, a phosphoric acid group, a sulfonic acid group, and is particularly preferably a carboxyl group. The substituent in the optionally substituted aromatic residue, the optionally substituted aliphatic hydrocarbon residue, the optionally substituted amide group and alkoxycarbonyl group are each same to those described for the substituent in "an optionally substituted aromatic residue" and "an optionally substituted aliphatic hydrocarbon residue".

$A_1$, $A_2$ and $A_3$ represent each independently an optionally substituted aromatic residue, an optionally substituted aliphatic hydrocarbon residue, a hydroxyl group, a phosphoric acid group, a cyano group, a hydrogen atom, a halogen atom, a carboxyl group, a carbonamide group, an alkoxycarbonyl group, an arylcarbonyl group or an acyl group, and is preferably a hydrogen atom, an optionally substituted aromatic residue, an optionally substituted aliphatic hydrocarbon residue, a cyano group or a halogen atom, and is further preferably a hydrogen atom. The optionally substituted aromatic residue, the optionally substituted aliphatic hydrocarbon residue, the halogen atom, the alkoxycarbonyl group, the arylcarbonyl group and the acyl group are each same to those described for the substituent in "an optionally substituted aromatic residue" and "an optionally substituted aliphatic hydrocarbon residue". In addition, when n is 2 or more and $A_2$ and $A_3$ exist plurally, each of $A_2$ and each of $A_3$ may be same or different from each other.

In addition, when n is other than 0, a plural number of $A_1$ and/or $A_2$ and/or $A_3$ may form an optionally substituted ring, and further combine together with benzene ring "b" to form an optionally substituted ring. Example of a ring to be formed includes an unsaturated hydrocarbon ring or a heterocyclic ring.

More specifically, in the formula (1) described in the aforementioned (1), when X is a carboxyl group, Y is a cyano group, Z is a group represented by the formula (3), and said group of the formula (3) is a N—$R_1$-substituted tetrahydroquinoline-6-yl group or a N—$R_1$-substituted carbazole-3-yl group ($R_1$ is same as in the formula (3)), preferably $A_1$, $A_2$ and $A_3$ are each a hydrogen atom, or $A_1$ and $A_3$ or neighboring $A_2$s or neighboring $A_3$s combine together to form a linker having 2 to 3 carbon atoms or a linker composed of an aliphatic chain having 2 carbon atoms and an oxygen atom, which forms a 5- to 6-membered ring (said ring may have a methyl group as a substituent), and remaining $A_1$, $A_2$ and $A_3$ are each a hydrogen atom, or $A_2$ and next but one $A_3$ combine together to form a linker containing a hetero atom selected from the group consisting of a sulfur atom, a nitrogen atom and an oxygen atom and form a 5-membered ring, 1 to 3 of said 5-membered rings are formed, and remaining $A_1$, $A_2$ and $A_3$ are each a hydrogen atom.

Here, examples of a unsaturated hydrocarbon ring or a heterocycle, which may be formed when the above n is other than 0, include benzene ring, naphthalene ring, anthracene ring, phenanthrene ring, pyrene ring, indene ring, azulene ring, fluorene ring, cyclobutene ring, cyclohexene ring, cyclopentene ring, cyclohexadiene ring, cyclopentadiene ring, etc., and examples of the hetero ring include pyridine ring, pyrazine ring, pyperidine ring, indoline ring, furan ring, thiophen ring, pyran ring, oxazole ring, thiazole ring, thiadiazole ring, oxadiazole ring, indole ring, benzothiazole ring, benzoxazole ring, quinoline ring, carbazole ring, benzopyran ring, etc. Among them, preferable rings include benzene ring, cyclobutene ring, cyclopentene ring, cyclohexene ring, pyran ring, furan ring, thiophen ring, etc. These rings may combine together with the benzene ring "b" to form a condensed ring. These rings may have a substituent as described above, and said substituent is same to those described in the section of the substituent in the above-described "an optionally substituted aromatic residue" and "an optionally substituted aliphatic hydrocarbon residue". When the ring to be formed is a heterocycle, and has a carbonyl group, thiocarbonyl group, etc, the ring may form a cyclic ketone, a cyclic thioketone, etc., and may further have a substituent. Such substituent is same to those described in the section of the substituent in the above-described "an optionally substituted aromatic residue" and "an optionally substituted aliphatic hydrocarbon residue".

Benzene ring "b" may have 1 to 3 substituents selected from the group consisting of a halogen atom, an amide group, a hydroxyl group, a cyano group, a nitro group, an alkoxyl group, an acyl group, a substituted or unsubstituted amino group, an optionally substituted aliphatic hydrocarbon residue and an optionally substituted aromatic residue. The halogen atom, the amide group, the alkoxyl group, the acyl group, the substituted or unsubstituted amino group, the optionally substituted aliphatic hydrocarbon residue and the optionally substituted aromatic residue are each same to those described in the section of the substituent in the above-described "an optionally substituted aromatic residue" and "an optionally substituted aliphatic hydrocarbon residue". In addition, when a plural number of substituents exist, these substituents may combine each other or together with $A_1$ and/or $A_2$ and/or $A_3$ to form an optionally substituted ring as described before. Here, said substituent in the optionally substituted ring includes substituents same to those described in the section of the substituent in "an optionally substituted aromatic residue" and "an optionally substituted aliphatic hydrocarbon residue".

Among the methine based dyes represented by the aforementioned formula (1a), a methine based dye represented by the following formula (2a) is preferable.

[KA 9]

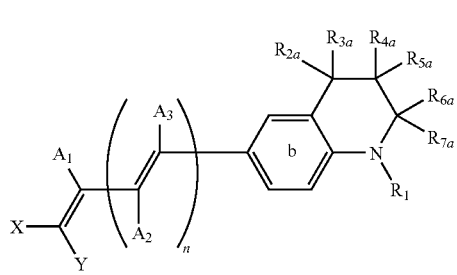

(2a)

In the formula (2a), n, $R_1$, Y, X, $A_1$, $A_2$, $A_3$ and benzene ring "b" are each same as in the formula (1a). In addition, $R_{2a}$ to $R_{7a}$ represent a hydrogen atom, an optionally substituted aromatic residue, an optionally substituted aliphatic hydrocarbon residue or a halogen atom, and are preferably a hydrogen atom or an optionally substituted aliphatic hydrocarbon residue. Particularly preferably, $R_{2a}$ to $R_{7a}$ are each a hydrogen atom, or $R_{2a}$ and $R_{3a}$ are an optionally substituted aliphatic hydrocarbon residue and $R_{4a}$ to $R_{7a}$ are a hydrogen atom. Here, the optionally substituted aromatic residue and the optionally substituted aliphatic hydrocarbon residue are same to the aforementioned "an optionally substituted aromatic residue" and "an optionally substituted aliphatic hydrocarbon residue", respectively. In addition, the halogen atom includes an atom of fluorine, chlorine, bromine, iodine, etc. In addition, $R_{2a}$ to $R_{7a}$ may combine together to form an optionally substituted ring. Said substituent in the optionally substituted ring is same to those described in the section of the substituent in "an optionally substituted aromatic residue" and "an optionally substituted aliphatic hydrocarbon residue".

In addition, the methine based dye represented by the formula (2a) is further preferably a methine based dye represented by the following formula (3a):

[KA 10]

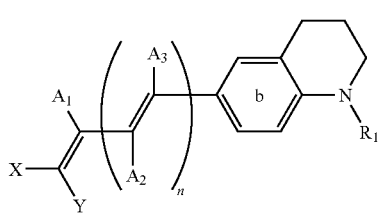

(3a)

In the formula (3a), n, $R_1$, Y, X, $A_1$, $A_2$, $A_3$ and benzene ring "b" are each same as in the formula (1a).

When the methine based dyes represented by the above formula (1) to the above formula (3a) have an acidic group such as carboxyl group, phosphoric acid group, hydroxyl group, sulfonic acid group, etc. as a substituent, the dyes may each form a salt thereof, and examples of the salt include, for example, a salt with an alkali metal or an alkaline earth metal etc. such as lithium, sodium, potassium, magnesium, calcium, etc., or a salt with an organic base, for example, a quaternary ammonium such as tetramethylammonium, tetrabutylammonium, pyridinium, imidazolium, pyperadinium, pyperidinium, etc.

The methine based dyes represented by the above formula (1) to the above formula (3a) can be in a form of structural isomer such as a cis body, a trans body, a mixture thereof, an enantiomer, a racemic form thereof. Form of structural isomer of the dye is not particularly limited, and any form of isomer can be suitably used as a photo-sensitizing dye in the present invention.

The methine based dyes represented by the above formula (1a) can be prepared, for example, according to the following reaction scheme. Namely, the methine based dye of the formula (1a) can be obtained by condensing a compound having an active methylene represented by the following formula (5a) and a carbonyl compound represented by the following formula (4a) in the presence of a basic catalyst such as sodium hydroxide, sodium methylate, sodium acetate, diethylamine, triethylamine, pyperidine, pyperazine, diazabicycloundecene, etc., if necessary, in a solvent, for example, alcohols such as methanol, ethanol, isopropanol, butanol, etc., aprotic polar solvent such as dimethylformamide, N-methylpyrrolidone, etc., toluene, acetic anhydride, acetonitrile, etc., at 20° C. to 180° C., preferably 50° C. to 150° C. The compound having an active methylene represented by the formula (5a) can be easily available in the market, and the carbonyl compound represented by the formula (4a), in which X is trimethylene as an example, can be obtained by a known process, for example, by performing N-alkylation of 1,2,3,4-tetrahydroquinoline followed by subjecting to formylation or the like. In the formula (4a), n, $R_1$, X, $A_1$, $A_2$, $A_3$ and benzene ring "b" are each same as in the formula (1a). In addition, in the formula (5a), X and Y are each same as in the formula (1a).

[KA 11]

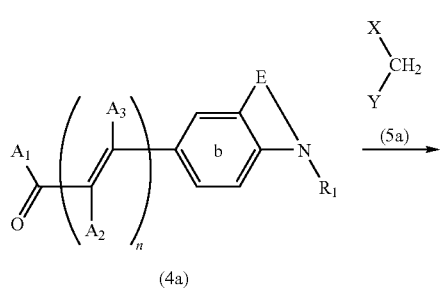

(4a)

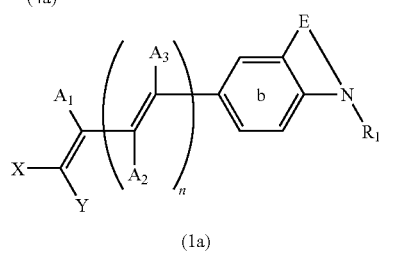

(1a)

Hereinafter, specific examples of the methine based dye (compound) represented by the above formula (1a) will be exemplified.

Firstly, among the methine based dyes represented by the formula (1a), specific examples of the methine based dyes represented by the following formula (6a) are shown in Table 1 and Table 2. In each Table, Ph means a phenyl group.

In addition, in the following formula (6a), preferably $X_1$ is a carboxyl group, $Y_1$ is a cyano group, $A_4$ to $A_6$ are a hydrogen atom, $R_1$ is a ($C_1$-$C_{18}$) alkyl group, and $R_{9a}$ to $R_{13a}$ are a hydrogen atom.

[KA 12]

(6a)

TABLE 1

| Compound | n | $X_1$ | $Y_1$ | $A_4$ | $A_5$ | $A_6$ | $R_{8a}$ | $R_{9a}$ | $R_{10a}$ | $R_{11a}$ | $R_{12a}$ | $R_{13a}$ |
|---|---|---|---|---|---|---|---|---|---|---|---|---|
| 1a | 0 | H | H | H | — | — | H | H | H | H | H | H |
| 2a | 0 | COOH | CN | H | — | — | $CH_3$ | H | H | H | H | H |
| 3a | 0 | COOH | CN | H | — | — | $C_2H_5$ | H | H | H | H | H |
| 4a | 0 | COOH | CN | H | — | — | n-$C_4H_9$ | H | H | H | H | H |
| 5a | 0 | COOH | CN | H | — | — | n-$C_8H_{17}$ | H | H | H | H | H |
| 6a | 0 | COOH | CN | H | — | — | n-$C_{18}H_{37}$ | H | H | H | H | H |
| 7a | 0 | COOH | CN | H | — | — | Ph | H | H | H | H | H |
| 8a | 0 | COOH | COOH | H | — | — | n-$C_8H_{17}$ | H | H | H | H | H |
| 9a | 0 | COOH | $COCH_3$ | H | — | — | n-$C_8H_{17}$ | H | H | H | H | H |
| 10a | 0 | COOH | $COCF_3$ | H | — | — | n-$C_8H_{17}$ | H | H | H | H | H |
| 11a | 0 | $PO(OH)_2$ | CN | H | — | — | n-$C_8H_{17}$ | H | H | H | H | H |
| 12a | 0 | $SO_3H$ | CN | H | — | — | n-$C_8H_{17}$ | H | H | H | H | H |
| 13a | 0 | $COOCH_3$ | CN | H | — | — | n-$C_8H_{17}$ | H | H | H | H | H |
| 14a | 0 | COOLi | CN | H | — | — | n-$C_8H_{17}$ | H | H | H | H | H |
| 15a | 0 | COONa | CN | H | — | — | n-$C_8H_{17}$ | H | H | H | H | H |
| 16a | 0 | COOK | CN | H | — | — | n-$C_8H_{17}$ | H | H | H | H | H |
| 17a | 0 | COOH | $PO(OH)_2$ | H | — | — | n-$C_8H_{17}$ | H | H | H | H | H |
| 18a | 0 | $PO(OH)_2$ | $PO(OH)_2$ | H | — | — | n-$C_8H_{17}$ | H | H | H | H | H |
| 19a | 0 | COOH | $NO_2$ | H | — | — | n-$C_8H_{17}$ | H | H | H | H | H |
| 20a | 0 | COOH | Cl | H | — | — | n-$C_8H_{17}$ | H | H | H | H | H |
| 21a | 0 | COOH | CN | H | — | — | n-$C_8H_{17}$ | $CH_3$ | $CH_3$ | H | H | H |
| 22a | 0 | COOH | CN | H | — | — | n-$C_8H_{17}$ | H | H | H | OH | H |
| 23a | 0 | COOH | CN | H | — | — | n-$C_8H_{17}$ | H | H | $CH_3$ | $CH_3$ | $CH_3$ |
| 24a | 0 | COOH | CN | H | — | — | n-$C_8H_{17}$ | H | H | H | H | $OCH_3$ |
| 25a | 0 | COOH | CN | H | — | — | n-$C_8H_{17}$ | H | H | H | Cl | H |
| 26a | 0 | COOH | COPh | H | — | — | n-$C_8H_{17}$ | H | H | H | H | H |
| 27a | 0 | COOH | $COC(CH_3)_3$ | H | — | — | n-$C_8H_{17}$ | H | H | H | H | H |
| 28a | 0 | COOH | $SO_2CF_3$ | H | — | — | n-$C_8H_{17}$ | H | H | H | H | H |
| 29a | 0 | COONa | COONa | H | — | — | n-$C_8H_{17}$ | H | H | H | H | H |
| 30a | 0 | COOH | CN | $CH_3$ | — | — | n-$C_8H_{17}$ | H | H | H | H | H |
| 31a | 0 | COOH | CN | Ph | — | — | n-$C_8H_{17}$ | H | H | H | H | H |
| 32a | 1 | COOH | CN | H | H | H | n-$C_8H_{17}$ | H | H | H | H | H |
| 33a | 1 | COOH | CN | H | H | H | n-$C_8H_{17}$ | $CH_3$ | $CH_3$ | H | H | H |
| 34a | 1 | COOH | CN | H | $CH_3$ | $CH_3$ | n-$C_8H_{17}$ | H | H | H | H | H |
| 35a | 1 | COOH | CN | H | H | $CH_3$ | n-$C_8H_{17}$ | H | H | H | H | H |
| 36a | 1 | COOH | CN | H | $CH_3$ | H | n-$C_8H_{17}$ | H | H | H | H | H |
| 37a | 1 | COOH | CN | $CH_3$ | $CH_3$ | $CH_3$ | n-$C_8H_{17}$ | H | H | H | H | H |
| 38a | 1 | COOH | CN | H | H | Ph | n-$C_8H_{17}$ | H | H | H | H | H |
| 39a | 1 | COOH | CN | H | H | H | Ph | H | H | H | H | H |
| 40a | 1 | COOH | CN | H | H | H | $CH(CH_3)_2$ | H | H | H | H | H |
| 41a | 1 | COOH | CN | H | H | H | $C(CH_3)_3$ | H | H | H | H | H |
| 42a | 1 | COOH | Ph | H | H | H | n-$C_8H_{17}$ | H | H | H | H | H |
| 43a | 1 | COOH | $CH_2CH_3$ | H | H | H | n-$C_8H_{17}$ | H | H | H | H | H |
| 44a | 1 | $PO(ONa)_2$ | CN | H | H | H | n-$C_8H_{17}$ | H | H | H | H | H |

TABLE 1-continued

| Compound | n | $X_1$ | $Y_1$ | $A_4$ | $A_5$ | $A_6$ | $R_{8a}$ | $R_{9a}$ | $R_{10a}$ | $R_{11a}$ | $R_{12a}$ | $R_{13a}$ |
|---|---|---|---|---|---|---|---|---|---|---|---|---|
| 45a | 1 | COOH | CN | H | H | H | $C_2H_4Cl$ | H | H | H | H | H |
| 46a | 1 | COOH | CN | H | H | H | $C_2H_4OH$ | H | H | H | H | H |
| 47a | 1 | COOH | CN | H | H | H | $C_2H_4OCH_3$ | H | H | H | H | H |
| 48a | 1 | COOH | CN | H | H | H | $C_2H_4CN$ | H | H | H | H | H |

TABLE 2

| Compound | n | $X_1$ | $Y_1$ | $A_4$ | $A_5$ | $A_6$ | $R_{8a}$ | $R_{9a}$ | $R_{10a}$ | $R_{11a}$ | $R_{12a}$ | $R_{13a}$ |
|---|---|---|---|---|---|---|---|---|---|---|---|---|
| 49a | 1 | COOH | CN | H | H | H | $C_4H_8OCH_3$ | H | H | H | H | H |
| 50a | 1 | COOH | CN | H | H | H | $C_2H_4OPh$ | H | H | H | H | H |
| 51a | 1 | COOH | CN | H | H | H | $n-C_8H_{17}$ | H | H | $C_2H_5$ | H | H |
| 52a | 1 | COOH | CN | H | H | H | $n-C_8H_{17}$ | H | H | H | $NO_2$ | H |
| 53a | 1 | COOH | CN | H | H | H | $n-C_8H_{17}$ | H | H | H | $OCH_3$ | H |
| 54a | 1 | COOH | CN | H | H | H | $n-C_8H_{17}$ | H | H | H | H | Cl |
| 55a | 1 | COOH | CN | H | H | H | $n-C_8H_{17}$ | H | H | H | CN | H |
| 56a | 1 | COOH | CN | CN | H | H | $n-C_8H_{17}$ | H | H | H | H | H |
| 57a | 1 | COOH | CN | H | H | H | $n-C_8H_{17}$ | Ph | H | H | H | H |
| 58a | 1 | COOH | CN | H | H | H | $n-C_8H_{17}$ | H | H | H | $NHCOCH_3$ | H |
| 59a | 1 | COOH | CN | H | H | H | $n-C_8H_{17}$ | H | H | H | $NHCOCF_3$ | H |
| 60a | 1 | COOH | CN | H | H | H | $n-C_8H_{17}$ | H | H | H | $CF_3$ | H |
| 61a | 1 | COOH | $CF_3$ | H | H | H | $n-C_8H_{17}$ | H | H | H | H | H |
| 62a | 1 | COOH | F | H | H | H | $n-C_8H_{17}$ | H | H | H | H | H |
| 63a | 1 | COOH | CN | H | H | H | $CF_3$ | H | H | H | H | H |
| 64a | 1 | COOH | CN | H | H | H | $C_2F_5$ | H | H | H | H | H |
| 65a | 1 | COOH | CN | H | H | H | $c_4F_9$ | H | H | H | H | H |
| 66a | 1 | COOH | CN | H | H | H | $C_8F_{17}$ | H | H | H | H | H |
| 67a | 1 | COOH | CN | H | H | H | $CH_2CF_3$ | H | H | H | H | H |
| 68a | 1 | COOH | CN | H | H | H | $n-C_8H_{17}$ | $CF_3$ | $CF_3$ | H | H | H |
| 69a | 1 | COOH | CN | H | H | H | $n-C_8H_{17}$ | H | H | H | $NH_2$ | H |
| 70a | 1 | COOH | CN | H | H | H | $n-C_8H_{17}$ | H | H | H | $NHCH_3$ | H |
| 71a | 1 | COOH | CN | H | H | H | $n-C_8H_{17}$ | H | H | H | NHPh | H |
| 72a | 1 | COOH | CN | H | H | H | $n-C_8H_{17}$ | H | H | H | $N(CH_3)_2$ | H |
| 73a | 1 | COOH | CN | H | H | H | $n-C_8H_{17}$ | H | H | H | $COCH_3$ | H |
| 74a | 1 | COOH | CN | H | H | H | $n-C_8H_{17}$ | H | H | H | $COCF_3$ | H |
| 75a | 1 | COOH | CN | H | H | H | $CH_2Ph$ | H | H | H | H | H |
| 76a | 1 | COOH | CN | H | H | H | $C_2H_4Ph$ | H | H | H | H | H |
| 77a | 1 | COOH | CN | H | H | H | $n-C_8H_{17}$ | H | H | H | OH | H |
| 78a | 1 | COOH | CN | H | H | H | $n-C_8H_{17}$ | H | H | H | ONa | H |
| 79a | 1 | COONa | CN | H | H | H | $n-C_8H_{17}$ | H | H | H | ONa | H |
| 80a | 1 | COOH | CN | H | H | H | $n-C_8H_{17}$ | H | H | H | $OC_4H_9$ | H |
| 81a | 1 | COOH | CN | H | H | H | $n-C_8H_{17}$ | H | H | H | $O(n-C_8H_{17})$ | H |
| 82a | 1 | COOH | CN | H | H | H | $n-C_8H_{17}$ | H | H | H | H | $CH_3$ |
| 83a | 1 | COOH | CN | H | H | H | $C_3H_6Cl$ | H | H | H | H | H |
| 84a | 1 | COOH | CN | H | H | H | $C_3H_6Br$ | H | H | H | H | H |
| 85a | 1 | COOH | CN | H | H | H | $CH_2COOH$ | H | H | H | H | H |
| 86a | 1 | CN | CN | H | H | H | $CH_2COOH$ | H | H | H | H | H |
| 87a | 2 | COOH | CN | H | H | H | $n-C_8H_{17}$ | H | H | H | H | H |
| 88a | 2 | COOH | CN | $CH_3$ | H | H | $n-C_8H_{17}$ | H | H | H | H | H |
| 89a | 2 | COOH | CN | $CH_3$ | $CH_3$ | $CH_3$ | $n-C_8H_{17}$ | H | H | H | H | H |
| 90a | 2 | COOH | CN | H | H | $CH_3$ | $n-C_8H_{17}$ | H | H | H | H | H |
| 91a | 2 | COOH | CN | H | H | H | $n-C_8H_{17}$ | $CH_3$ | $CH_3$ | H | H | H |
| 92a | 3 | COOH | CN | H | H | H | $n-C_8H_{17}$ | H | H | H | H | H |
| 93a | 4 | COOH | CN | H | H | H | $n-C_8H_{17}$ | H | H | H | H | H |
| 94a | 5 | COOH | CN | H | H | H | $n-C_8H_{17}$ | H | H | H | H | H |
| 95a | 6 | COOH | CN | H | H | H | $n-C_8H_{17}$ | H | H | H | H | H |
| 96a | 7 | COOH | CN | H | H | H | $n-C_8H_{17}$ | H | H | H | H | H |

Next, among the methine based dyes represented by the formula (1a), specific examples of the methine based dyes represented by the following formula (7a) are shown in Table 3 and Table 4. In each Table, Ph means a phenyl group.

In addition, in the following formula (7a), preferably $X_2$ is a carboxyl group, $Y_2$ is a cyano group, $A_7$ to $A_9$ are a hydrogen atom, $R_{14a}$ to $R_{17a}$ are a hydrogen atom, $R_{18a}$ is a ($C_1$-$C_{18}$) alkyl group, and $R_{19a}$ to $R_{23a}$ are a hydrogen atom.

[KA 13]

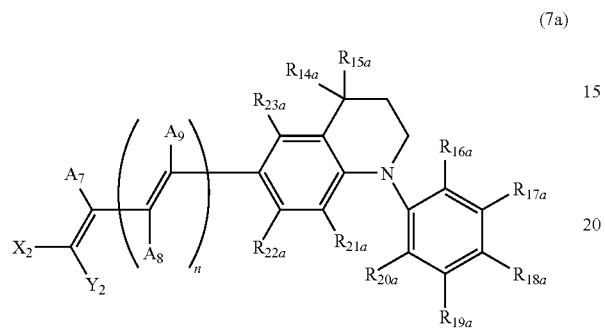

(7a)

TABLE 3

| Compound | n | $X_2$ | $Y_2$ | $A_7$ | $A_8$ | $A_9$ | $R_{14a}$ | $R_{15a}$ | $R_{16a}$ | $R_{17a}$ | $R_{18a}$ | $R_{19a}$ | $R_{20a}$ | $R_{21a}$ | $R_{22a}$ | $R_{23a}$ |
|---|---|---|---|---|---|---|---|---|---|---|---|---|---|---|---|---|
| 97a | 0 | H | H | H | — | — | H | H | H | H | H | H | H | H | H | H |
| 98a | 0 | COOH | CN | H | — | — | H | H | H | H | H | H | H | H | H | H |
| 99a | 0 | COOH | CN | H | — | — | H | H | H | H | $CH_3$ | H | H | H | H | H |
| 100a | 0 | COOH | CN | H | — | — | H | H | H | H | $C_2H_5$ | H | H | H | H | H |
| 101a | 0 | COOH | CN | H | — | — | H | H | H | H | n-$C_4H_9$ | H | H | H | H | H |
| 102a | 0 | COOH | CN | H | — | — | H | H | H | H | n-$C_8H_{17}$ | H | H | H | H | H |
| 103a | 0 | COOH | CN | H | — | — | H | H | H | H | n-$C_{18}H_{37}$ | H | H | H | H | H |
| 104a | 0 | COOH | COOH | H | — | — | H | H | H | $CH_3$ | H | $CH_3$ | H | H | H | H |
| 105a | 0 | COOH | $COCH_3$ | H | — | — | H | H | H | H | $CH_3$ | H | H | H | H | H |
| 106a | 0 | COOH | $COCF_3$ | H | — | — | H | H | H | H | $CH_3$ | H | H | H | H | H |
| 107a | 0 | $PO(OH)_2$ | CN | H | — | — | H | H | H | H | n-$C_8H_{17}$ | H | H | H | H | H |
| 108a | 0 | $SO_3H$ | CN | H | — | — | H | H | H | H | n-$C_8H_{17}$ | H | H | H | H | H |
| 109a | 0 | $COOCH_3$ | CN | H | — | — | H | H | H | H | n-$C_8H_{17}$ | H | H | H | H | H |
| 110a | 0 | COOLi | CN | H | — | — | H | H | H | H | n-$C_8H_{17}$ | H | H | H | H | H |
| 111a | 0 | COONa | CN | H | — | — | H | H | H | H | n-$C_8H_{17}$ | H | H | H | H | H |
| 112a | 0 | COOK | CN | H | — | — | H | H | H | H | n-$C_8H_{17}$ | H | H | H | H | H |
| 113a | 0 | COOH | $PO(OH)_2$ | H | — | — | H | H | H | H | n-$C_8H_{17}$ | H | H | H | H | H |
| 114a | 0 | $PO(OH)_2$ | $PO(OH)_2$ | H | — | — | H | H | H | H | n-$C_8H_{17}$ | H | H | H | H | H |
| 115a | 0 | COOH | $NO_2$ | H | — | — | H | H | H | H | $CH_3$ | H | H | H | H | H |
| 116a | 0 | COOH | Cl | H | — | — | H | H | H | H | $CH_3$ | H | H | H | H | H |
| 117a | 0 | COOH | CN | H | — | — | $CH_3$ | $CH_3$ | H | H | $CH_3$ | H | H | H | H | H |
| 118a | 0 | COOH | CN | H | — | — | H | H | H | OH | $CH_3$ | H | H | H | H | H |
| 119a | 0 | COOH | CN | H | — | — | H | H | H | H | $OCH_3$ | H | H | H | H | H |
| 120a | 0 | COOH | CN | H | — | — | H | H | H | $OCH_3$ | H | H | H | H | H | H |
| 121a | 0 | COOH | CN | H | — | — | H | H | H | Cl | H | Cl | H | H | H | H |
| 122a | 0 | COOH | COPh | H | — | — | H | H | $CH_3$ | H | H | H | $CH_3$ | H | H | H |
| 123a | 0 | COOH | $COC(CH_3)_3$ | H | — | — | H | H | $CH_3$ | H | $CH_3$ | H | H | H | H | H |
| 124a | 0 | COOH | $SO_2CF_3$ | H | — | — | H | H | H | H | H | H | H | H | H | H |
| 125a | 0 | COONa | COONa | H | — | — | H | H | H | H | H | H | H | H | H | H |
| 126a | 0 | COOH | CN | $CH_3$ | — | — | H | H | H | H | H | H | H | H | H | H |
| 127a | 0 | COOH | CN | Ph | — | — | H | H | H | H | H | H | H | H | H | H |
| 128a | 1 | COOH | CN | H | H | H | H | H | H | H | Ph | H | H | H | H | H |
| 129a | 1 | COOH | CN | H | H | H | $CH_3$ | $CH_3$ | H | H | Ph | H | H | H | H | H |
| 130a | 1 | COOH | CN | H | $CH_3$ | $CH_3$ | H | H | H | H | $CH_3$ | H | H | H | H | H |
| 131a | 1 | COOH | CN | H | H | $CH_3$ | H | H | H | H | $CH_3$ | H | H | H | H | H |
| 132a | 1 | COOH | CN | H | $CH_3$ | H | H | H | H | H | $CH_3$ | H | H | H | H | H |
| 133a | 1 | COOH | CN | $CH_3$ | $CH_3$ | $CH_3$ | H | H | H | H | $CH_3$ | H | H | H | H | H |
| 134a | 1 | COOH | CN | H | H | Ph | H | H | H | H | $CH_3$ | H | H | H | H | H |
| 135a | 1 | COOH | CN | H | H | H | H | H | H | n-$C_4H_9$ | H | n-$C_4H_9$ | H | H | H | H |
| 136a | 1 | COOH | CN | H | H | H | H | H | H | H | $NO_2$ | H | H | H | H | H |
| 137a | 1 | COOH | CN | H | H | H | H | H | H | H | $NH_2$ | H | H | H | H | H |
| 138a | 1 | COOH | Ph | H | H | H | H | H | H | H | O(n-$C_4H_9$) | H | H | H | H | H |
| 139a | 1 | COOH | $C_2H_5$ | H | H | H | H | H | H | H | H | H | H | H | H | H |
| 140a | 1 | $PO(ONa)_2$ | CN | H | H | H | H | H | H | H | n-$C_4H_9$ | H | H | H | H | H |
| 141a | 1 | COOH | CN | H | H | H | H | H | H | H | n-$C_5H_{13}$ | H | H | H | H | H |

TABLE 3-continued

| Compound | n | $X_2$ | $Y_2$ | $A_7$ | $A_8$ | $A_9$ | $R_{14a}$ | $R_{15a}$ | $R_{16a}$ | $R_{17a}$ | $R_{18a}$ | $R_{19a}$ | $R_{20a}$ | $R_{21a}$ | $R_{22a}$ | $R_{23a}$ |
|---|---|---|---|---|---|---|---|---|---|---|---|---|---|---|---|---|
| 142a | 1 | COOH | CN |  |  |  | H | H | H | H | n-$C_4H_9$ | H | H | Cl | H | H |
| 143a | 1 | COOH | CN |  |  |  | H | H | H | H | n-$C_4H_9$ | H | H | H | Cl | H |
| 144a | 1 | COOH | CN |  |  |  | H | H | H | H | n-$C_4H_9$ | H | H | H | H | Cl |

TABLE 4

| Compound | n | $X_2$ | $Y_2$ | $A_7$ | $A_8$ | $A_9$ | $R_{14a}$ | $R_{15a}$ | $R_{16a}$ | $R_{17a}$ | $R_{18a}$ | $R_{19a}$ | $R_{20a}$ | $R_{21a}$ | $R_{22a}$ | $R_{23a}$ |
|---|---|---|---|---|---|---|---|---|---|---|---|---|---|---|---|---|
| 145a | 1 | COOH | CN | H | H | H | H | H | H | H | Cl | H | H | H | H | H |
| 146a | 1 | COOH | CN | H | H | H | H | H | H | H | Br | H | H | H | H | H |
| 147a | 1 | COOH | CN | H | H | H | H | H | H | H | $CH_3$ | H | H | H | H | H |
| 148a | 1 | COOH | CN | H | H | H | H | H | H | H | $C_2H_5$ | H | H | H | H | H |
| 149a | 1 | COOH | CN | H | H | H | H | H | H | H | n-$C_4H_9$ | H | H | H | H | H |
| 150a | 1 | COOH | CN | H | H | H | H | H | H | H | n-$C_8H_{17}$ | H | H | H | H | H |
| 151a | 1 | COOH | CN | H | H | H | H | H | H | H | n-$C_{18}H_{37}$ | H | H | H | H | H |
| 152a | 1 | COOH | CN | H | H | H | H | H | H | $CH_3$ | H | $CH_3$ | H | H | H | H |
| 153a | 1 | COOH | CN | H | H | H | H | H | H | H | OH | H | H | H | H | H |
| 154a | 1 | COOH | CN | n-$C_8H_{17}$ | H | H | H | H | H | H | $CH_3$ | H | H | H | H | H |
| 155a | 1 | COOH | CN | H | H | H | H | H | H | H | n-$C_8H_{17}$ | H | H | H | H | H |
| 156a | 1 | COOH | CN | H | H | H | H | H | Cl | H | Cl | H | H | H | H | H |
| 157a | 1 | COOH | $CF_3$ | H | H | H | H | H | H | H | n-$C_8H_{17}$ | H | H | H | H | H |
| 158a | 1 | COOH | F | H | H | H | H | H | H | H | n-$C_8H_{17}$ | H | H | H | H | H |
| 159a | 1 | COOH | $C_2H_5$ | H | H | H | H | H | H | H | n-$C_8H_{17}$ | H | H | H | H | H |
| 160a | 1 | COOH | CN | H | H | H | H | H | H | H | n-$C_8H_{17}$ | H | H | H | H | H |
| 161a | 1 | COOH | CN | H | H | H | H | H | n-$C_8H_{17}$ | H | n-$C_8H_{17}$ | H | H | H | H | H |
| 162a | 1 | COOH | CN | H | H | H | H | H | H | H | n-$C_{18}H_{37}$ | H | H | H | H | H |
| 163a | 1 | COOH | CN | H | H | H | H | H | H | H | $CH_3$ | H | H | H | H | H |
| 164a | 1 | COOH | CN | H | H | H | H | H | H | H | $CH_3$ | H | H | H | H | H |
| 165a | 1 | COOH | CN | H | H | H | $CH_3$ | $CH_3$ | H | H | $CH_3$ | H | H | H | H | H |
| 166a | 1 | COOH | CN | H | H | H | H | H | H | OH | $CH_3$ | H | H | H | H | H |
| 167a | 1 | COOH | CN | H | H | H | H | H | H | H | $OCH_3$ | H | H | H | H | H |
| 168a | 1 | COOH | CN | H | H | H | H | H | H | $OCH_3$ | H | H | H | H | H | H |
| 169a | 1 | COOH | CN | H | H | H | H | H | H | Cl | H | Cl | H | H | H | H |
| 170a | 1 | COOH | CN | H | H | H | H | H | $CH_3$ | H | H | H | $CH_3$ | H | H | H |
| 171a | 1 | COOH | CN | H | H | H | H | H | $CH_3$ | H | $CH_3$ | H | H | H | H | H |
| 172a | 1 | COOH | CN | H | H | H | H | H | H | H | H | H | H | H | H | H |
| 173a | 1 | COOH | CN | H | H | H | H | H | H | H | SCN | H | H | H | H | H |
| 174a | 1 | COOH | CN | $CH_3$ | H | H | H | H | H | H | H | H | H | H | H | H |
| 175a | 1 | COONa | CN | Ph | H | H | H | H | H | H | H | H | H | H | H | H |
| 176a | 1 | COOH | CN | H | H | H | H | H | H | H | Ph | H | H | H | H | H |
| 177a | 1 | COOH | CN | H | H | H | $CH_3$ | $CH_3$ | H | H | Ph | H | H | H | H | H |
| 178a | 1 | COOH | CN | H | $CH_3$ | $CH_3$ | H | H | H | H | $CH_3$ | H | H | H | H | H |
| 179a | 1 | COOH | CN | H | H | $CH_3$ | H | H | H | H | $CH_3$ | H | H | H | H | H |
| 180a | 1 | COOH | CN | H | $CH_3$ | H | H | H | H | H | $CH_3$ | H | H | H | H | H |
| 181a | 1 | COOH | CN | $CH_3$ | $CH_3$ | $CH_3$ | H | H | H | H | $CH_3$ | H | H | H | H | H |
| 182a | 1 | CN | CN | H | H | Ph | H | H | H | H | $CH_3$ | H | H | H | H | H |
| 183a | 2 | COOH | CN | H | H | H | H | H | H | H | n-$C_4H_9$ | H | $C_4H_9$ | H | H | H |
| 184a | 2 | COOH | CN | H | H | H | H | H | H | H | $CH_3$ | H | H | H | H | H |
| 185a | 2 | COOH | CN | H | H | H | H | H | H | H | H | H | H | H | H | H |
| 186a | 2 | COOH | CN | H | H | H | H | H | H | H | n-$C_8H_{17}$ | H | H | H | H | H |
| 187a | 2 | COOH | CN | H | H | H | H | H | H | $CH_3$ | H | $CH_3$ | H | H | H | H |
| 188a | 3 | COOH | CN | H | H | H | H | H | H | H | n-$C_8H_{17}$ | H | H | H | H | H |
| 189a | 4 | COOH | CN | H | H | H | H | H | H | H | n-$C_8H_{17}$ | H | H | H | H | H |
| 190a | 5 | COOH | CN | H | H | H | H | H | H | H | n-$C_8H_{17}$ | H | H | Cl | H | H |
| 191a | 6 | COOH | CN | H | H | H | H | H | H | H | n-$C_8H_{17}$ | H | H | H | Cl | H |
| 192a | 7 | COOH | CN | H | H | H | H | H | H | H | n-$C_8H_{17}$ | H | H | H | H | Cl |

In addition, other specific examples of the methine based dyes represented by the formula (1a) are shown below.
[KA 14]
(193)
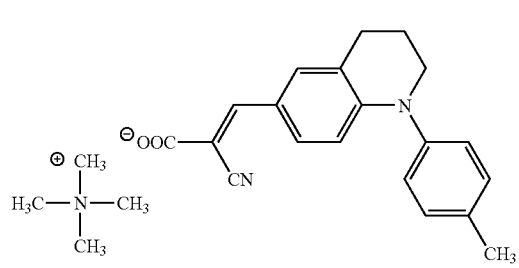
(194)
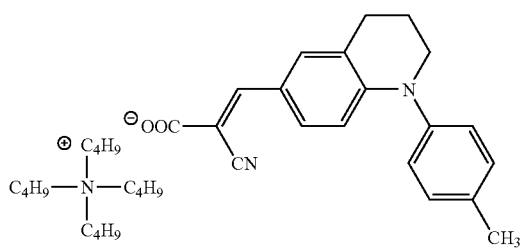
(195)
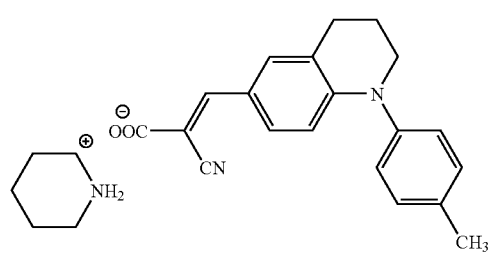
(196)
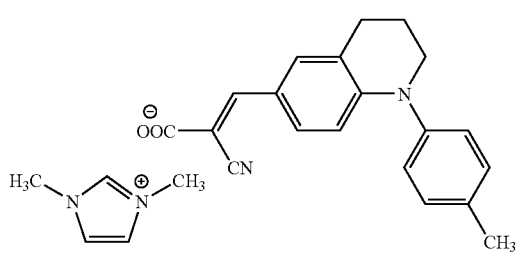
(197)
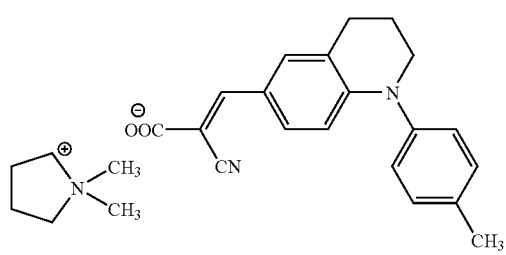
(198)
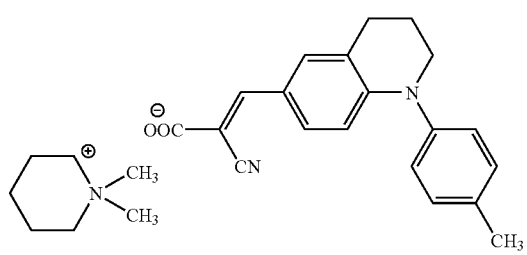
(199)
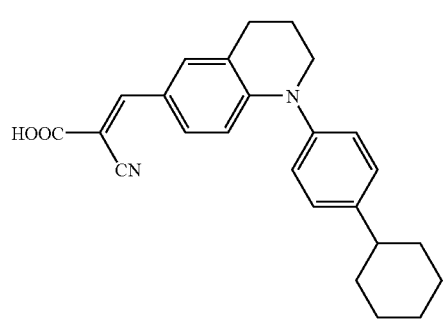
(200)
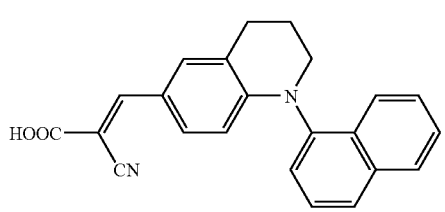
(201)
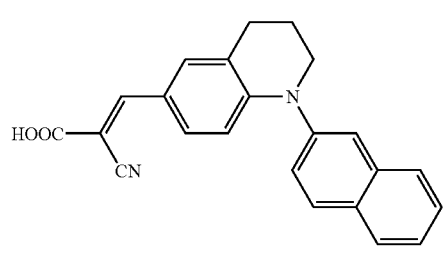
(202)
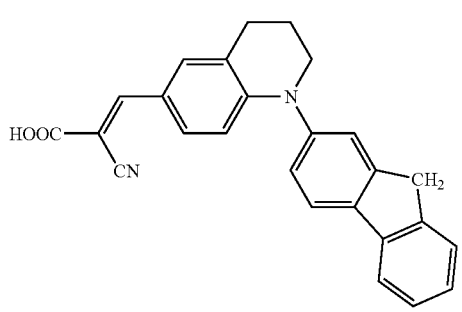

-continued
(203) 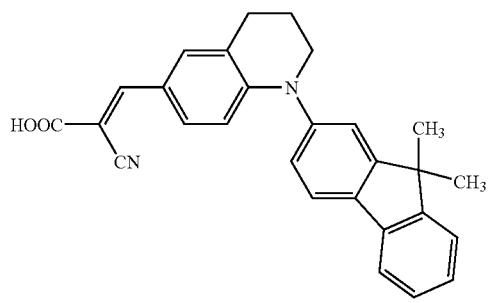
(204) 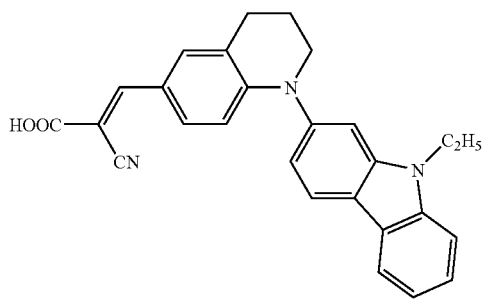
(205) 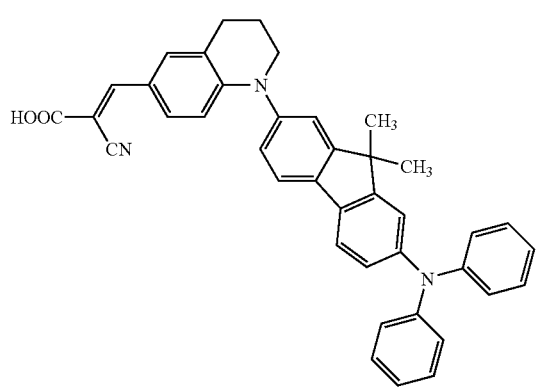
(206) 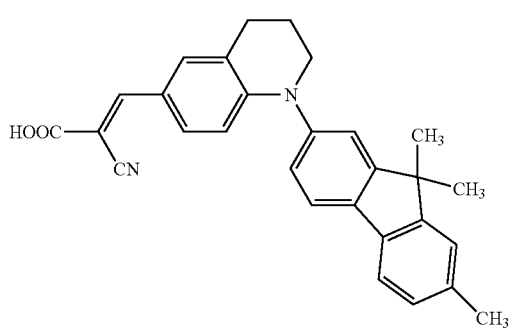
(207) 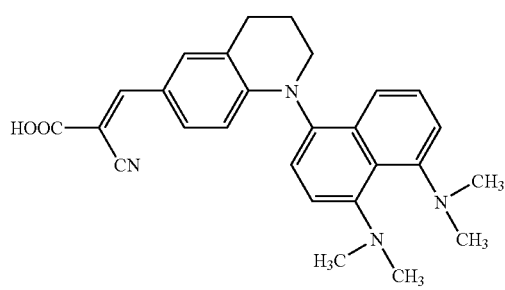
(208) 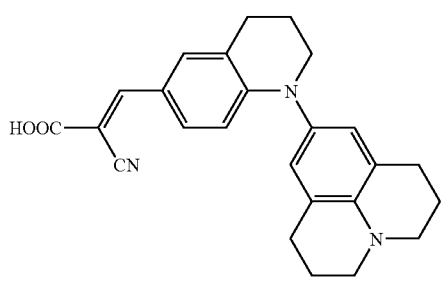
(209) 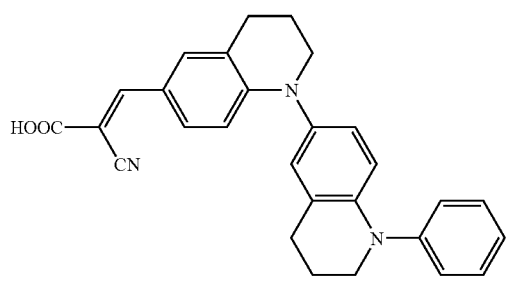
(210) 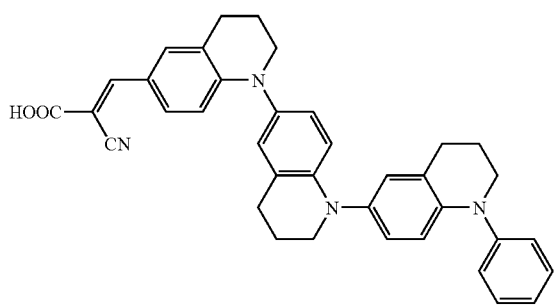

-continued
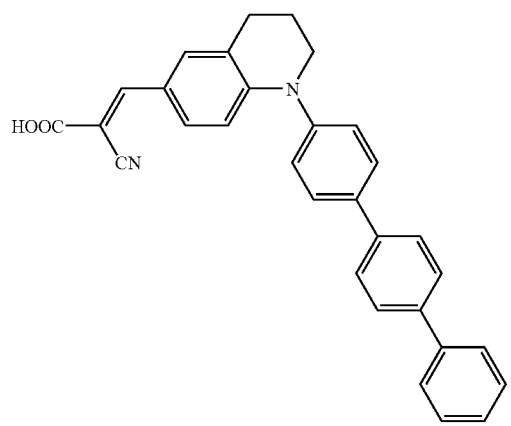
(211)
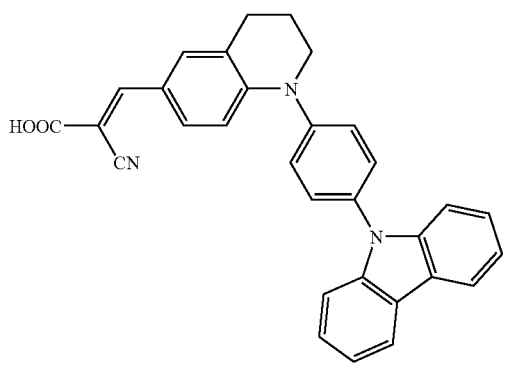
(212)
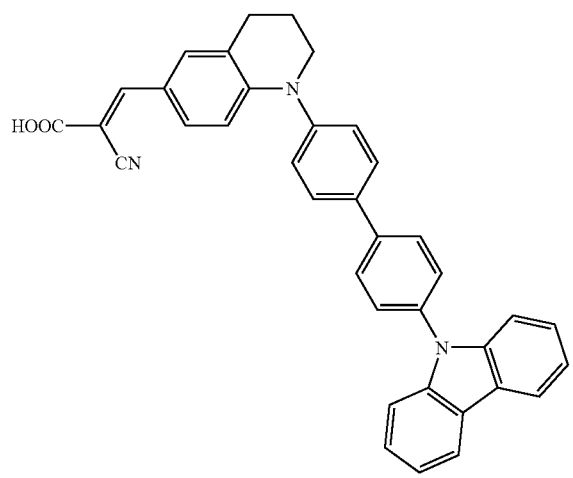
(213)
[KA15]
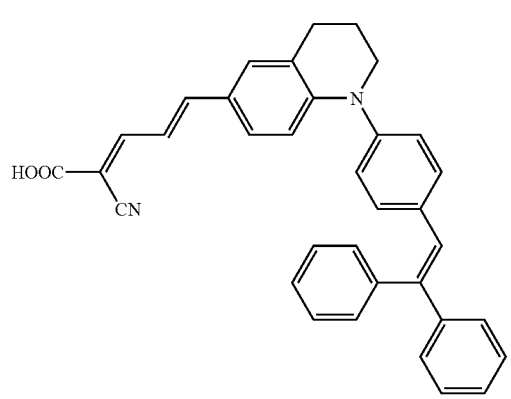
(214)
(215)

-continued
(216) 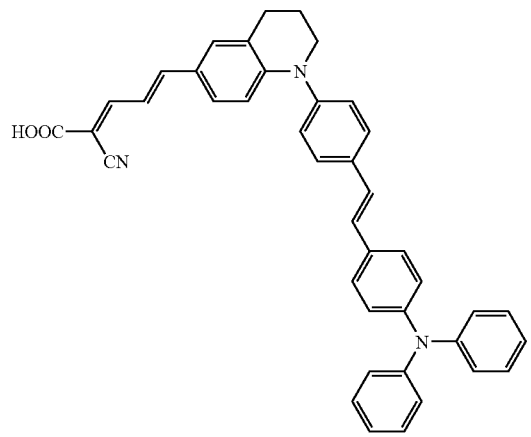
(217) 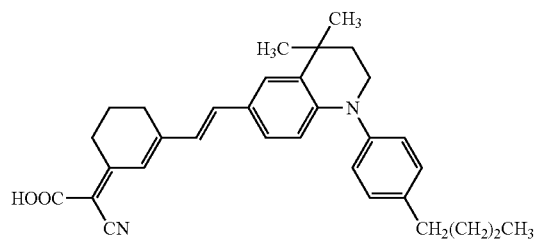
(218) 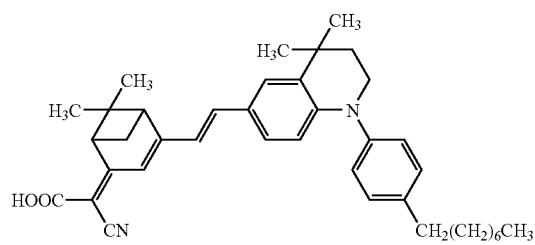
(219) 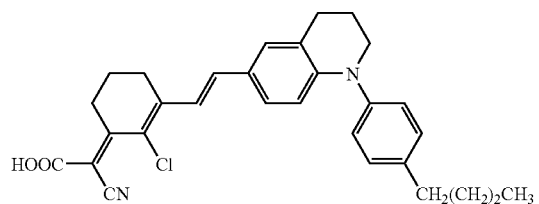
(220) 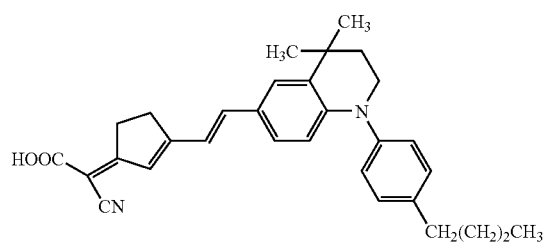
(221) 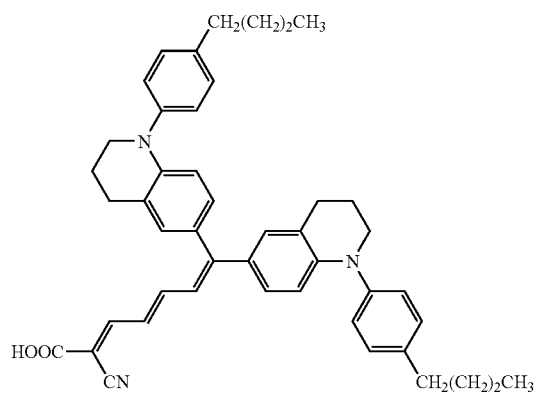
(222) 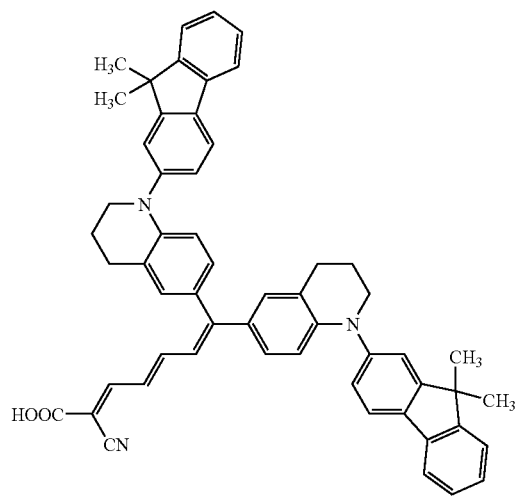
(223) 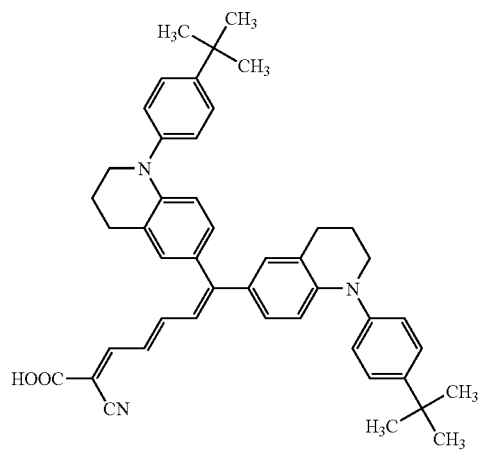

(224)
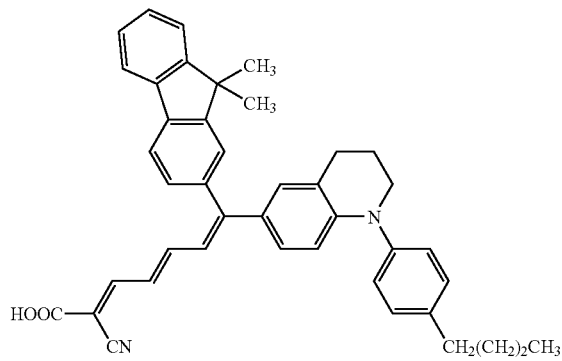
(225)
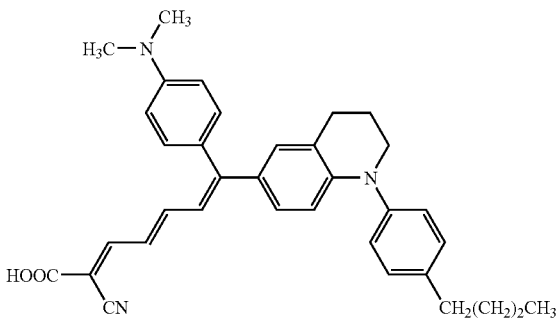
(226)
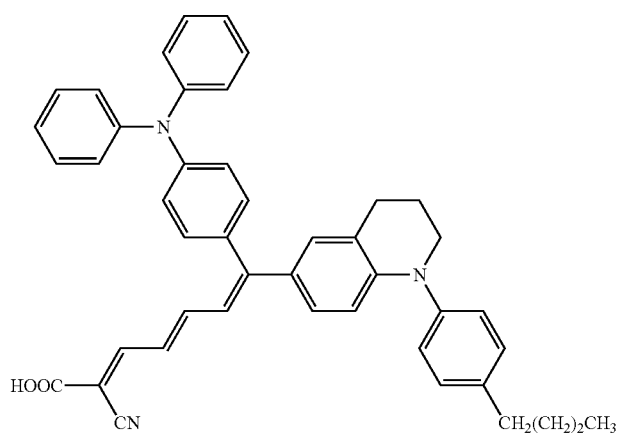
[KA 16]
(227)
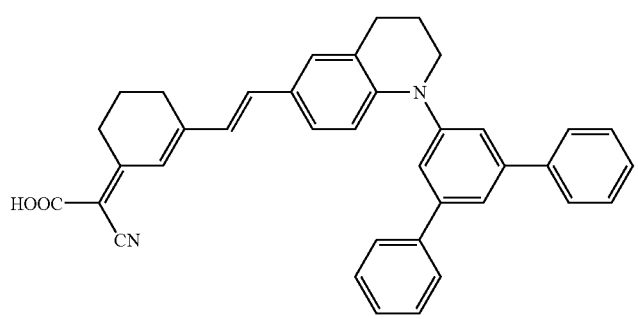
(228)
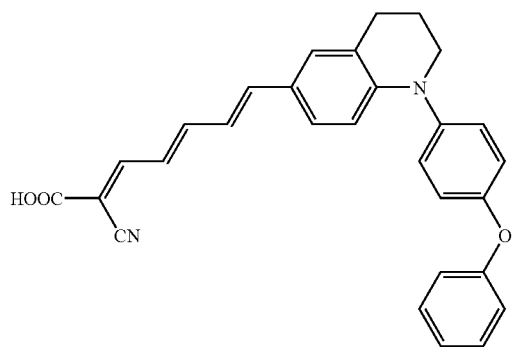
(229)

-continued
(230)
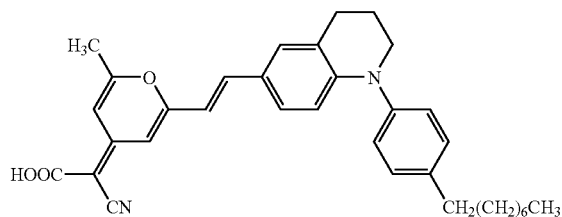
(231)
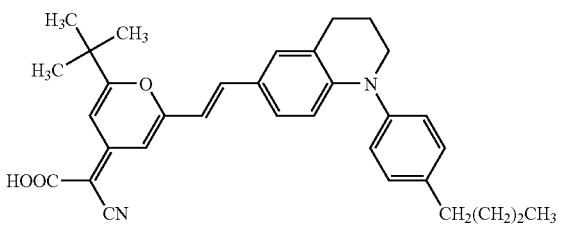
(232)
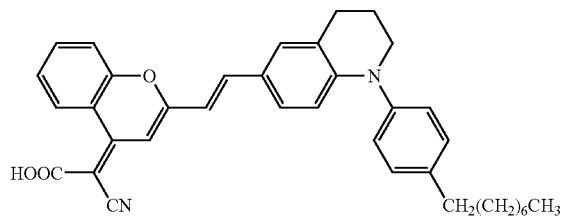
(233)
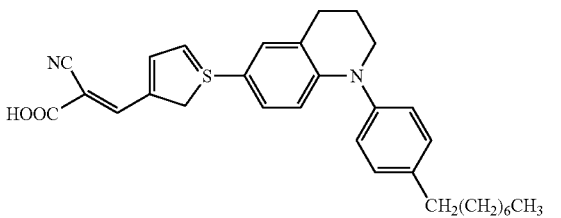
(234)
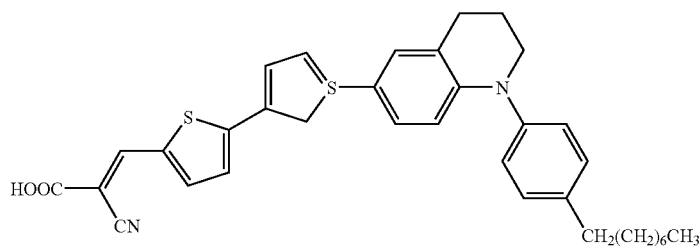
(235)
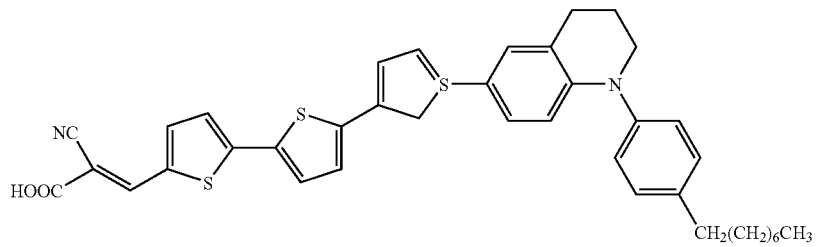
(236)
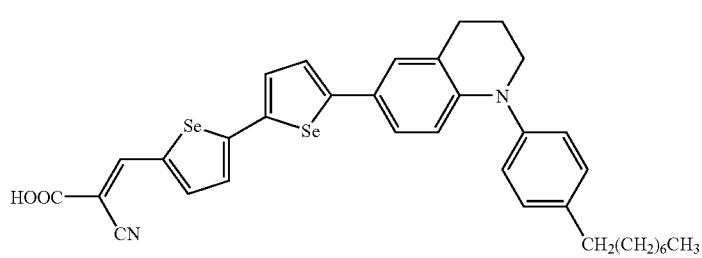
(237)
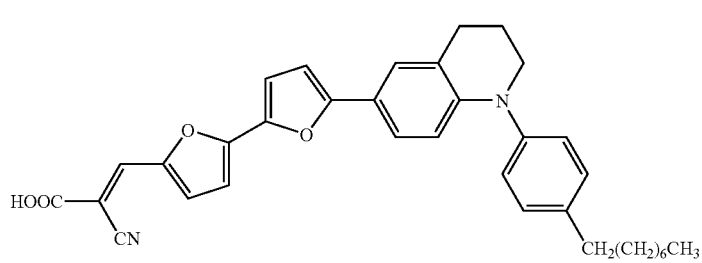

-continued
(238)
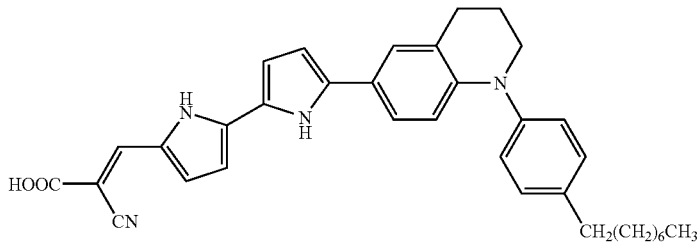
(239)
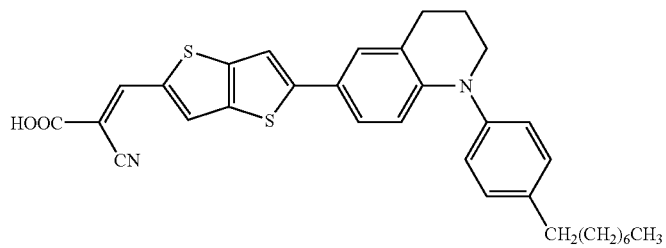
(240)
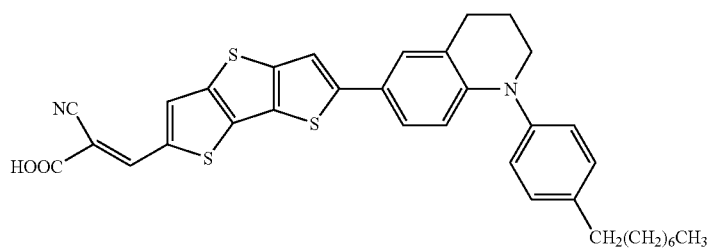
(241)
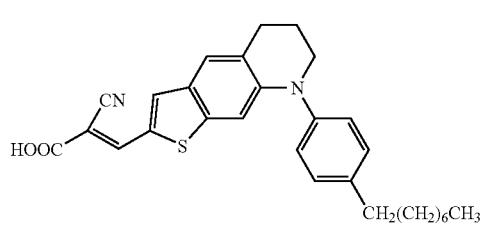
(242)
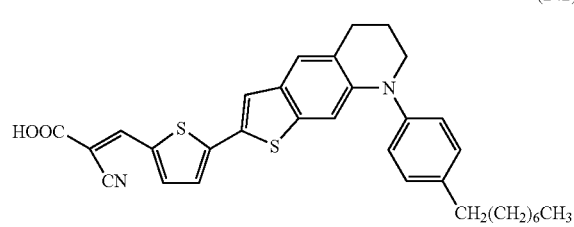
[KA17]
(243)
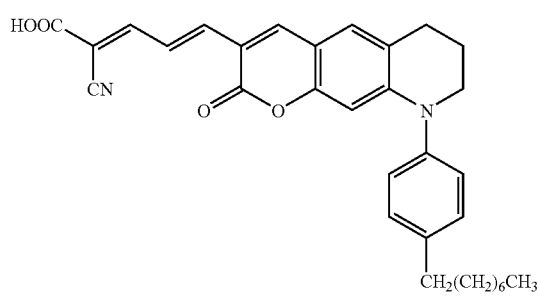
(244)
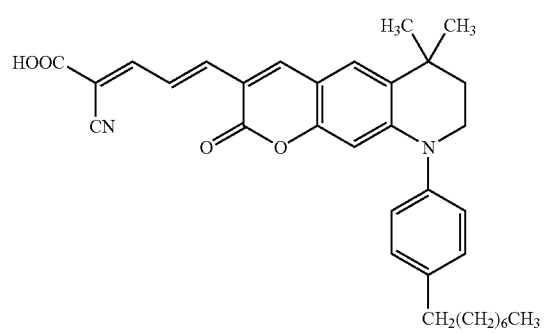

-continued
(245) 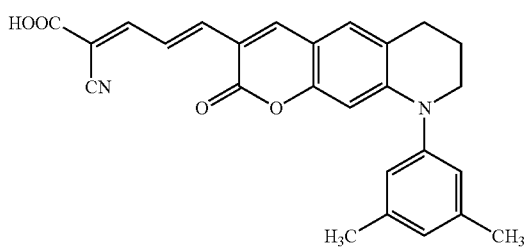
(246) 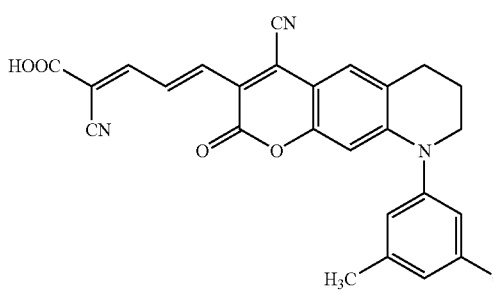
(247) 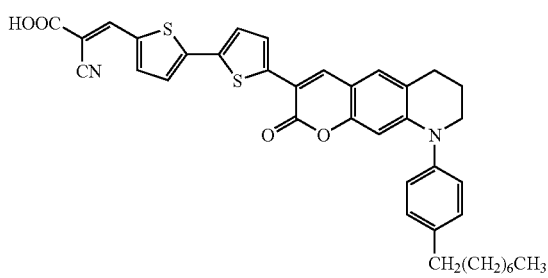
(248) 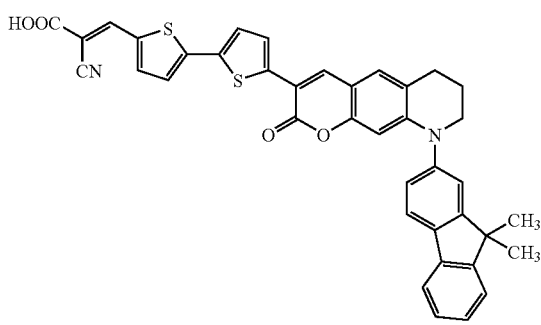
(249) 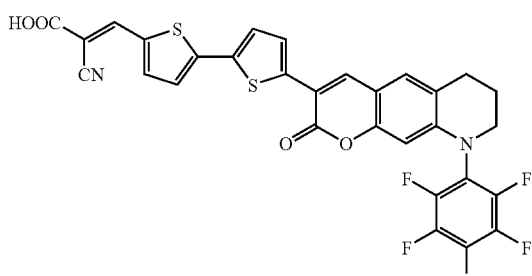
(250) 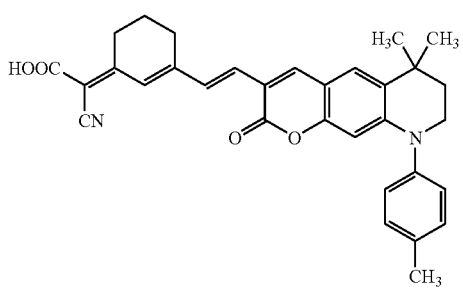
(251) 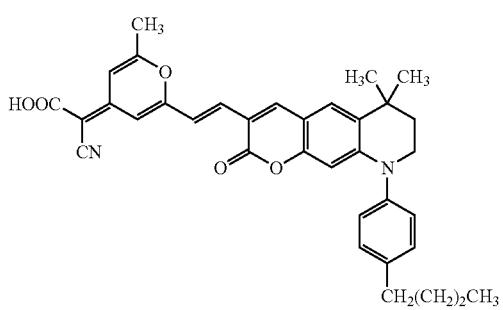
(252)
(253) 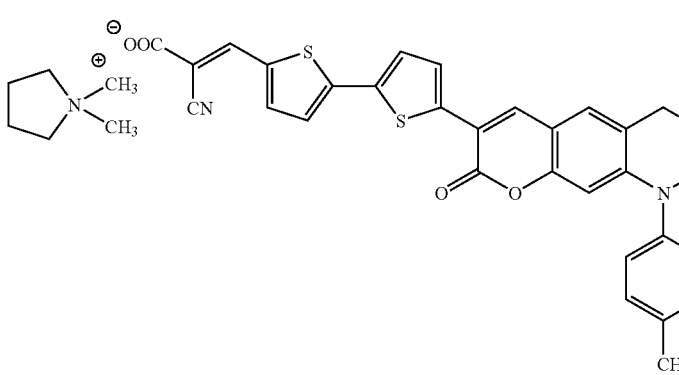

-continued
(254)
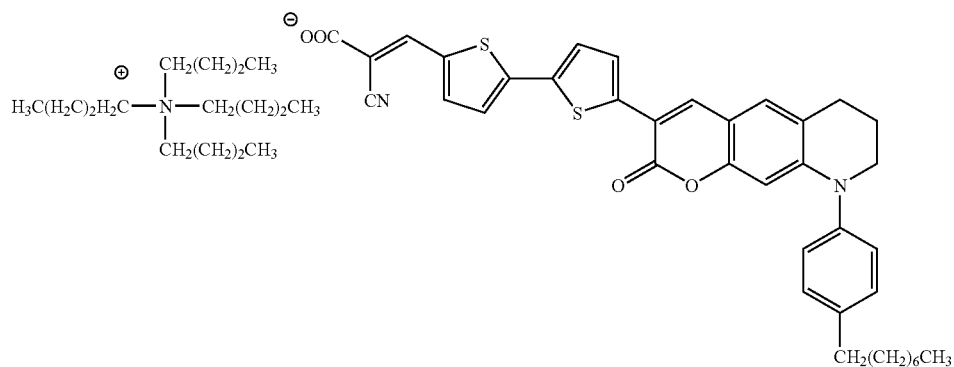
[KA 18]
(255)
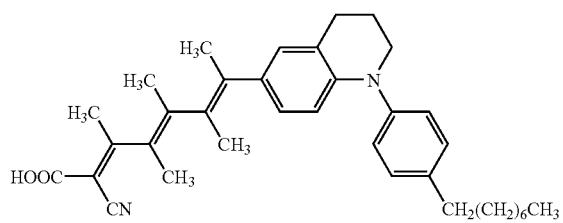
(256)
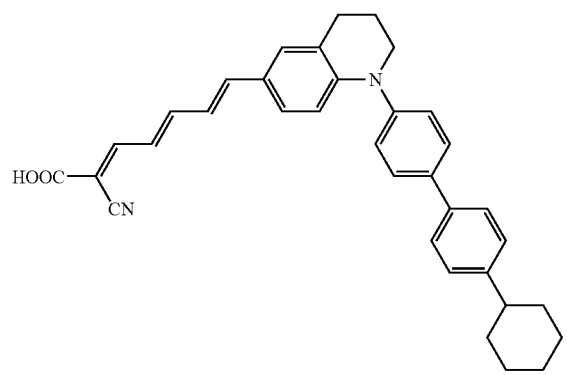
(257)
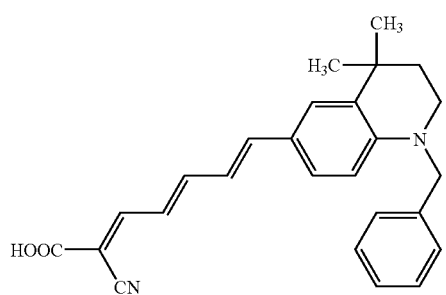
(258)
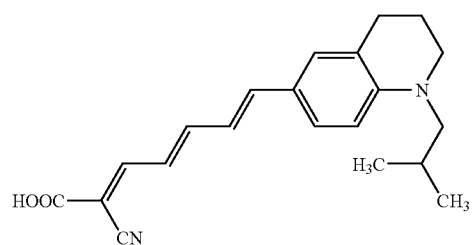
(259)
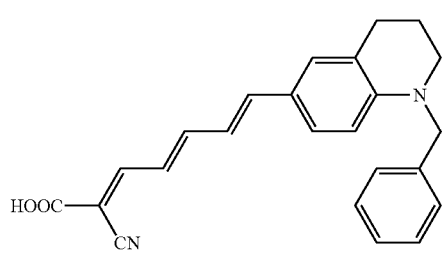
(260)
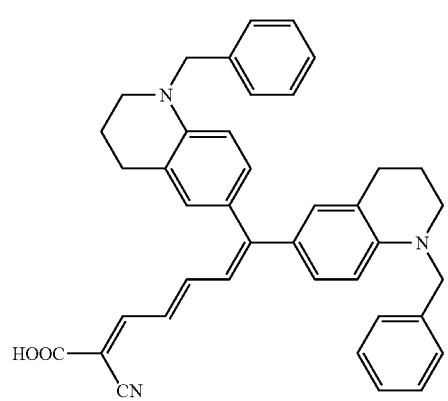

-continued
(261)
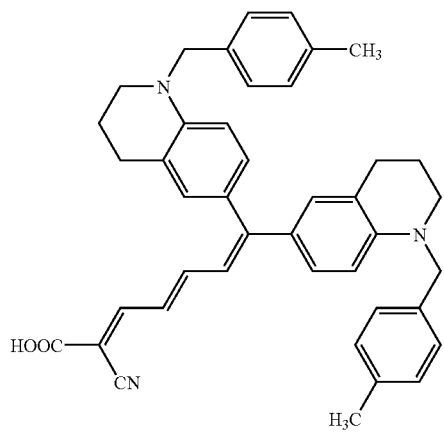
(262)
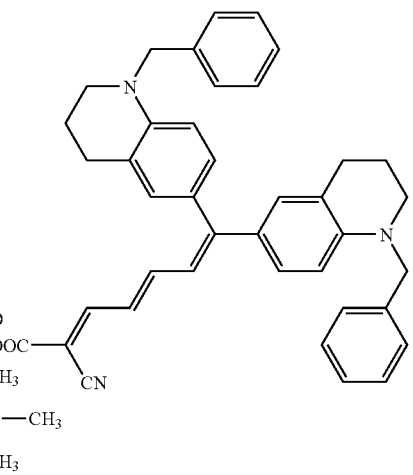
(263)
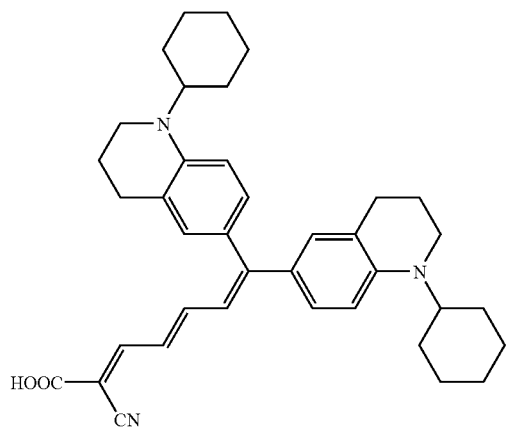
(264)
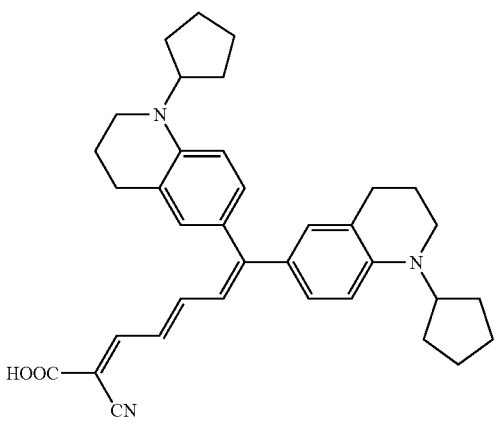
(265)
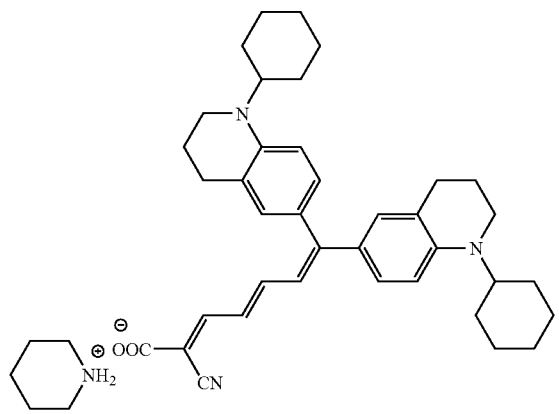
(266)
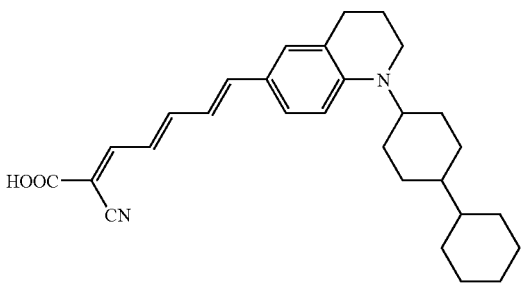
(267)
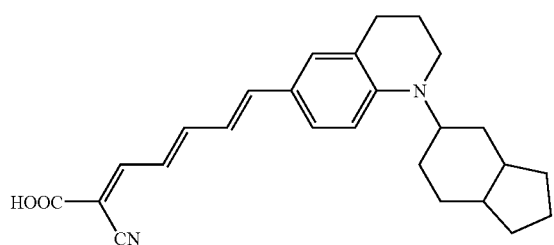
(268)
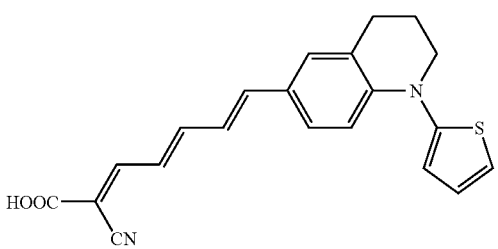

(269)
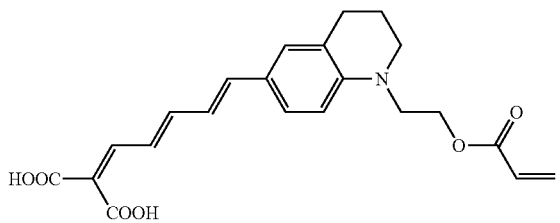
(270)
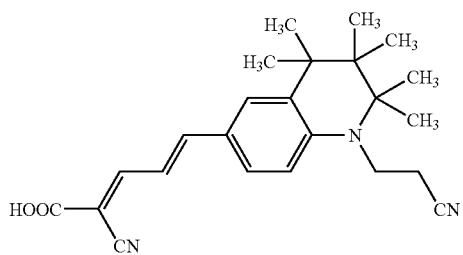
(271)
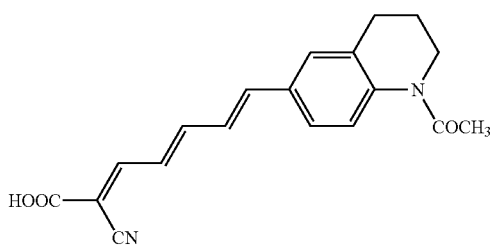
[KA 19]
(272)
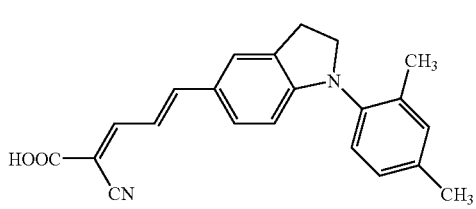
(273)
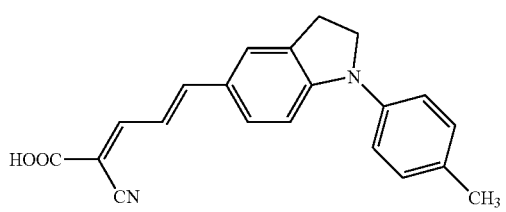
(274)
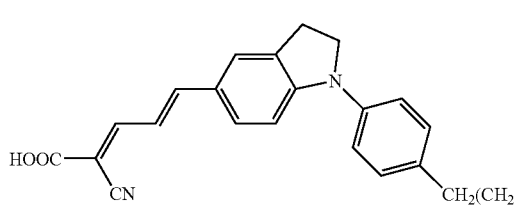
(275)
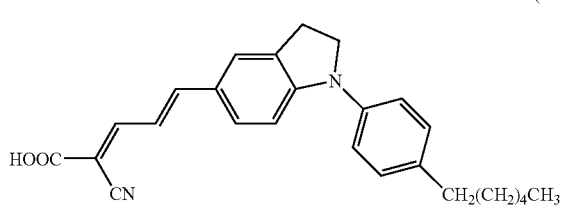
(276)
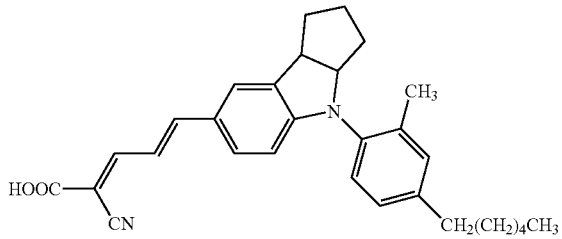
(277)
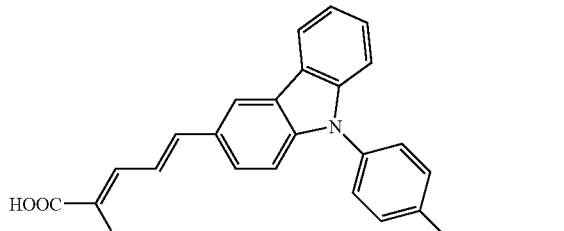
(278)
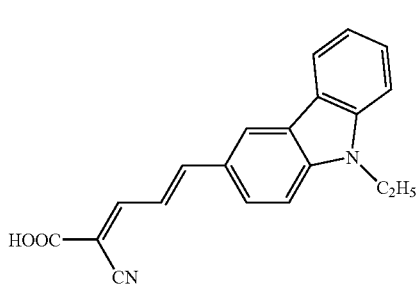
(279)
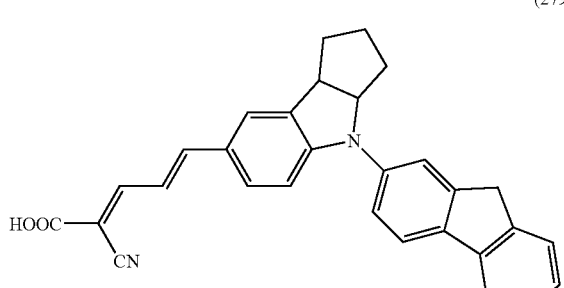

-continued
(280)
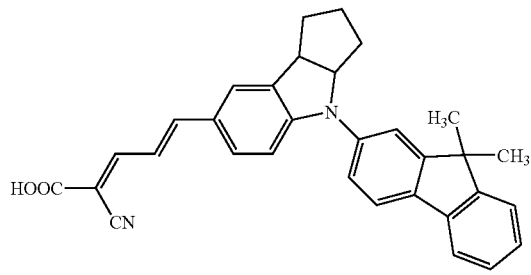
(281)
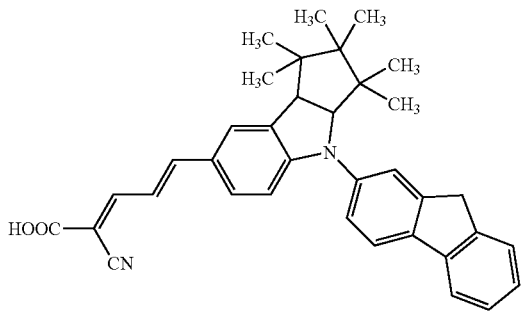
(282)
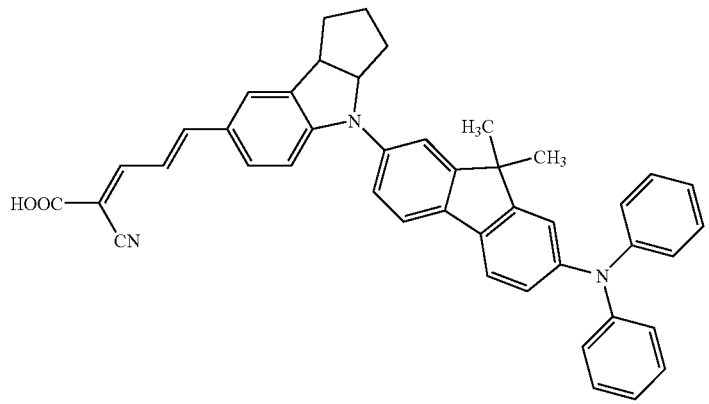
(283)
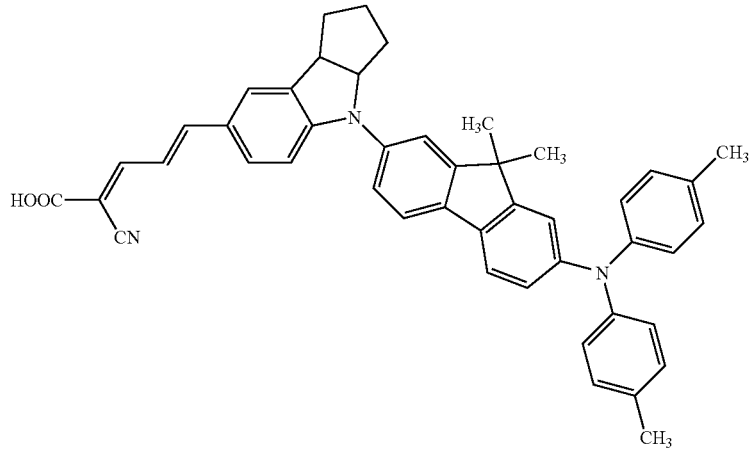
(284)
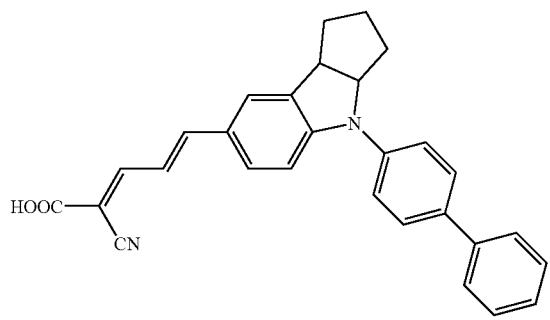
(285)
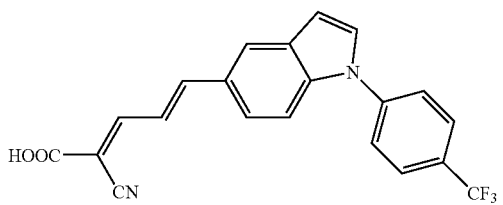

-continued
(286)
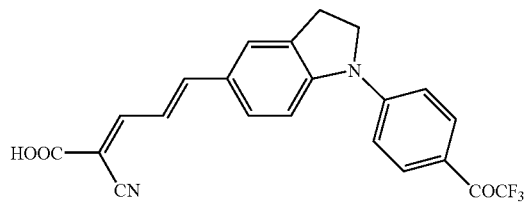
[KA 20]
(287)
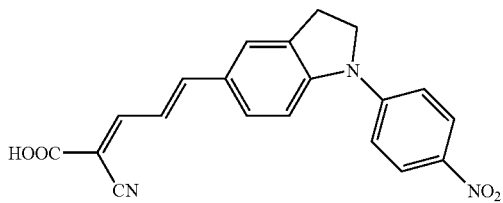
(288)
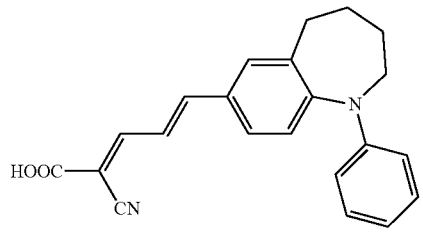
(289)
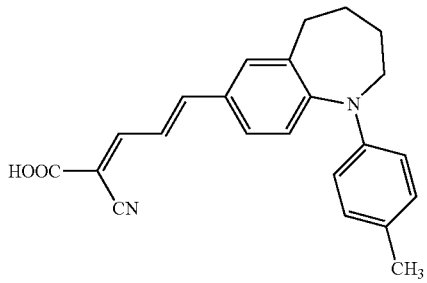
(290)
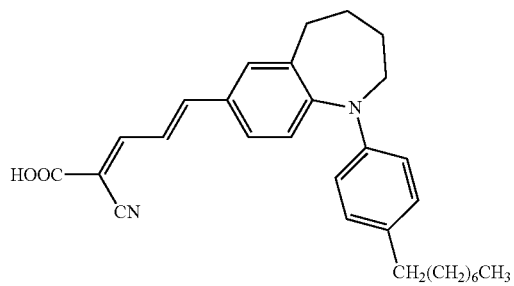
(291)
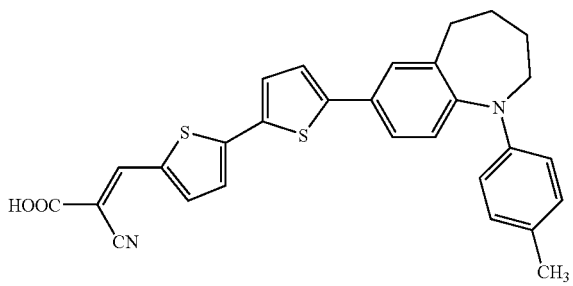
(292)
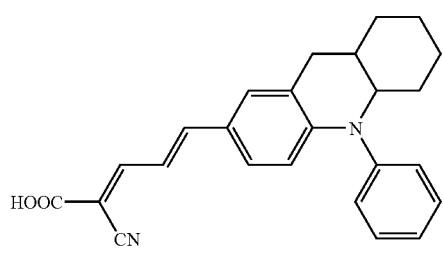
(293)
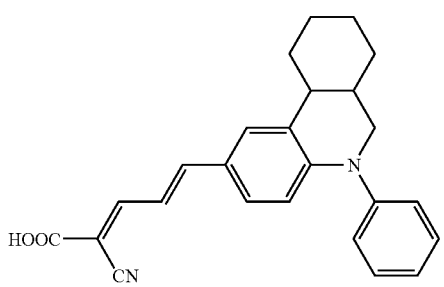
(294)
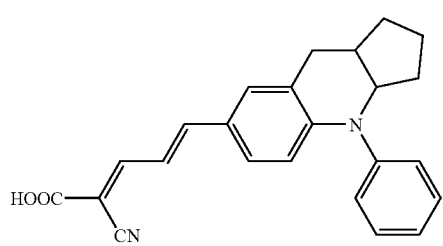
(295)
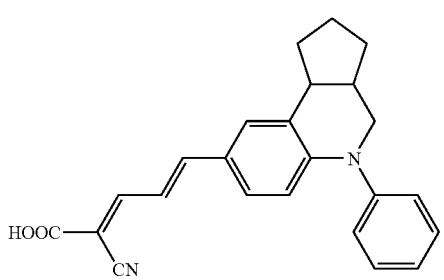

(296)
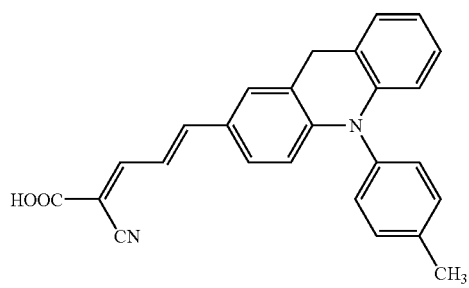
(298)
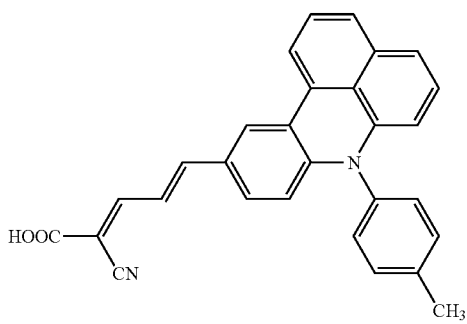
(299)
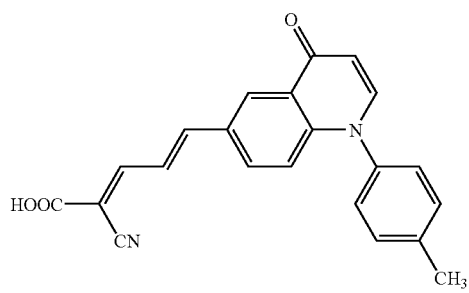
(300)
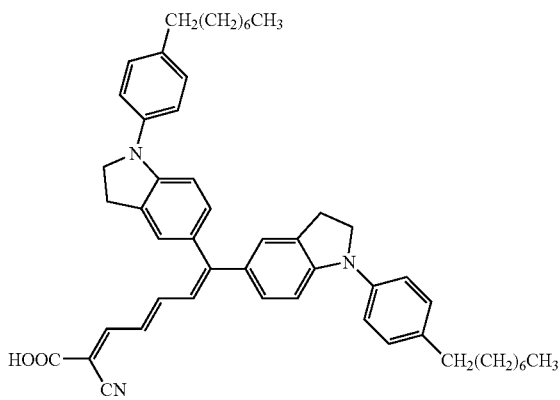
(301)
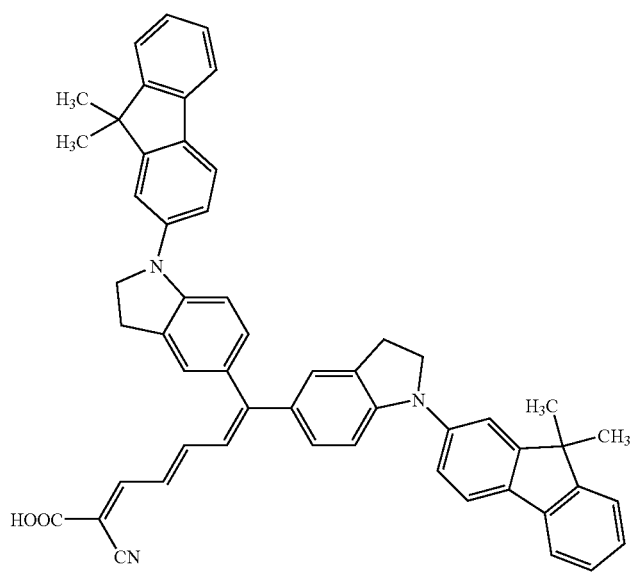

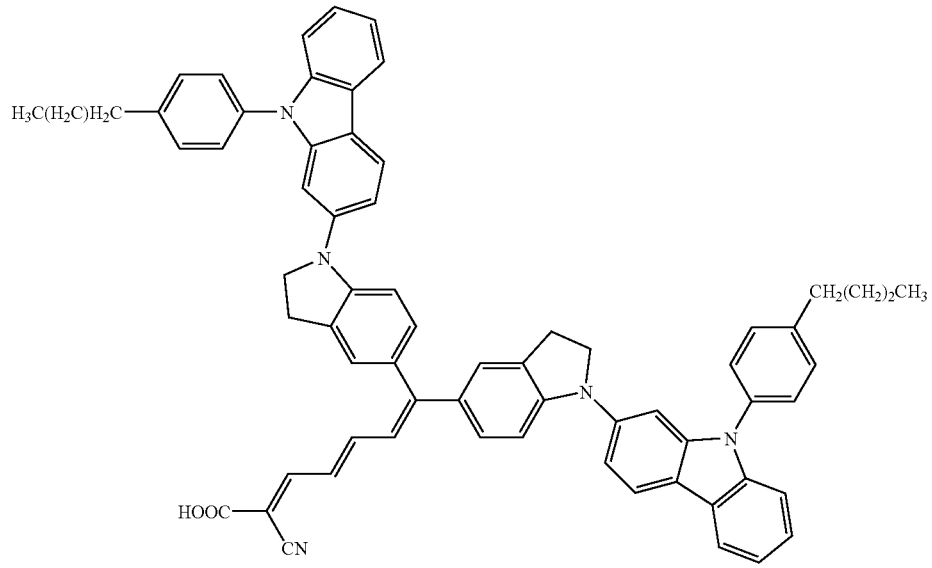
[KA 21]
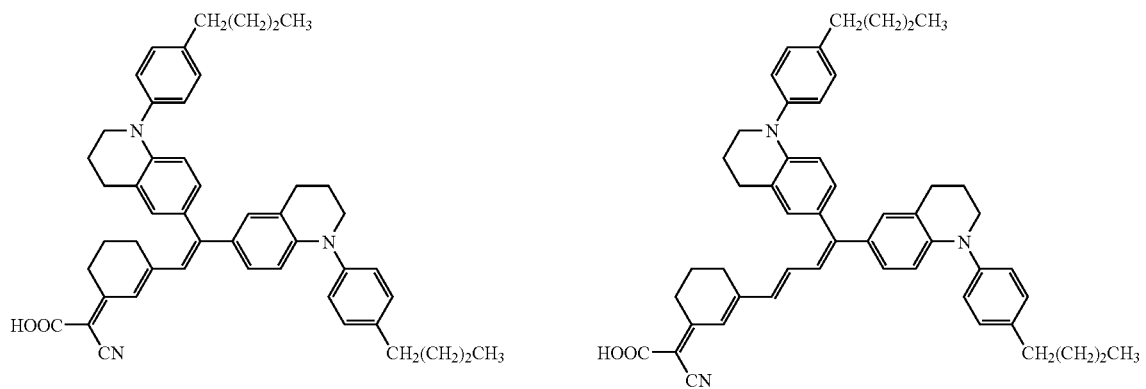
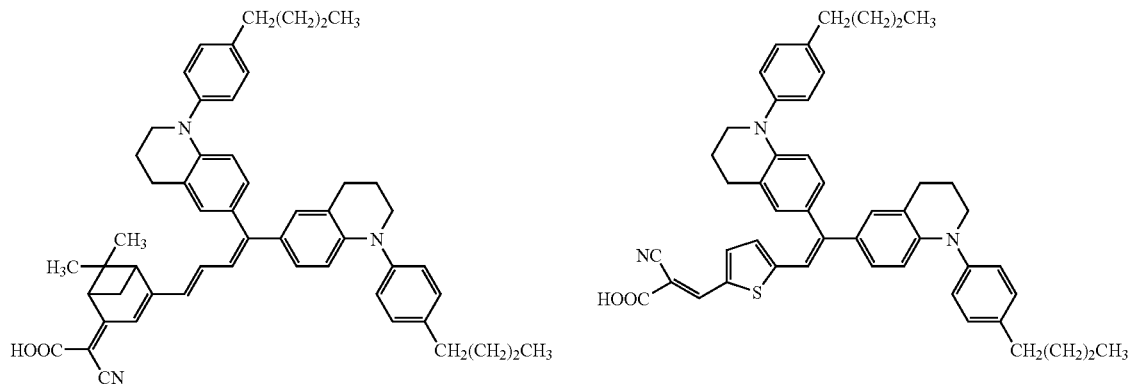

-continued
(307)
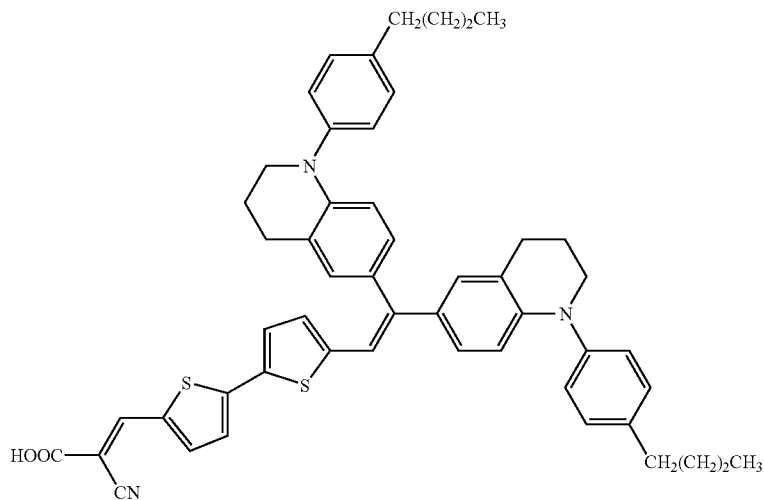
(308)
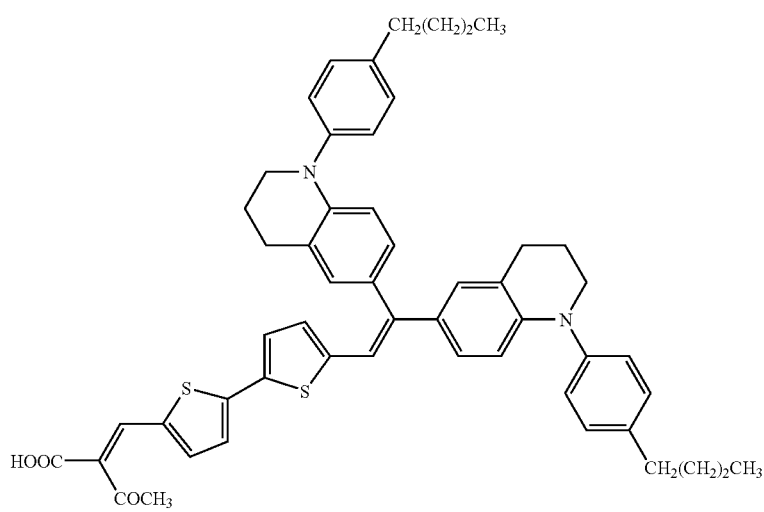
(309)
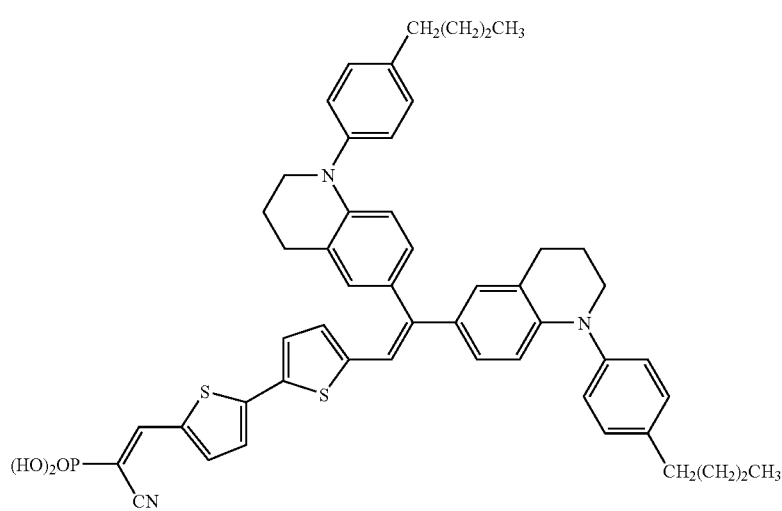

-continued
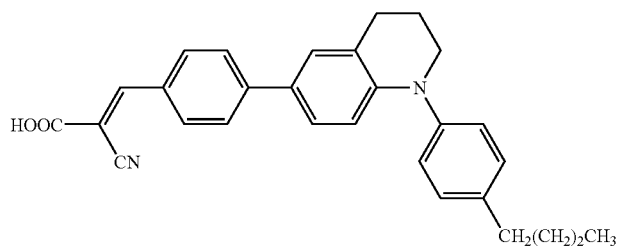
(310)
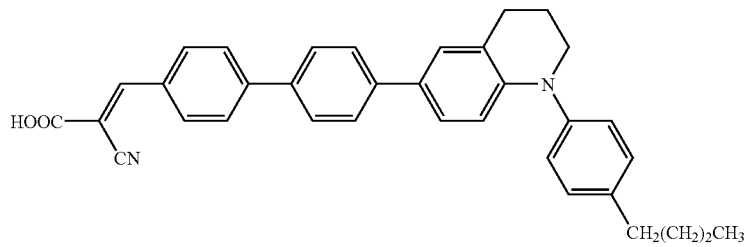
(311)
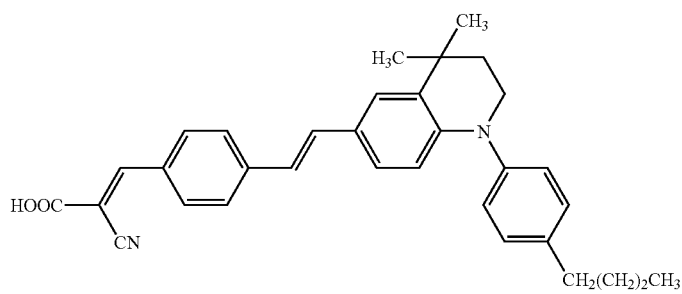
(312)
[KA 22]
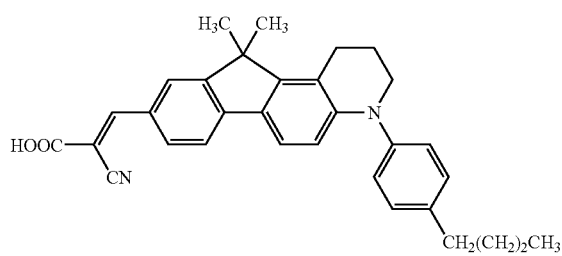
(313)
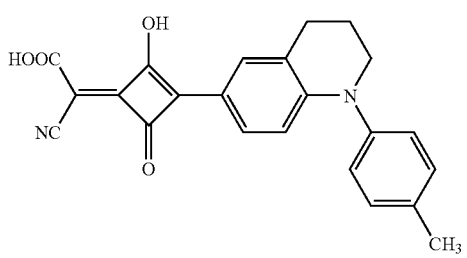
(314)
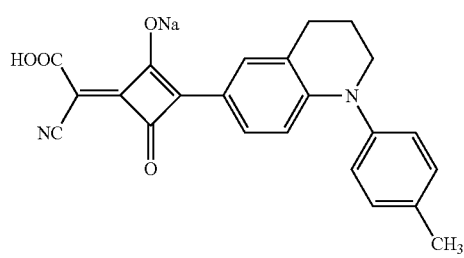
(315)
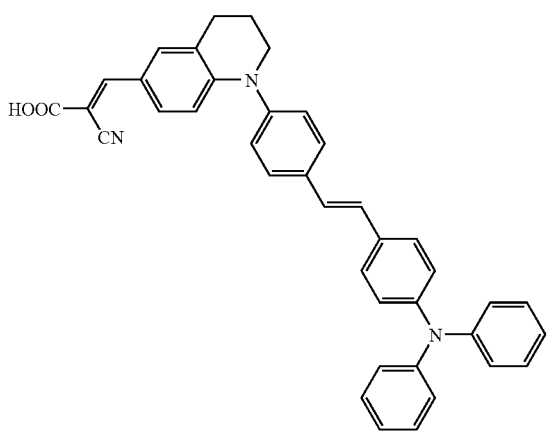
(316)

-continued (317)

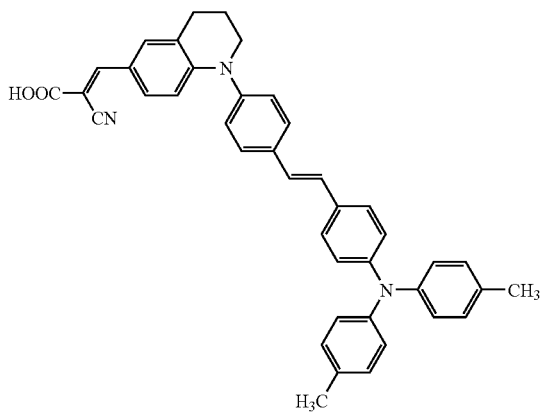

(323)

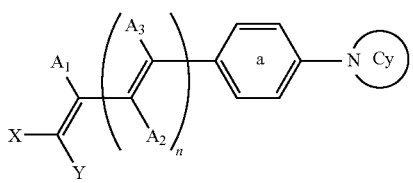

In the above formula (1a), when Z is represented by the formula (2), the methine based dye is represented by the following formula (1b):

[KA 23]

(1b)

(in the formula, n represents an integer of 0 to 7; X and Y represent each independently a hydrogen atom, an optionally substituted aromatic residue, an optionally substituted aliphatic hydrocarbon residue, a carboxyl group, a phosphoric acid group, a sulfonic acid group, a cyano group, an acyl group, an amide group or an alkoxycarbonyl group; in addition, X and Y may combine each other to form an optionally substituted ring; $A_1$, $A_2$ and $A_3$ represent each independently an optionally substituted aromatic residue, an optionally substituted aliphatic hydrocarbon residue, a hydroxyl group, a phosphoric acid group, a cyano group, a hydrogen atom, a halogen atom, a carboxyl group, a carbonamide group, an alkoxycarbonyl group, an arylcarbonyl group or an acyl group; in addition, when n is 2 or more and each of $A_2$ and $A_3$ exist plurally, each of $A_2$ and each of $A_3$ may same or different from each other; in addition, when n is other than 0, a plural number of $A_1$ and/or $A_2$ and/or $A_3$ may form an optionally substituted ring, and further combine together with the benzene ring "a" to form an optionally substituted ring; the benzene ring "a" may have 1 to 4 substituents selected from the group consisting of a halogen atom, an amide group, a hydroxyl group, a cyano group, a nitro group, an alkoxyl group, an acyl group, a substituted or unsubstituted amino group, an optionally substituted aliphatic hydrocarbon residue and an optionally substituted aromatic residue; in addition, when a plural number of substituents exist, these substituents may combine each other or together with $A_1$ and/or $A_2$ and/or $A_3$ as described before to form an optionally substituted ring;
the ring Cy is a 4- to 7-membered ring, and may contain a carbon atom and a hetero atom other than the nitrogen atom described in the formula (1b) as a ring member atom; in addition, the ring may have a substituent, and when Cy has a plural number of substituents, arbitrary substituents thereof may further form a ring). One example of preferable ring Cy group includes a morpholino group.

In the above formula (1b), n represents an integer of 0 to 7, preferably 0 to 6, and particularly preferably 0 to 4.

X and Y are same to those explained in the section of the above formulae (1) to (3a).

Namely, preferably X is a carboxyl group, Y is a cyano group, a carboxyl group or an acyl group, more preferably a cyano group, and when n is 0, this combination is one of preferable combinations.

The case when X and Y combine together to form a ring is further explained. The ring to be formed includes pyrazolone ring, rhodanine ring, bis-rhodanine ring, barbituric ring, pyridone ring, etc. Pyrazolone ring, rhodanine ring and bis-rhodanine ring are preferable, and pyrazolone ring is particularly preferable. Here, n is preferably 0.

$A_1$, $A_2$ and $A_3$ represent each independently an optionally substituted aromatic residue, an optionally substituted aliphatic hydrocarbon residue, a hydroxyl group, a phosphoric acid group, a cyano group, a hydrogen atom, a halogen atom, a carboxyl group, a carbonamide group, an alkoxycarbonyl group, an arylcarbonyl group or an acyl group, and are preferably a hydrogen atom, an optionally substituted aromatic residue, an optionally substituted aliphatic hydrocarbon residue, a cyano group or a halogen atom, and further preferably a hydrogen atom. The optionally substituted aromatic residue, the optionally substituted aliphatic hydrocarbon residue, the halogen atom, the alkoxycarbonyl group, the arylcarbonyl group and the acyl group may be each same to those described in the section of the substituent in "an optionally substituted aromatic residue" and "an optionally substituted aliphatic hydrocarbon residue". In addition, when n is 2 or more and $A_2$ and $A_3$ represent exist plurally, each $A_2$ and each $A_3$ may be same or different from each other.

In addition, when n is other than 0, a plural number of $A_1$ and/or $A_2$ and/or $A_3$ may form an optionally substituted ring, and further combine together with the benzene ring "a" to form an optionally substituted ring. Examples of ring to be formed include an unsaturated hydrocarbon ring or a heterocycle.

Here, examples of the unsaturated hydrocarbon ring include benzene ring, naphthalene ring, anthracene ring, phenanthrene ring, pyrene ring, indene ring, azulene ring, fluorene ring, cyclobutene ring, cyclohexene ring, cyclopentene ring, cyclohexadiene ring, cyclopentadiene ring, etc., and examples of the heterocycle include pyridine ring, pyrazine ring, pyperidine ring, indoline ring, furan ring, thiophen ring, pyran ring, oxazole ring, thiazole ring, thiadiazole ring, oxadiazole ring, indole ring, benzothiazole ring, benzoxazole ring, quinoline ring, carbazole ring, benzopyran ring, etc. In addition, among them, preferable rings include benzene ring, cyclobutene ring, cyclopentene ring, cyclohexene ring, pyran ring, furan ring, thiophen ring, etc. These hydrocarbon rings may have a substituent as described above, and the substituent may be same to those described in the section of the substituent of "an optionally substituted aromatic residue" and "an optionally substituted aliphatic hydrocarbon residue" described above. When the ring to be formed is a heterocycle having a carbonyl group, thiocarbonyl group, etc., a cyclic ketone or a cyclic thioketone may be formed, and these rings may have further substituent. The substituent in such case may be same to those described in the section of the substituent of "an optionally substituted aromatic residue" and "an optionally substituted aliphatic hydrocarbon residue" described above.

The benzene ring "a" may have 1 to 4 substituents selected from the group consisting of a halogen atom, an amide group, a hydroxyl group, a cyano group, a nitro group, an alkoxyl group, an acyl group, a substituted or unsubstituted amino group, an optionally substituted aliphatic hydrocarbon residue and an optionally substituted aromatic residue. The halogen atom, the amide group, the alkoxyl group, the acyl group, the substituted or unsubstituted amino group, the optionally substituted aliphatic hydrocarbon residue and the optionally substituted aromatic residue may each be same to those described in the section of the substituent of "an optionally substituted aromatic residue" and "an optionally substituted aliphatic hydrocarbon residue". In addition, when a plural number of substituents exist, these substituents may combine each other or together with $A_1$ and/or $A_2$ and/or $A_3$ as described before to form an optionally substituted ring. Here, the substituent of an optionally substituted ring may be same to those described in the section of the substituent of "an optionally substituted aromatic residue" and "an optionally substituted aliphatic hydrocarbon residue".

The ring Cy in the formula (1b) is a 4- to 7-membered ring, and the ring member atom thereof may include a hetero atom in addition to a carbon atom and a nitrogen atom described in the formula (1b). In addition, the ring may have a substituent, and when Cy has a plural number of substituents, arbitrary substituents may further form a ring. Specific examples of the ring Cy include the followings, which may further have a substituent. The substituent includes those described in the section of the substituent in "an optionally substituted aromatic residue" and "an optionally substituted aliphatic hydrocarbon residue".

[KA 24]

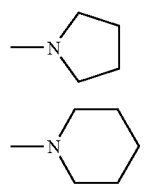

(3)

(4)

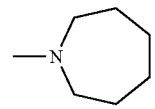

(5)

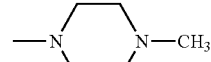

(6)

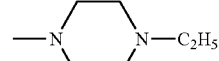

(7)

(8)

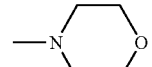

(9)

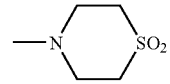

(10)

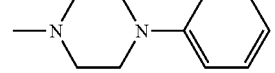

(11)

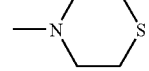

(12)

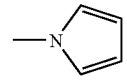

(13)

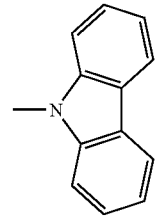

(14)

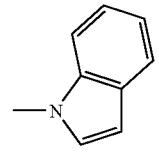

(15)

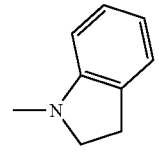

(16)

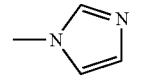

(17)

(18)

-continued

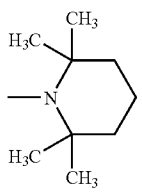
(19)

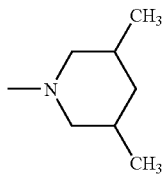
(20)

Among the methine based dyes represented by the formula (1b), a methine based dye represented by the following formula (2b) is preferable.

[KA 25]

(2b)

In the formula (2b), n, X, Y, $A_1, A_2, A_3$ and benzene ring "a" may be each same as in the formula (1b). Specific examples of n, X and Y are same as in the above formula (1b).

For example, one of preferable combinations of X and Y is preferably a case when X is a carboxyl group and Y is a cyano group, a carboxyl group or an acyl group, and more preferably Y is a cyano group. In addition, another preferable combination is a case when X and Y combine together to form a ring, and said ring to be formed is a pyrazolone ring, and the methine group represented by X(Y)=C is a 2-phenyl-5-carboxy-3-pyrazolone-4-yl group.

In these preferable combinations, n is preferably 0. In the group represented by the above formula (2b), the ring Cy is preferably a 6-membered ring containing an oxygen atom or a sulfur atom besides the nitrogen atom shown in the formula (2b), and the ring Cy group is more preferably a morpholino group. In this more preferable compound, $A_1$ may be same as in the formula (1b), and more preferably a hydrogen atom.

$R_{1b}$ to $R_{8b}$ represent each independently a hydrogen atom, an optionally substituted aliphatic hydrocarbon residue, an optionally substituted aromatic hydrocarbon residue, a halogen atom or a hydroxyl group, and are preferably a hydrogen atom or an optionally substituted aliphatic hydrocarbon residue. The optionally substituted aliphatic hydrocarbon residue and the optionally substituted aromatic hydrocarbon residue may be same to those described in the section of "an optionally substituted aliphatic hydrocarbon residue" and "an optionally substituted aromatic hydrocarbon residue". The halogen atom may be same to those described in the section of the substituent of "an optionally substituted aliphatic hydrocarbon residue" and "an optionally substituted aromatic residue". In addition, $R_{1b}$ to $R_{4b}$ and $R_{5b}$ to $R_{8b}$ may each combine together to form an optionally substituted ring. The substituent in the optionally substituted ring may be same to those described in the section of the substituent of "an optionally substituted aliphatic hydrocarbon residue" and "an optionally substituted aromatic residue". Preferably $R_{1b}$ to $R_{8b}$ are each independently a hydrogen atom or an alkyl group having 1 to 4 carbon atoms, and particularly preferably $R_{1b}, R_{2b}, R_{7b}$ and $R_{8b}$ are each a methyl group, and $R_{3b}, R_{4b}, R_{5b}$ and $R_{6b}$ are each a hydrogen atom.

Q in the formula (2b) represents each $CR_9R_{10}$, $NR_{11}$, an oxygen atom, a sulfur atom, a selenium atom or $SO_2$, and is preferably $CR_9R_{10}$, an oxygen atom, or $SO_2$, and particularly preferably $CR_9R_{10}$ or an oxygen atom. $R_9$ and $R_{10}$ is each independently a hydrogen atom or a substituent, and the substituent include those described in the section of the substituent of "an optionally substituted aliphatic hydrocarbon residue" and "an optionally substituted aromatic residue". $R_{11}$ includes a hydrogen atom, an optionally substituted aliphatic hydrocarbon residue, an optionally substituted aromatic hydrocarbon residue, an acyl group, etc., and is preferably a hydrogen atom, an optionally substituted aliphatic hydrocarbon residue or an optionally substituted aromatic hydrocarbon residue, and particularly preferably an optionally substituted aliphatic hydrocarbon residue. The optionally substituted aliphatic hydrocarbon residue and the optionally substituted aromatic hydrocarbon residue may be same to those described in the section of "an optionally substituted aliphatic hydrocarbon residue" and "an optionally substituted aromatic residue". The acyl group may be same to those described in the sections of X and Y in the formula (1b). $R_9$ and $R_{10}$ are each preferably a hydrogen atom or an alkyl group having 1 to 4 carbon atoms, and particularly preferably a hydrogen atom or a methyl group. $R_{11}$ is preferably a hydrogen atom, an alkyl group having 1 to 4 carbon atoms, or a phenyl group, and particularly preferably a hydrogen atom, a methyl group or a phenyl group.

In addition, when the methine based dyes represented by the above formula (1), (1a) or (1b), or the above formula (2b) or the like have an acidic group such as a carboxyl group, a phosphoric acid group, a hydroxyl group and a sulfonic acid group, etc. as a substituent, these dyes may each form a salt thereof, and the salt includes, for example, a salt with an alkali metal or an alkaline earth metal such as lithium, sodium, potassium, magnesium, calcium, etc., and a salt with an organic base, for example, a quaternary ammonium such as tetramethylammonium, tetrabutylammonium, pyridinium, imidazolium, pyperazinium, pyperidinium, etc., and the like.

The compound represented by the above formula (1b) or the above formula (2b) can take a form of structural isomer such as cis body, trans body, racemic form, etc., but the form of the compound is not particularly limited, and any isomer and a mixture thereof can be suitably used for the photosensitizing dye in the present invention.

The methine based dye represented by the above formula (1b) can be manufactured, for example, by the reaction scheme shown below. The methine based dye represented by the formula (1b) of the present invention can be obtained by the known process, namely, by condensing a compound having an active methylene represented by the formula (22) and a carbonyl compound represented by the formula (21) in the presence of a basic catalyst such as sodium hydroxide, sodium methylate, sodium acetate, diethylamine, triethylamine, pyperidine, pyperazine, diazabicycloundecene, etc., if necessary, in a solvent, for example, alcohols such as methanol, ethanol, isopropanol, butanol, etc., aprotic polar solvents such as dimethylformamide, N-methylpyrolidone, etc., toluene, acetic anhydride, acetonitrile, etc., at 20° C. to 180° C., preferably at 50° C. to 150° C.

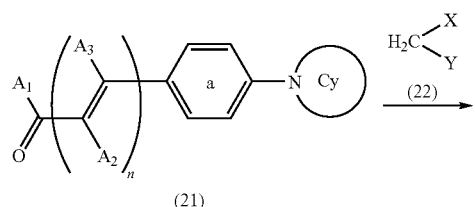

(21)

[KA 26]

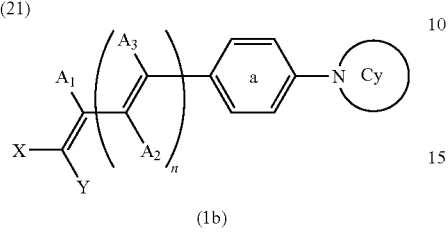

(22)

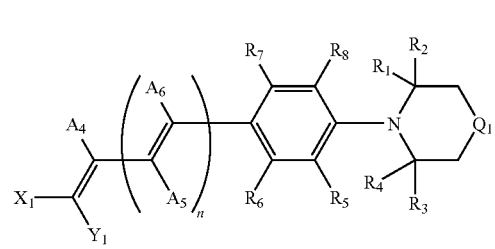

(1b)

examples of the methine based dye represented by the following formula (23) are shown in Table 5 and Table 6. In each Table, Ph means a phenyl group. In addition, following them, examples of compounds other than those in Table 5 and Table 6 are listed up with structural formulae thereof.

[KA 27]

(23)

Hereinafter, specific examples of the methine based dye represented by the formula (1b) are listed up. Firstly, specific

TABLE 5

| Compound | n | $X_1$ | $Y_1$ | $A_4$ | $A_5$ | $A_6$ | $R_1$ | $R_2$ | $R_3$ | $R_4$ | $R_5$ | $R_6$ | $R_7$ | $R_8$ | $Q_1$ |
|---|---|---|---|---|---|---|---|---|---|---|---|---|---|---|---|
| 1 | 0 | H | H | H | — | — | H | H | H | H | H | H | H | H | $CH_2$ |
| 2 | 0 | COOH | CN | H | — | — | H | H | H | H | H | H | H | H | $CH_2$ |
| 3 | 0 | COOH | CN | H | — | — | $CH_3$ | $CH_3$ | $CH_3$ | $CH_3$ | H | H | H | H | $CH_2$ |
| 4 | 0 | COOH | CN | H | — | — | H | H | H | H | H | H | H | H | $C(CH_3)_2$ |
| 5 | 0 | COOH | CN | H | — | — | H | H | H | H | H | H | H | H | $C(Ph)_2$ |
| 6 | 0 | COOH | CN | H | — | — | H | H | H | H | H | H | H | H | O |
| 7 | 0 | COOH | CN | H | — | — | H | H | H | H | H | H | H | H | $SO_2$ |
| 8 | 0 | COOH | COOH | H | — | — | H | H | H | H | H | H | H | H | O |
| 9 | 0 | COOH | $COCH_3$ | H | — | — | H | H | H | H | H | H | H | H | S |
| 10 | 0 | COOH | $COCF_3$ | H | — | — | H | H | H | H | H | H | H | H | O |
| 11 | 0 | $PO(OH)_2$ | CN | H | — | — | H | H | H | H | H | H | H | H | $SO_2$ |
| 12 | 0 | $SO_3H$ | CN | H | — | — | H | H | H | H | H | H | H | H | O |
| 13 | 0 | $COOCH_3$ | CN | H | — | — | H | H | H | H | H | H | H | H | O |
| 14 | 0 | COOLi | CN | H | — | — | H | H | H | H | H | H | H | H | O |
| 15 | 0 | COONa | CN | H | — | — | H | H | H | H | H | H | H | H | O |
| 16 | 0 | COOK | CN | H | — | — | H | H | H | H | H | H | H | H | O |
| 17 | 0 | COOH | $PO(OH)_2$ | H | — | — | H | H | H | H | H | H | H | H | NH |
| 18 | 0 | $PO(OH)_2$ | $PO(OH)_2$ | H | — | — | H | H | H | H | H | H | H | H | $NCH_3$ |
| 19 | 0 | COOH | $NO_2$ | H | — | — | H | H | H | H | H | H | H | H | O |
| 20 | 0 | COOH | Cl | H | — | — | H | H | H | H | H | H | H | H | O |
| 21 | 0 | COOH | CN | H | — | — | H | H | H | H | H | $CH_3$ | H | H | O |
| 22 | 0 | COOH | CN | H | — | — | H | H | H | H | H | $CH_3$ | H | $CH_3$ | O |
| 23 | 0 | COOH | CN | H | — | — | H | H | H | H | H | $OCH_3$ | H | $CH_3$ | O |
| 24 | 0 | COOH | CN | H | — | — | H | H | H | H | Cl | H | H | H | O |
| 25 | 0 | COOH | CN | H | — | — | H | H | H | H | H | $NHCOCH_3$ | H | $OCH_3$ | O |
| 26 | 0 | COOH | COPh | H | — | — | H | H | H | H | H | H | H | H | O |
| 27 | 0 | COOH | $COC(CH_3)_3$ | H | — | — | H | H | H | H | H | H | H | H | O |
| 28 | 0 | COOH | $SO_2CF_3$ | H | — | — | H | H | H | H | H | H | H | H | O |
| 29 | 0 | COONa | COONa | H | — | — | H | H | H | H | H | H | H | H | O |
| 30 | 0 | COOH | CN | $CH_3$ | — | — | H | H | H | H | H | H | H | H | O |
| 31 | 0 | COOH | CN | Ph | — | — | H | H | H | H | H | H | H | H | O |
| 32 | 1 | COOH | COOH | H | H | H | H | H | H | H | H | H | H | H | O |
| 33 | 1 | COOH | CN | H | H | H | H | H | H | H | H | H | H | H | $SO_2$ |
| 34 | 1 | COOH | CN | H | $CH_3$ | $CH_3$ | H | H | H | H | H | H | H | H | O |
| 35 | 1 | COOH | CN | H | H | $CH_3$ | H | H | H | H | H | H | H | H | O |
| 36 | 1 | COOH | CN | H | $CH_3$ | H | H | H | H | H | H | H | H | H | O |
| 37 | 1 | COOH | CN | $CH_3$ | $CH_3$ | $CH_3$ | H | H | H | H | H | H | H | H | O |
| 38 | 1 | COOH | CN | H | H | Ph | H | H | H | H | H | H | H | H | O |
| 39 | 1 | COOH | CN | H | H | H | H | H | H | H | H | $CH_3$ | H | H | O |
| 40 | 1 | COOH | CN | H | H | H | H | H | H | H | H | $CH_3$ | H | H | $SO_2$ |
| 41 | 1 | COOH | CN | H | H | H | H | H | H | H | H | H | H | H | $NCH_3$ |
| 42 | 1 | COOH | Ph | H | H | H | H | H | H | H | H | H | H | H | O |
| 43 | 1 | COOH | $CH_2CH_3$ | H | H | H | H | H | H | H | H | H | H | H | O |
| 44 | 1 | $PO(ONa)2$ | CN | H | H | H | H | H | H | H | H | $n\text{-}C_4H_8$ | H | H | O |
| 45 | 1 | COOH | CN | H | H | H | Cl | Cl | Cl | Cl | H | H | H | H | O |
| 48 | 1 | COOH | CN | H | H | H | $CH_3$ | $CH_3$ | $CH_3$ | $CH_3$ | H | H | H | H | S |
| 47 | 1 | COOH | CN | H | H | H | $CH_3$ | $CH_3$ | $CH_3$ | $CH_3$ | H | H | H | H | O |
| 48 | 1 | COOH | CN | H | H | H | $CH_3$ | $CH_3$ | $CH_3$ | $CH_3$ | H | H | H | H | $SO_2$ |

TABLE 6

| Compound | n | $X_1$ | $Y_1$ | $A_4$ | $A_5$ | $A_6$ | $R_1$ | $R_2$ | $R_3$ | $R_4$ | $R_5$ | $R_6$ | $R_7$ | $R_8$ | $Q_1$ |
|---|---|---|---|---|---|---|---|---|---|---|---|---|---|---|---|
| 49 | 1 | COOH | CN | H | H | H | H | H | H | H | $CH_3$ | $CH_3$ | $CH_3$ | $CH_3$ | O |
| 50 | 1 | COOH | CN | H | H | H | H | H | H | H | $CH_3$ | $CH_3$ | $CH_3$ | $CH_3$ | O |
| 51 | 1 | COOH | CN | H | H | H | H | H | H | H | F | F | F | F | O |
| 52 | 1 | COOH | CN | H | H | H | H | H | H | H | Cl | Cl | Cl | Cl | O |
| 53 | 1 | COOH | CN | $CH_3$ | $CH_3$ | $CH_3$ | H | H | H | H | $CH_3$ | $CH_3$ | $CH_3$ | $CH_3$ | O |
| 54 | 1 | COOH | CN | $CH_3$ | $CH_3$ | $CH_3$ | $CH_3$ | $CH_3$ | $CH_3$ | $CH_3$ | $CH_3$ | $CH_3$ | $CH_3$ | $CH_3$ | $NCH_3$ |
| 55 | 1 | COOH | CN | Cl | Cl | Cl | H | H | H | H | H | H | H | H | O |
| 56 | 1 | COOH | CN | H | H | H | H | H | H | H | $NH_2$ | H | H | H | O |
| 57 | 1 | COOH | CN | H | H | H | H | H | H | H | H | NHPh | H | H | O |
| 58 | 2 | COOH | CN | H | H | H | H | H | H | H | H | H | H | H | O |
| 59 | 2 | COOH | CN | H | H | H | H | H | H | H | H | H | H | H | S |
| 60 | 2 | COOH | CN | H | H | H | H | H | H | H | H | H | H | H | NH |
| 61 | 2 | COOH | CN | H | H | H | H | H | H | H | H | H | H | H | $SO_2$ |
| 62 | 2 | COOH | CN | H | H | H | H | H | H | H | H | H | H | H | $C(CH_3)_2$ |
| 63 | 2 | COOH | $COCF_3$ | H | H | H | H | H | H | H | H | H | H | H | O |
| 64 | 2 | COOH | $COCH_3$ | H | H | H | H | H | H | H | H | H | H | H | O |
| 65 | 2 | COOH | $CF_3$ | H | H | H | H | H | H | H | H | H | H | H | O |
| 66 | 2 | COOH | $NO_2$ | H | H | H | H | H | H | H | H | H | H | H | O |
| 67 | 2 | COOH | $SO_2Ph$ | H | H | H | H | H | H | H | H | H | H | H | O |
| 68 | 3 | COOH | CN | H | H | H | H | H | H | H | H | H | H | H | O |
| 69 | 3 | COOH | CN | H | H | H | H | H | H | H | H | H | H | H | S |
| 70 | 3 | COOH | CN | H | H | H | H | H | H | H | H | H | H | H | NH |
| 71 | 3 | COOH | CN | H | H | H | H | H | H | H | H | H | H | H | $SO_2$ |
| 72 | 3 | COOH | CN | H | H | H | H | H | H | H | H | H | H | H | $C(CH_3)_2$ |
| 73 | 3 | COOH | $COCF_3$ | H | H | H | H | H | H | H | H | H | H | H | O |
| 74 | 3 | COOH | $COCH_3$ | H | H | H | H | H | H | H | H | H | H | H | O |
| 75 | 3 | COOH | $CF_3$ | H | H | H | H | H | H | H | H | H | H | H | O |
| 76 | 3 | COOH | $NO_2$ | H | H | H | H | H | H | H | H | H | H | H | O |
| 77 | 3 | COOH | $SO_2Ph$ | H | H | H | H | H | H | H | H | H | H | H | O |
| 78 | 4 | COOH | CN | H | H | H | H | H | H | H | H | H | H | H | O |
| 79 | 4 | COOH | CN | H | H | H | H | H | H | H | H | H | H | H | S |
| 80 | 4 | COOH | CN | H | H | H | H | H | H | H | H | H | H | H | NH |
| 81 | 4 | COOH | CN | H | H | H | H | H | H | H | H | H | H | H | $SO_2$ |
| 82 | 4 | COOH | CN | H | H | H | H | H | H | H | H | H | H | H | $C(CH_3)_2$ |
| 83 | 4 | COOH | $COCF_3$ | H | H | H | H | H | H | H | H | H | H | H | O |
| 84 | 4 | COOH | $COCH_3$ | H | H | H | H | H | H | H | H | H | H | H | O |
| 85 | 4 | COOH | $CF_3$ | H | H | H | H | H | H | H | H | H | H | H | O |
| 86 | 4 | COOH | $NO_2$ | H | H | H | H | H | H | H | H | H | H | H | O |
| 87 | 4 | COOH | $SO_2Ph$ | H | H | H | H | H | H | H | H | H | H | H | O |
| 88 | 5 | COOH | CN | H | H | H | H | H | H | H | H | H | H | H | O |
| 89 | 5 | COOH | CN | H | H | H | H | H | H | H | H | H | H | H | $SO_2$ |
| 90 | 5 | COOH | CN | H | H | H | H | H | H | H | H | H | H | H | $C(CH_3)_2$ |
| 91 | 6 | COOH | CN | H | H | H | H | H | H | H | H | H | H | H | O |
| 92 | 6 | COOH | CN | H | H | H | H | H | H | H | H | H | H | H | $SO_2$ |
| 93 | 6 | COOH | CN | H | H | H | H | H | H | H | H | H | H | H | $C(CH_3)_2$ |
| 94 | 7 | COOH | CN | H | H | H | H | H | H | H | H | H | H | H | O |
| 95 | 7 | COOH | CN | H | H | H | H | H | H | H | H | H | H | H | $SO_2$ |
| 96 | 7 | COOH | CN | H | H | H | H | H | H | H | H | H | H | H | $C(CH_3)_2$ |

[KA 28]

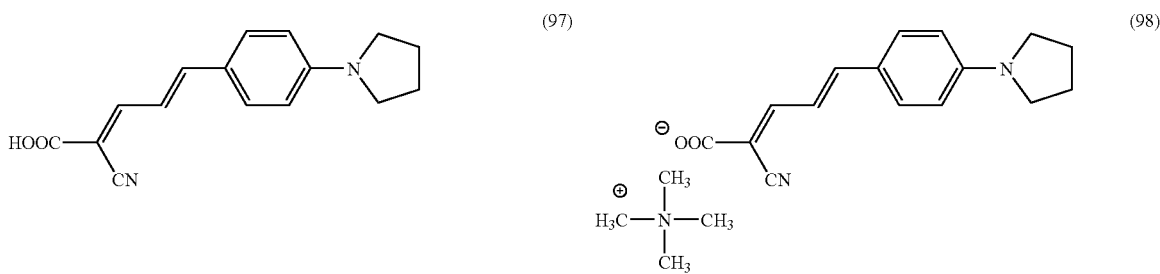

-continued
(99)
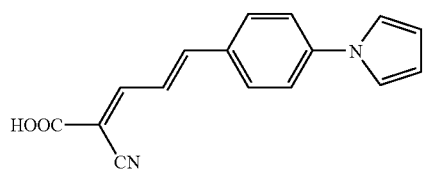
(100)
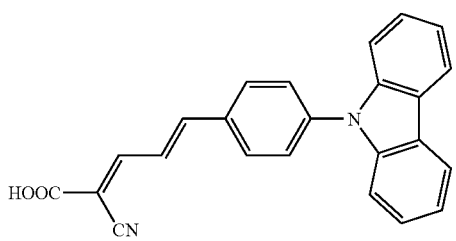
(101)
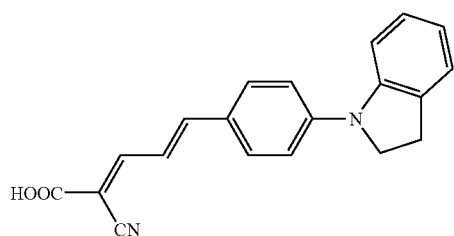
(102)
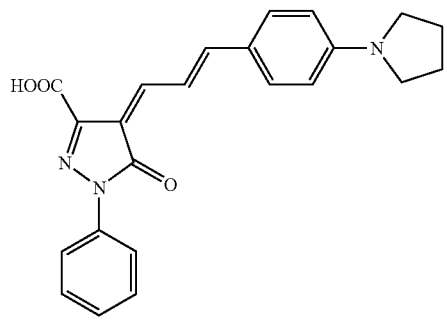
(103)
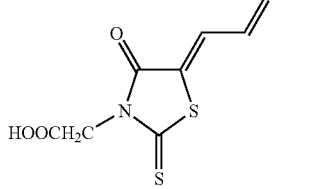
(104)
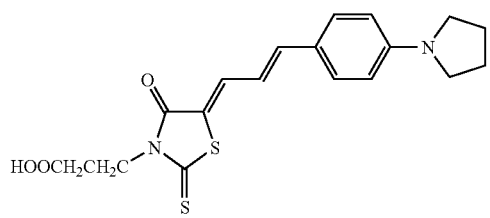
(105)
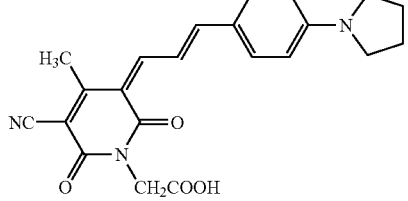
(106)
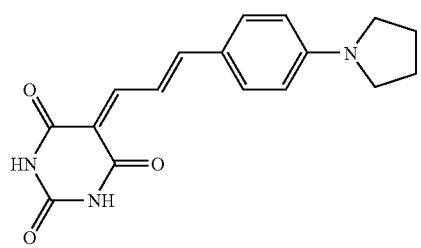
(107)
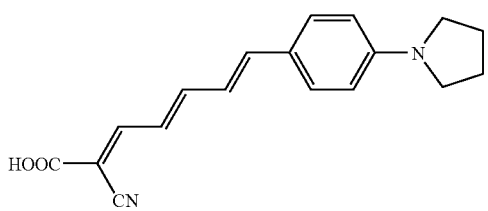
(108)
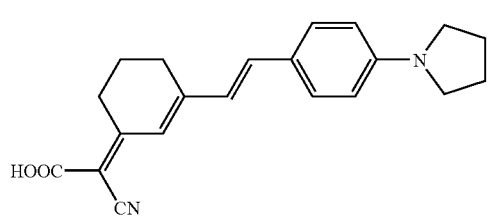
(109)
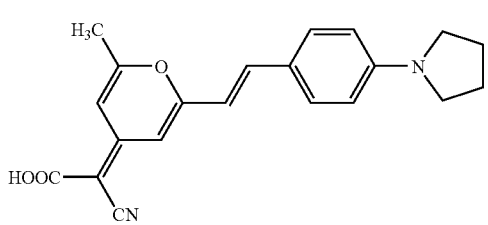
(110)

-continued
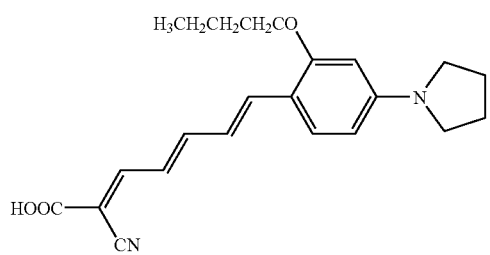
(111)
[KA 29]
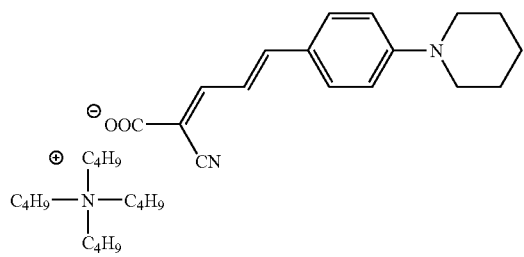
(112)
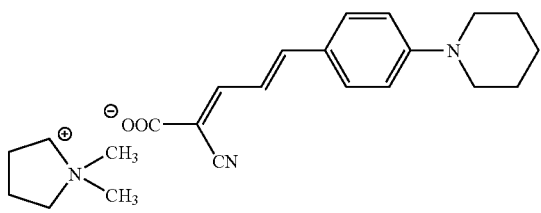
(113)
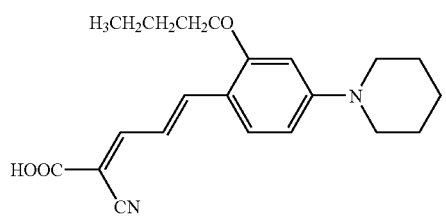
(114)
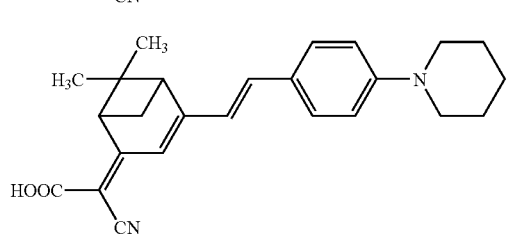
(115)
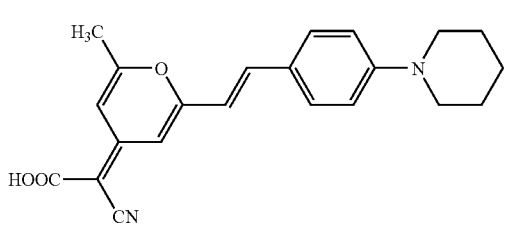
(116)
(117)
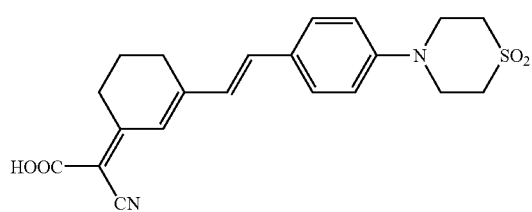
(118)
(119)
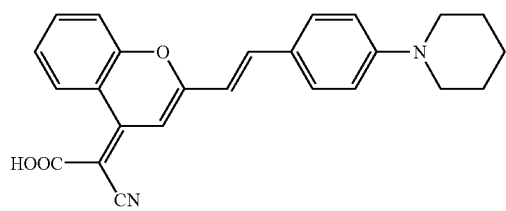
(120)
(121)
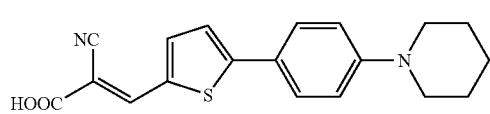
(122)
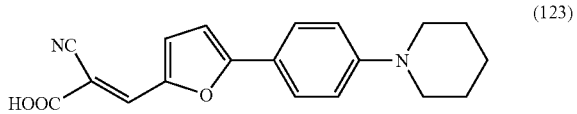
(123)

-continued
(124)
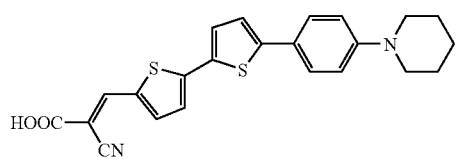
(125)
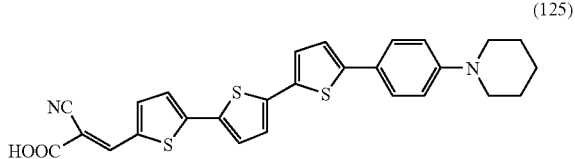
(126)
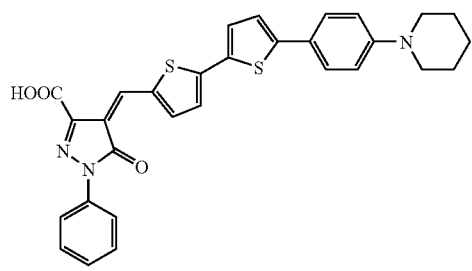
[KA 30]
(127)
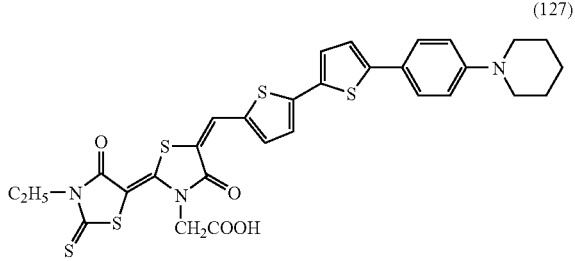
(128)
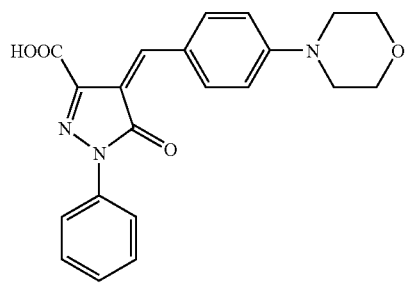
(129)
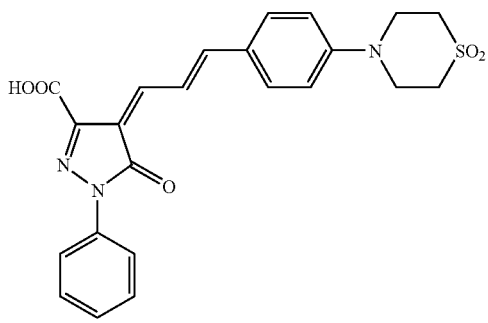
(130)
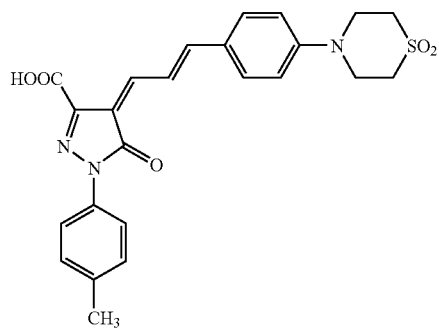
(131)
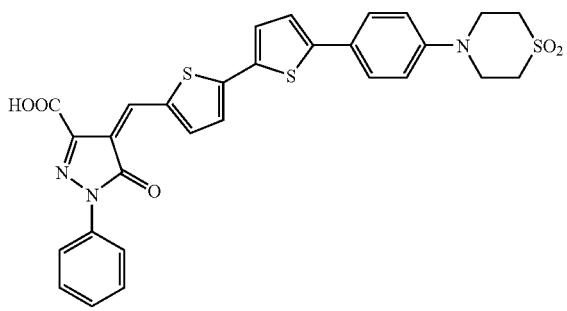
(132)
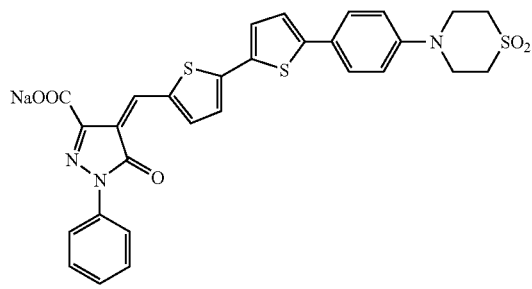
(133)
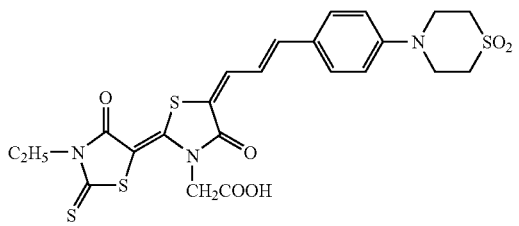

-continued
(134) 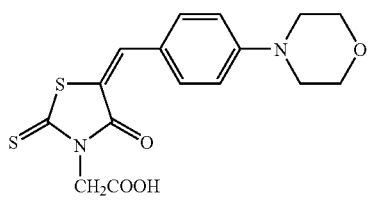
(135) 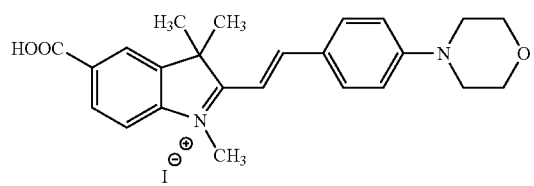
(136) 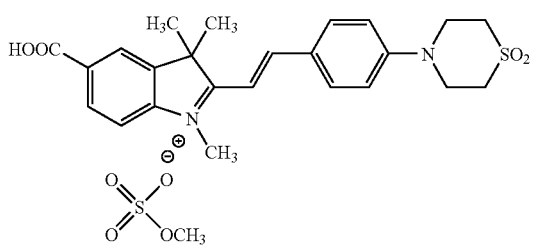
(137) 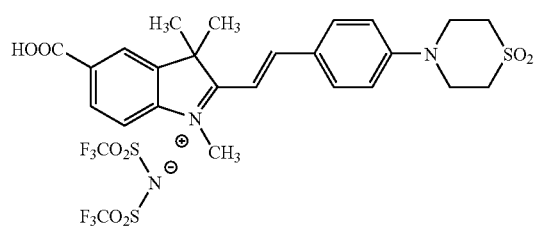
(138) 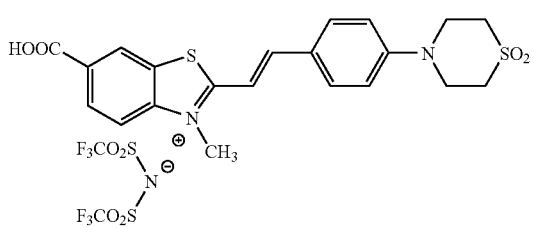
(139) 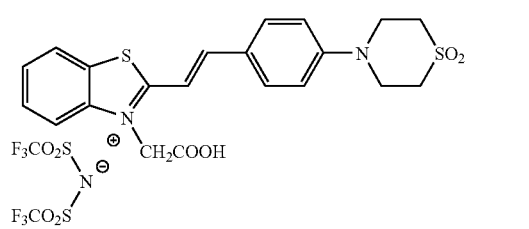
(140) 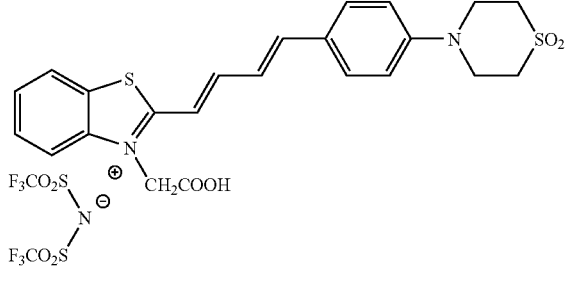
[KA 31]
(141) 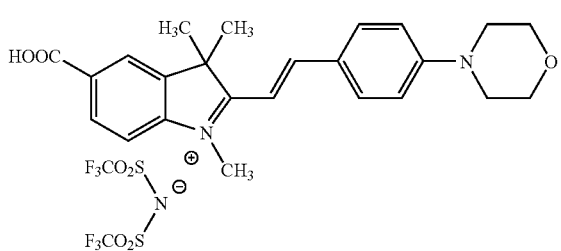
(142) 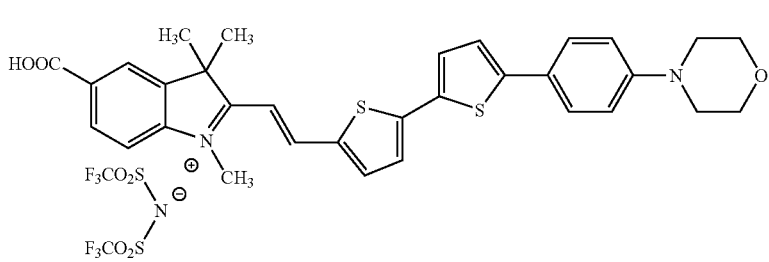

-continued
(143)
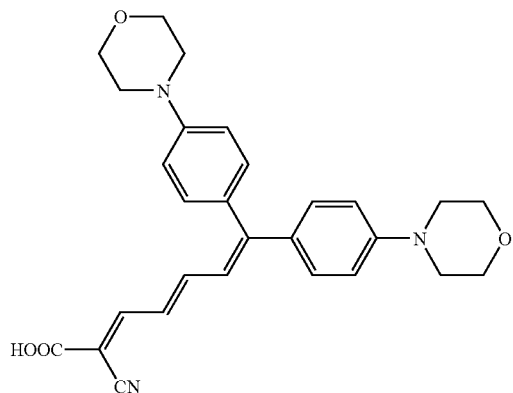
(144)
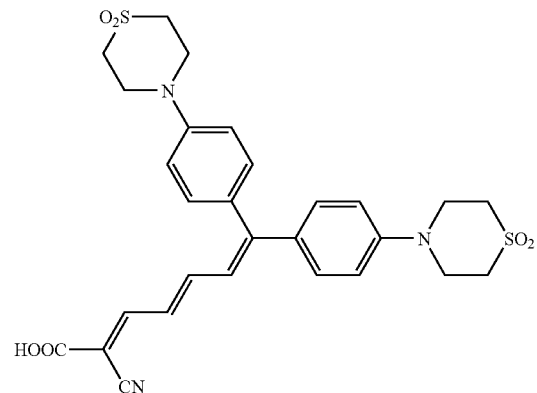
(145)
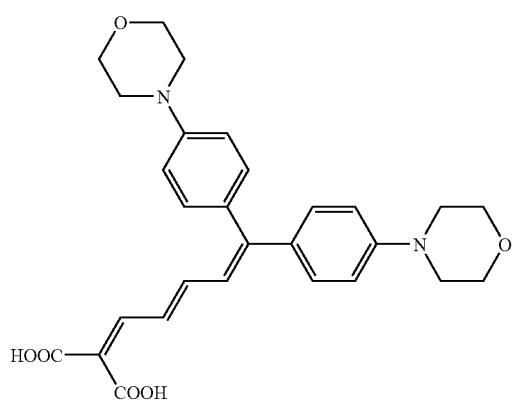
(146)
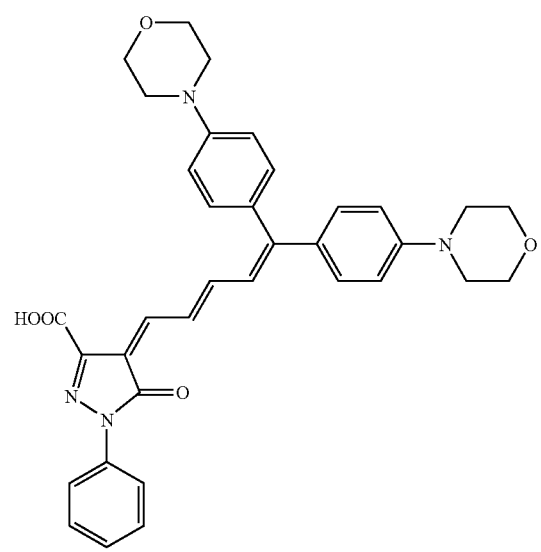
(147)
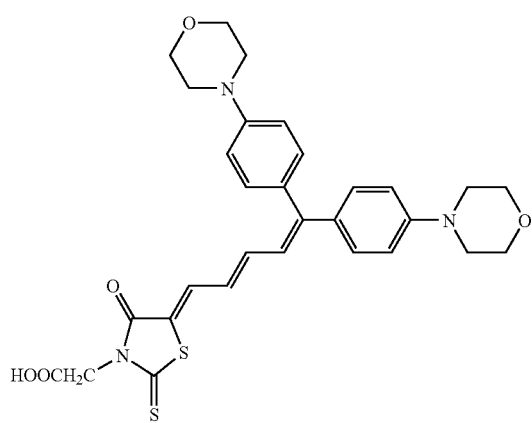
(148)
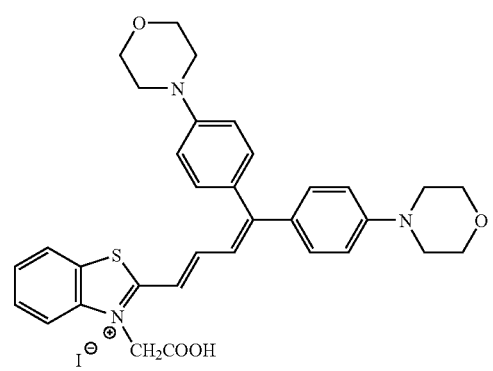

-continued
(149)
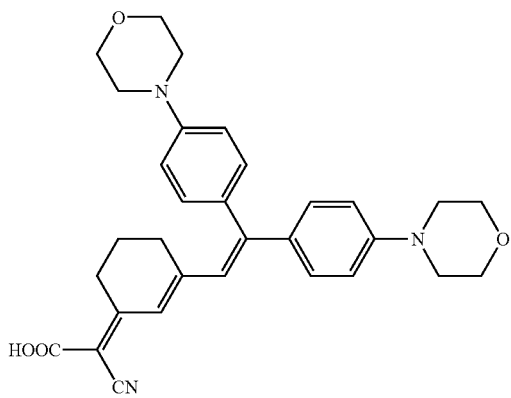
(150)
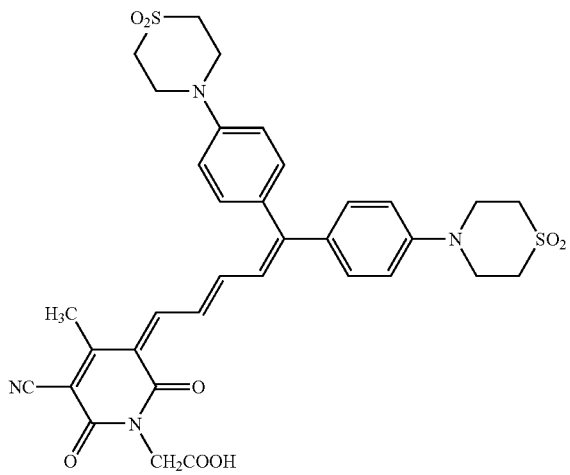
(151)
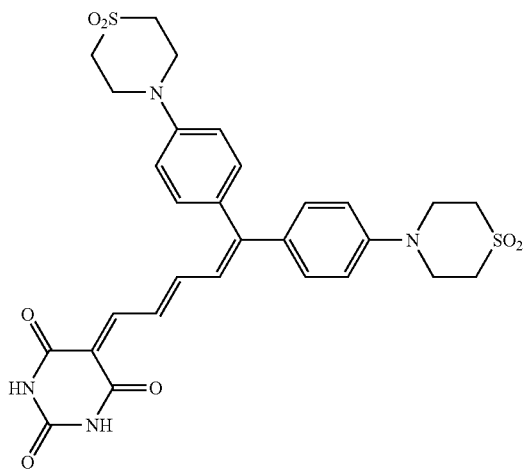
(152)
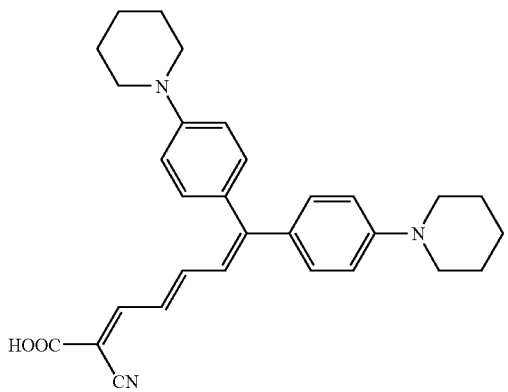
(153)
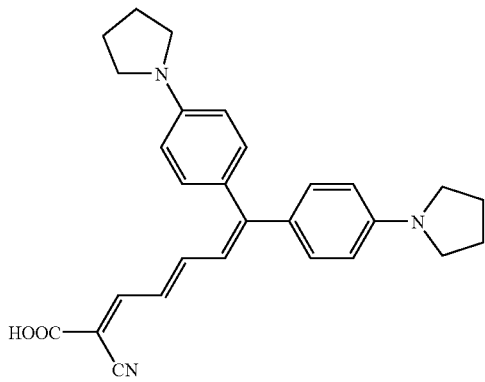
(154)
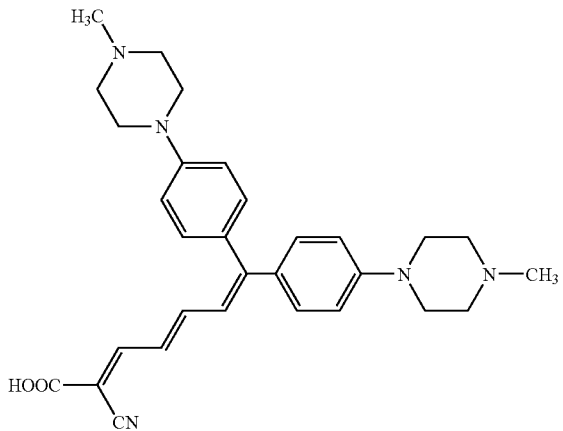
[KA 32]
(155)
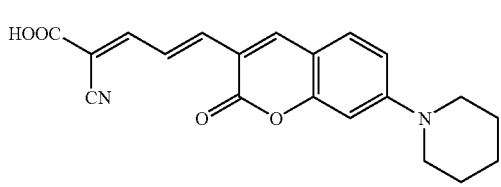
(156)
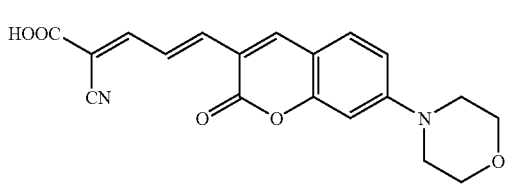

-continued
(157)
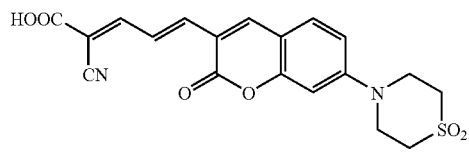
(158)
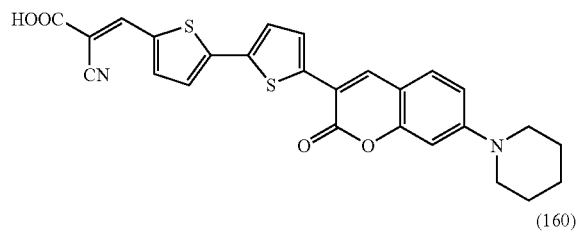
(159)
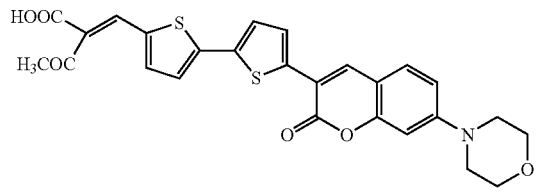
(160)
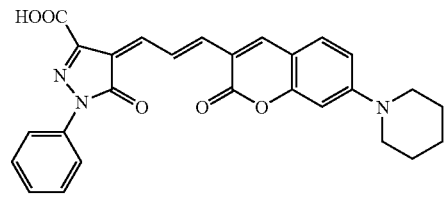
(161)
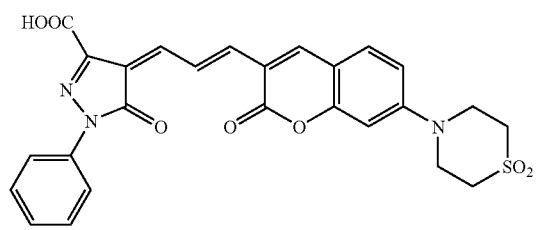
(162)
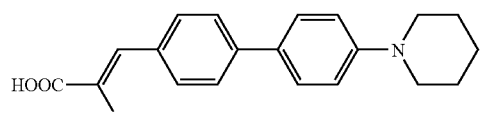
(163)
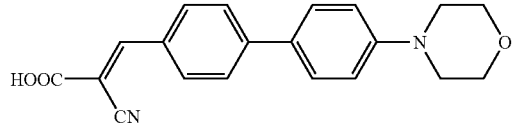
(164)
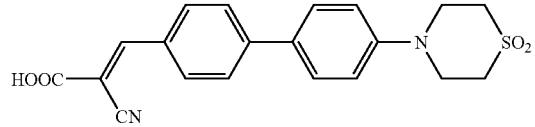
(165)
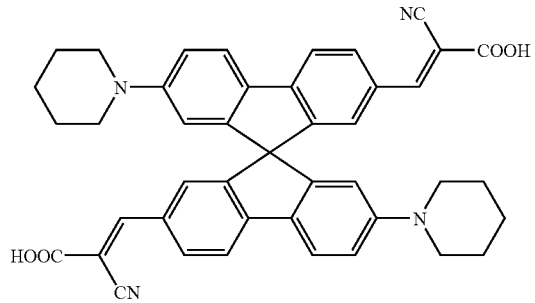
(166)
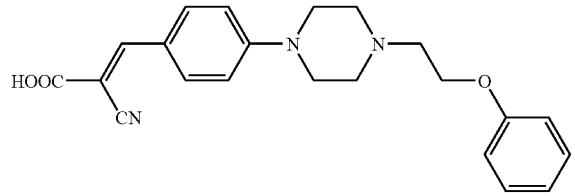
(167)
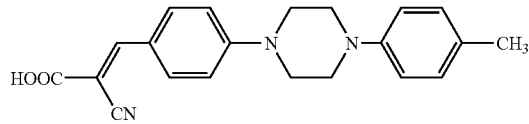
(168)
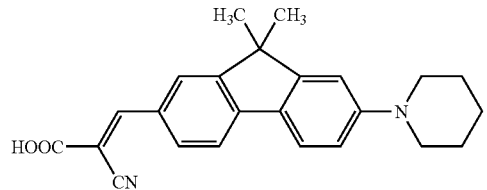
(169)
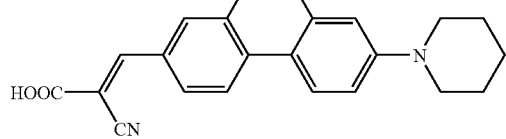
(170)
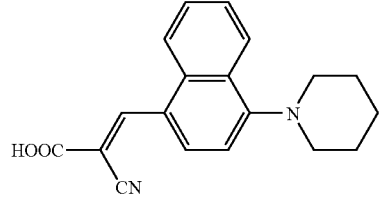

The dye-sensitized photoelectric conversion device of the present invention is the one, which is obtained, for example, by providing a thin film of oxide semiconductor fine particles on a substrate using oxide semiconductor fine particles, then supporting the methine based dye of the above formula (1) on the thin film.

In the present invention, the substrate, on which a thin film of oxide semiconductor fine particles is provided, has preferably an electrically conductive surface, and such substrate is easily available from the market. For example, such a substrate can be used that a thin film of an electrically conductive metal oxide such as tin oxide, etc. doped with indium, fluorine, antimony, etc., or a thin film of a metal such as copper, silver, gold, etc. is provided on the surface of a glass or a transparent polymer material such as polyethylene terephthalate, polyethersulfon, etc. Conductivity thereof may be generally 1,000Ω or less, and particularly preferably 100Ω or less.

In addition, specific examples of the metal oxide for the thin film of oxide semiconductor fine particles include oxides of titanium, tin, zinc, tungsten, zirconium, gallium, indium, yttrium, niobium, tantalum, vanadium, and the like. Among these oxides, an oxide of titanium, tin, zinc, niobium, indium, and the like are preferable, and titanium oxide, zinc oxide and tin oxide are particularly preferable. These oxide semiconductors can be used alone, but also used in combination. In addition, particle size of the oxide semiconductor fine particles is, in an average particle size, generally 1 to 500 nm, and preferably 1 to 100 nm. In addition, the oxide semiconductor fine particles can be used in combination or in a multilayer of those having a large particle size and those having a small particle size.

The thin film of oxide semiconductor fine particles can be manufactured by a method in which a thin film of the above oxide semiconductor fine particles is formed directly on a substrate such as the above polymer material by a method such as spraying, etc., a method in which a thin film of the semiconductor particles is electrically deposited using a substrate as an electrode, or a method in which a slurry of the semiconductor particles or a paste containing particles obtained by hydrolyzing precursor of the semiconductor particles such as semiconductor alkoxide, etc. is coated on a substrate followed by drying, curing or calcination, etc. Among them, in view of performance of the oxide semiconductor electrode, the method using a slurry is preferable. In the case of this method, the slurry to be used can be obtained by dispersing the oxide semiconductor fine particles, which are secondarily agglomerated, into a dispersing medium by a common method, so that an average primary particle size becomes 1 to 200 nm.

The dispersing medium for dispersing slurry is not particularly limited so long as the medium can disperse the semiconductor particles. For example, water, alcohols such as ethanol, etc., ketones such as acetone, acetylacetone, etc., or hydrocarbons such as hexane, etc. can be used, and these media may be used in combination. Use of water is preferable in view of reduced viscosity variation of the slurry. In addition, a dispersion stabilizer can be used to stabilize dispersed state of the oxide semiconductor fine particles. An example of the dispersing stabilizer to be used includes, for example, acids such as acetic acid, hydrochloric acid, nitric acid, etc., or acetylacetone, acrylic acid, polyethylene glycol, polyvinyl alcohol, etc.

The substrate coated with slurry may be calcined, and calcination temperature is generally 100° C. or higher, preferably 200° C. or higher, and the upper limit is basically the melting point (softening point) of substrate material or lower, generally 900° C., and preferably 600° C. or lower. In addition, calcination time is not particularly limited, but basically preferably within 4 hours. Thickness of the thin film on a substrate is generally 1 to 200 μm, and preferably 1 to 50 μm.

The thin film of oxide semiconductor fine particles may be subjected to secondary treatment. For example, performance of the thin film can be improved by dipping the whole substrate provided with the thin film directly into a solution of alkoxide, chloride, nitrate, sulfide or the like of the same metal to that of the metal oxide semiconductor, followed by drying or calcination again. Example of the metal alkoxide to be used includes titanium ethoxide, titanium isopropoxide, titanium t-butoxide, n-dibutyl-diacetyl tin, etc., and alcohol solutions thereof are used. In addition, the chloride includes, for example, titanium tetrachloride, tin tetrachloride, zinc chloride, etc., and aqueous solutions thereof are used. In the thus obtained thin film of oxide semiconductor subjected to secondary treatment, the state of particles of the oxide semiconductor is maintained.

Next, method of supporting the methine based dye of the present invention on the thin film of oxide semiconductor will be explained.

The method of supporting the methine based dye to be used in the present invention represented by the above formula (1) or the like includes a method in which a substrate provided with the above thin film of oxide semiconductor is dipped into a solution obtained by dissolving the methine based dye of the formula (1) or the like in a solvent which can dissolve said dye, or a dispersion liquid obtained by dispersing the methine based dye which has poor solubility. Concentration of the dye in the solution or the dispersion liquid may be determined as appropriate depending on a type of the methine based dye of the formula (1) or the like. Temperature of the dye solution or dispersion liquid in dipping is basically from ordinary temperature to the boiling point of the solvent to be used for dissolving the dye, and dipping time is from 1 minute to around 48 hours. Specific example of the solvent which can be used for dissolving the methine based dye of the formula (1) or the like includes, for example, methanol, ethanol, acetonitrile, dimethylsulfoxide, dimethylformamide, acetone, t-butanol, etc. Concentration of the dye in the solution is generally $1\times10^{-6}$ M to 1 M, and preferably $1\times10^{-5}$ M to $1\times10^{-1}$ M. In such way, the photoelectric conversion device of the present invention having the thin film of oxide semiconductor fine particles sensitized with the methine based dye of the formula (1) or the like can be obtained.

The methine based dye of the above formula (1) or the like to be supported may be one type or several types in mixture. Alternatively, the methine based dye of the formula (1) or the like to be used in the present invention and another metal complex dye or an organic dye may be used in mixture. In particular, by using a plural number of dyes having different absorption wavelengths from each other in combination, a wide range of absorption wavelength can be utilized, and a solar battery having high photoelectric conversion efficiency can be obtained. An example of the metal complex dye to be used in combination is not particularly limited, but includes ruthenium complex and quaternary salt thereof shown in Non-Patent Literature 2, phthalocyanine, porphyrin, etc., and an example of the organic dye to be used in combination includes phthalocyanine containing no metal, porphyrin, cyanine, methine based dye such as merocyanine, oxonol, triphenylmethane based dye, acrylic acid based dye shown in Patent Literature 2, etc., xanthene based dye, azo based dye, anthraquinone based dye, perylene based dye, etc. Preferable one includes ruthenium complex, or methine based dye such as merocyanine based dye, acrylic acid based dye, etc. When 2 or more types of dyes are used, each dye may be adsorbed sequentially on the thin film of semiconductor or adsorbed simultaneously using a solution containing plural types of dyes, etc.

Ratio of dyes to be mixed is not particularly limited, and determined as appropriate for each dye. Generally equimolar dyes are mixed, and preferably around 10 mole % or more is used for each dye. When dye is supported on the oxide semiconductor fine particles by using a solution or a dispersion liquid containing 2 types of dyes, total concentration of dyes in the solution or dispersion liquid may be same as in the case of supporting only one type of dye described above. As a solvent when mixed dyes are used, the same solvents described above can be used, and the solvent for each dye to be used may be same or different from each other.

When dye is supported on the thin film of oxide semiconductor fine particles, in order to prevent association of dye, it is effective to support dye in the presence of an inclusion compound. Here, inclusion compound includes steroid-type compounds such as cholic acid, etc., crown ether, cyclodextrin, calixarene, polyethylene oxide, etc., and preferably cholic acid and its affinity such as deoxycholic acid, dehydrodeoxycholic acid, chenodeoxycholic acid, methyl cholate ester, sodium cholate, etc., polyethylene oxide, etc. In addition, after dye is supported, the surface of semiconductor thin film may be treated with an amine compound such as 4-t-butylpyridine, etc. As for method of the treatment, for example, a method in which a substrate provided with the thin film of semiconductor particles supported with a dye is dipped into an ethanol solution of an amine compound, or the like is employed.

The solar battery of the present invention is composed of the photoelectric conversion device obtained by supporting the methine based dye of the above formula (1) or the like, on the above thin film of oxide semiconductor as an electrode, a counter electrode, a redox electrolyte, a hole transporting material, a p-type semiconductor, etc. Forms of redox electrolyte, hole transporting material, p-type semiconductor, etc. include liquid, coagulated body (gel or gel-like), solid, etc. Liquid component includes those in which redox electrolyte, molten salt, hole transporting material, p-type semiconductor, etc. are each dissolved in a solvent or an ambient temperature molten salt, and coagulated body (gel or gel-like) includes those in which these components are impregnated in a polymer matrix or a low molecular gelling agent, etc, respectively. Solid component includes redox electrolyte, molten salt which melts on heating, hole transporting material, p-type semiconductor, etc. which are used as they are. The hole transporting material includes amine derivative, conductive polymer such as polyacetylene, polyaniline, polythiophen, etc., those using a discotic-type liquid crystal phase such as triphenylene type compound, etc. In addition, the p-type semiconductor includes CuI, CuSCN, etc. As the counter electrode, those having electric conductivity and working catalytically on the reduction reaction of the redox electrolyte are preferable. For example, a glass or a polymer film deposited with platinum, carbon, rhodium, ruthenium, etc., and also coated with conductive particles, or the like can be used.

An example of the redox electrolyte to be used for the solar battery of the present invention includes halogen redox electrolyte composed of a halogen compound having halogen ion as a counter ion and a halogen molecule; metal redox electrolyte such as a ferrocyanide salt-ferricyanide salt, a ferrocene-ferricinium ion, metal complex such as cobalt complex, etc.; organic redox electrolyte such as an alkylthiol-alkyldisulfide, viologen dye, a hydroquinone-quinone, etc.; and the like, and halogen redox electrolyte is preferable. The halogen molecule in the halogen redox electrolyte composed of a halogen compound and a halogen molecule includes, for example, iodine molecule, bromine molecule, and iodine molecule is preferable. In addition, the halogen compound having halogen ion as a counter ion includes, for example, metal halide such as LiBr, NaBr, KBr, LiI, NaI, KI, CsI, $CaI_2$, $MgI_2$, CuI, etc.; or organic quaternary ammonium halide such as tetraalkylammonium iodide, imidazolium iodide, pyridinium iodide, etc. or the like, and salts having iodide ion as a counter ion are preferable. In addition, besides the above iodide ion, an electrolyte having an imide ion such as bis(trifluoromethanesulfonyl)imide ion, dicyanoimido ion, etc. as a counter ion is also preferably used.

In addition, when the redox electrolyte is constituted in a form of solution containing the electrolyte, an electrochemically inactive solvent is used as a solvent of the solution. Such solvent includes, for example, acetonitrile, propylene carbonate, ethylene carbonate, 3-methoxypropionitrile, methoxyacetonitrile, ethylene glycol, propylene glycol, diethylene glycol, triethylene glycol, γ-butyrolactone, dimethoxyethane, diethyl carbonate, diethyl ether, diethyl carbonate, dimethyl carbonate, 1,2-dimethoxyethane, dimethylformamide, dimethylsulfoxide, 1,3-dioxoran, methyl formate, 2-methyltetrahydrofuran, 3-methyl-oxazolidine-2-one, sulfolane, tetrahydrofuran, water, etc. Among them, acetonitrile, propylene carbonate, ethylene carbonate, 3-methoxypropionitrile, methoxyacetonitrile, ethylene glycol, 3-methyl-oxazolidine-2-one, γ-butyrolactone, etc. are particularly preferable. These solvents may be used alone or in combination of 2 or more types. The gel-like electrolyte includes a matrix such as oligomer, polymer, etc. which contains an electrolyte or an electrolyte solution, a low molecular gelling agent described in Non-Patent Literature 3, etc. which similarly contains an electrolyte or an electrolyte solution, and the like. Concentration of the redox electrolyte is generally 0.01 to 99% by weight, and preferably 0.1 to 90% by weight.

The solar battery of the present invention can be obtained by arranging an electrode of the photoelectric conversion device in which a dye is supported on the thin film of oxide semiconductor on a substrate and counter electrodes in such a way that the counter electrodes sandwich the device, and filling a solution containing a redox electrolyte in between.

EXAMPLES

Hereinafter, the present invention will be explained in detail based on Examples, however, the present invention should not be limited to these Examples. In these Examples, the term of "part(s)" represents "part(s) by mass" unless otherwise noted. In addition, compound number means the compound number in the aforementioned specific examples. Furthermore, the maximum absorption wavelength and the NMR were measured by using UV-3150 spectrophotometer (manufactured by Shimadzu Corp.) and Gemini 300 (manufactured by Varian, Inc.), respectively.

Example 1

Methyl cyanoacetate (1 part) and the following compound (318) (2 parts) were dissolved in ethanol (20 parts). Piperidine (0.01 parts) was added into this solution, then this solution was heated to reflux for 2 hours. After the reaction, the solution was cooled to deposit crystal, which was separated and purified by column chromatography followed by recrystallization with ethanol, to obtain orange crystal (2.1 parts). The orange crystal was refluxed in ethanol (20 parts) in the presence of potassium hydroxide (1 part) for 2 hours. Water (50 parts) was added into the reaction solution, then the reaction solution was neutralized with hydrochloric acid, and deposited orange crystal was filtered, washed with water, then recrystallized from ethanol, to obtain the compound of compound number (32a) (1.2 parts) as brownish orange crystal.

[KA 33]

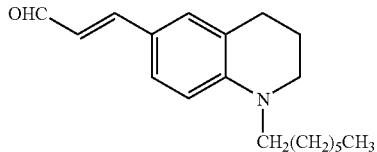
(318)

Measured values of this compound for the maximum absorption wavelength and NMR were as follows.

Maximum absorption wavelength: $\lambda_{max}$=448 nm (water: acetonitrile=7:3);

Measured values of NMR: 1H-NMR (PPM: d6-DMSO): 0.85 (m, 3H), 1.27 (m, 10H), 1.53 (m, 2H), 1.84 (m, 2H), 2.73 (m, 2H), 3.35 (m, 4H), 6.60 (d, 1H), 6.81 (m, 1H), 7.25 (m, 3H), 7.82 (d, 1H).

Example 2

The same procedures were repeated as in Example 1 except that the above compound (318) (2 parts) was replaced with the following compound (319) (2 parts), to obtain the compound of compound number (278) (1.4 parts) as brownish orange crystal.

[KA 34]

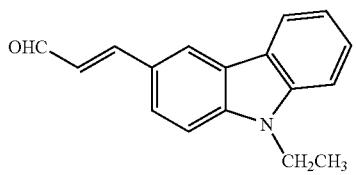
(319)

Measured values of this compound for the maximum absorption wavelength and NMR were as follows.

Maximum absorption wavelength: $\lambda_{max}$=395 nm (water: acetonitrile=7:3);

Measured values of NMR: 1H-NMR (PPM: d6-DMSO): 1.34 (t, 3H), 4.50 (m, 2H), 7.28 (m, 2H), 7.52 (m, 1H), 7.69 (t, 2H), 7.84 (m, 2H), 8.14 (d, 1H), 8.31 (d, 1H), 8.62 (d, 1H).

Examples 3 to 9

The methine based dyes of the compound numbers shown in Table 7 were each dissolved in Ethanol (EtOH) so that concentration thereof became $3.2 \times 10^{-4}$ M. A porous substrate (a semiconductor thin film electrode obtained by sintering porous titanium oxide at 450° C. for 30 minutes on a transparent conductive glass electrode) was dipped into the solution at room temperature (20° C.) for 12 hours to support each dye, then washed with a solvent (ethanol) and dried, to obtain a photoelectric conversion device of the present invention comprising a dye-sensitized semiconductor thin film. In Example 8 and Example 9, a photoelectric conversion device was similarly obtained by supporting 2 types of dyes by preparing an EtOH solution using 2 types of dyes (a methine based dye of the present invention and a compound of the following formula (320) which was a photo-sensitizing metal complex dye described in Non-Patent Literature 2 or a compound of the following formula (321) which was a photo-sensitizing organic dye described in Patent Literature 2 were used in combination, respectively) so that concentration of each dye became $1.6 \times 10^{-4}$ M. Also, in Examples 4 to 9, dyes were similarly supported using a titanium tetrachloride-treated semiconductor thin film electrode obtained by adding drop-wise 0.2 M titanium tetrachloride aqueous solution (about 1 cc) on a titanium oxide thin film section (about 0.25 cm²) of the semiconductor thin film electrode, allowing to stand at room temperature for 24 hours, washing with water, and calcination again at 450° C. for 30 minutes. In addition, in Example 5 and Example 7, a cholic acid-treated dye-sensitized semiconductor thin film was obtained by preparing a dye solution in the dye supporting by adding cholic acid (manufactured by Tokyo Chem. Ind. Co. Ltd.) represented by the following formula (322) as an inclusion compound so that concentration thereof became $3 \times 10^{-2}$ M, and supporting on the semiconductor thin film. On a substrate provided with the thus obtained dye-sensitized semiconductor thin film, a conductive glass sputtered with platinum was fixed leaving a space of 20 μm in such way that a sputtered surface of the conductive glass was opposed to the semiconductor thin film, and a solution containing an electrolyte was filled into the space. As the electrolytic solution, a solution in which iodine/lithium iodide/1,2-dimethyl-3-n-propylimidazolium iodide/t-butylpyridine were dissolved in 3-methoxypropionitrile in concentrations of 0.1 M/0.1 M/0.6 M/1 M, respectively, was used.

Size of the battery to be measured was 0.25 cm² in effective area. As a light source, 500 W xenon lamp was used to obtain an intensity of 100 mW/cm² through the AM (air mass passed through in atmosphere) 1.5 filter. Short-circuit current, open-circuit voltage and conversion efficiency were measured using Solar Simulator WXS-155S-10, AM 1.5 G (manufactured by Wacom Electric Co., Ltd.).

[KA 35]

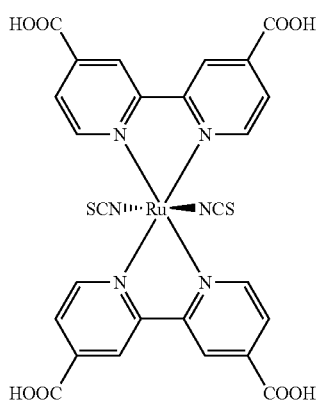
(320)

-continued (321)

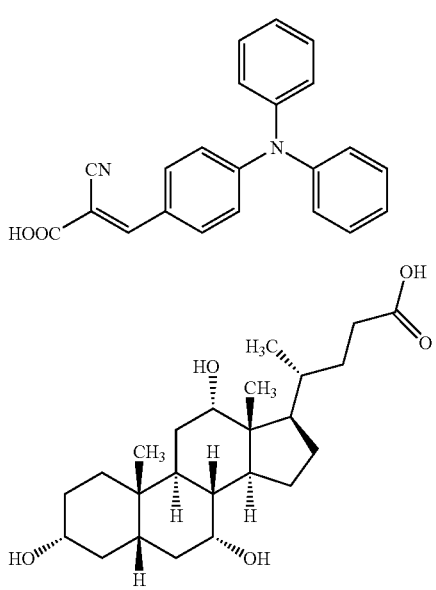

(322)

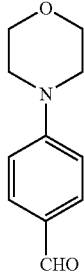

[KA 36]

(171)

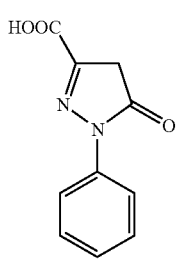

Measured values of this compound (6) for the maximum absorption wavelength and NMR were as follows.

Maximum absorption wavelength: $\lambda_{max}=354$ nm (in ethanol);

Measured values of NMR: 1H-NMR (PPM: d6-DMSO): 3.40 (t, 4H), 3.75 (t, 4H), 7.08 (d, 2H), 7.97 (d, 2H), 8.12 (s, 1H).

TABLE 7

| Example | Compound No. | Short-circuit current (mA/cm$^2$) | Open-circuit Voltage (V) | Conversion efficiency (%) | TiCl$_4$ treatment on thin film | Cholic acid |
|---|---|---|---|---|---|---|
| 3 | 32a | 10.7 | 0.72 | 5.4 | No | No |
| 4 | 32a | 12.8 | 0.71 | 6.3 | Yes | No |
| 5 | 32a | 12.6 | 0.73 | 6.4 | Yes | Yes |
| 6 | 278 | 12.1 | 0.69 | 5.8 | Yes | No |
| 7 | 278 | 15.2 | 0.62 | 6.6 | Yes | Yes |
| 8 | 32a + 320 | 17.2 | 0.61 | 7.2 | Yes | No |
| 9 | 32a + 321 | 15.9 | 0.61 | 6.8 | Yes | No |

From the results of Table 7, it can be understood that by using the photoelectric conversion device sensitized with the methine based dye of the present invention represented by the formula (1), visible light can be efficiently converted to electricity. Also, by using the dye of the present invention in combination with the known compound as a sensitizing dye, a further improvement in conversion efficiency was found.

Next, the present invention will be further explained in detail based on Examples using the compound of the formula (1b), however, the present invention should not be limited to these Examples.

Example 1A

Methyl cyanoacetate (1 part) and the following compound (171) (1.6 parts) were dissolved in ethanol (20 parts). Piperidine (0.01 parts) was added into this solution, then this solution was heated to reflux for 2 hours. After the reaction, the solution was cooled to deposit crystal, which was separated and purified by column chromatography followed by recrystallization from ethanol, to obtain yellow crystal (2.1 parts). The orange color crystal was refluxed in ethanol (20 parts) in the presence of potassium hydroxide (1 part) for 2 hours. Water (50 parts) was added into the reaction solution, further the reaction solution was neutralized with hydrochloric acid, and deposited yellow crystal was filtered, washed with water, then recrystallized from ethanol, to obtain the compound of compound number (6) (1.2 parts) as yellow crystal.

Example 2A

The above compound (171) (1 part) and the following compound (172) (1 part) were heated to reflux in ethanol (20 parts), for 2 hours, then cooled. Resultant crystal was recrystallized from ethanol to obtain the compound (128) (1.2 parts) as vermilion crystal.

[KA 37]

(172)

Measured values of this compound (128) for the maximum absorption wavelength and NMR were as follows.

Maximum absorption wavelength: $\lambda_{max}$=473 nm (water: acetonitrile=7:3);

Measured values of NMR: 1H-NMR (PPM: d6-DMSO): 3.57 (t, 4H), 3.77 (t, 4H), 7.10 (s, 2H), 7.28 (t, 1H), 7.48 (t, 2H), 7.93 (d, 2H), 8.52 (s, 1H), 8.63 (d, 2H).

Example 3A

The same procedures were repeated as in Example 2A except that the above compound (172) (1 part) was replaced with the following compound (173) (0.6 parts), to obtain the compound of compound number (135) (1.1 parts) as purple crystal.

[KA 38]

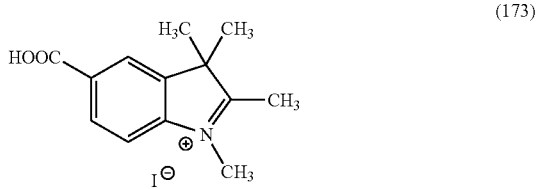

(173)

Measured values of this compound (135) for the maximum absorption wavelength and NMR were as follows.

Maximum absorption wavelength: $\lambda_{max}$=552 nm (in ethanol);

Measured values of NMR: 1H-NMR (PPM: d6-DMSO): 1.80 (s, 6H), 3.55 (t, 4H), 3.75 (t, 4H), 4.00 (s, 3H), 7.14 (d, 2H), 7.36 (d, 1H), 7.82 (d, 1H), 8.14 (m, 3H), 8.34 (s, 1H), 8.42 (d, 1H).

Example 4A

The same procedures were repeated as in Example 2A except that the above compound (172) (1 part) was replaced with the following compound (174) (0.6 parts), to obtain the compound of compound number (134) (1.1 parts) as vermillion crystal.

[KA 39]

(174)

Measured value of this compound (134) for the maximum absorption wavelength was as follows.

Maximum absorption wavelength: $\lambda_{max}$=440 nm (in ethanol).

Example 5A

The methine based dye of compound number 128 of the present invention was dissolved in Ethanol (EtOH) so that concentration became $3.2 \times 10^{-4}$ M. A porous substrate (a titanium tetrachloride-treated semiconductor thin film electrode obtained by adding drop-wise 0.2 M titanium tetrachloride aqueous solution (about 1 cc) on a thin film section (about 0.25 cm$^2$) of the semiconductor, which was obtained by sintering porous titanium oxide at 450° C. for 30 minutes, on a transparent conductive glass electrode, allowing to stand at room temperature (20° C.) for 24 hours, washing with water, and calcination again at 450° C. for 30 minutes) was dipped into the solution at room temperature (20° C.) for 12 hours to support each dye, then washed with a solvent (ethanol) and dried, to obtain a photoelectric conversion device of the present invention comprising a thin film of semiconductor particles sensitized with dye. On a substrate provided with the thus obtained thin film of dye-sensitized semiconductor particles, a conductive glass sputtered with platinum was fixed leaving a space of 20 um in such a way that a sputtered surface of the conductive glass was opposed to the semiconductor thin film, and a solution containing an electrolyte (electrolytic solution) was filled into the space. As the electrolytic solution, a solution in which iodine/lithium iodide/1,2-dimethyl-3-n-propylimidazolium iodide/t-butylpyridine were dissolved in 3-methoxypropionitrile in concentrations of 0.1 M/0.1 M/0.6 M/1 M, respectively, was used.

Size of the battery to be measured was 0.25 cm$^2$ in effective area. As a light source, 500 W xenon lamp was used to obtain an intensity of 100 mW/cm$^2$ through the AM (atmosphere passage air mass) 1.5 filter. Short-circuit current, open-circuit voltage and conversion efficiency were measured using Solar Simulator WXS-155S-10, AM 1.5 G (manufactured by Wacom Electric Co., Ltd.).

As a result, short-circuit current of 12.1 mA/cm$^2$, open-circuit voltage of 0.67 V, and conversion efficiency of 5.5% were obtained.

From the above results, it can be understood that the photoelectric conversion device sensitized with the methine based dye of the formula (1) of the present invention can convert visible light to electricity effectively. In addition, it was also proved that conversion efficiency can be further improved by using the methine based dye of the present invention in combination with another dye.

INDUSTRIAL APPLICABILITY

Since the present invention enables manufacturing of a dye-sensitized photoelectric conversion device having high photoelectric conversion efficiency at low cost, the present invention provides a possibility to manufacture a solar battery having high photoelectric conversion efficiency at low cost, and is therefore industrially very useful.

The invention claimed is:

1. A photoelectric conversion device comprising oxide semiconductor fine particles sensitized with a methine based dye represented by the following formula (1a):

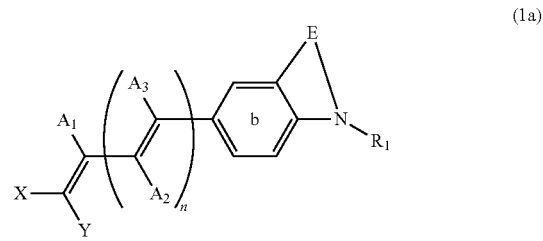

(1a)

in the formula (1a), n represents an integer of 0 to 7; $R_1$ represents an optionally substituted aromatic residue, an optionally substituted aliphatic hydrocarbon residue or an acyl group; the group composed of the benzene ring "b", N—$R_1$ and substituent E is an N—$R_1$-substituted tetrahydroquinoline-6-yl group; X represents a carboxyl group; Y represents a cyano group; $A_1$, $A_2$ and $A_3$ are each a hydrogen atom, or $A_1$ and $A_3$ or neighboring $A_2$s or neighboring $A_3$s combine together to form a linker having 2 to 3 carbon atoms or a linker composed of an aliphatic chain having 2 carbon atoms and an oxygen atom, which forms a 5- to 6-membered ring that may optionally be substituted with a methyl group, and the remaining $A_1$, $A_2$ and $A_3$ are each a hydrogen atom; the benzene ring "b" may have 1 to 3 substituents selected from the group consisting of a halogen atom, an amide group, a hydroxyl group, a cyano group, a nitro group, an alkoxyl group, an acyl group, a substituted or unsubstituted amino group, an optionally substituted aliphatic hydrocarbon residue and an optionally substituted aromatic residue; when a plural number of substituents exist, these substituents may combine with each other similarly as described above to form an optionally substituted ring.

2. The photoelectric conversion device according to claim 1, wherein n is 0 to 6.

3. The photoelectric conversion device according to claim 1, wherein $R_1$ is an optionally substituted aliphatic hydrocarbon residue.

4. The photoelectric conversion device according to claim 3, wherein the optionally substituted aliphatic hydrocarbon residue is an optionally substituted aliphatic hydrocarbon residue having 5 to 36 carbon atoms.

5. The photoelectric conversion device according to claim 1, wherein $R_1$ is an optionally substituted aromatic hydrocarbon residue.

6. The photoelectric conversion device according to claim 5, wherein the optionally substituted aromatic hydrocarbon residue is an aromatic hydrocarbon residue having a substituent of an optionally substituted aliphatic hydrocarbon residue having 1 to 36 carbon atoms.

7. A photoelectric conversion device comprising oxide semiconductor fine particles sensitized with a methine based dye represented by the formula (1a) according to claim 1 and a metal complex and/or an organic dye having a structure other than the formula (1a).

8. The photoelectric conversion device according to claim 1, wherein the oxide semiconductor fine particles are those containing titanium dioxide, zinc oxide or tin oxide.

9. The photoelectric conversion device according to claim 1, wherein the oxide semiconductor fine particles are those sensitized by supporting a methine based dye represented by the formula (1a) in the presence of an inclusion compound.

10. The photoelectric conversion device according to claim 1, wherein the oxide semiconductor fine particles are those sensitized by supporting of the methine based dye represented by the formula (1a) on a thin film of oxide semiconductor fine particles.

11. A photoelectric conversion device, wherein the methine based dye represented by the formula (1a) according to claim 1 is supported on a semiconductor thin film of an oxide semiconductor thin film electrode.

12. The photoelectric conversion device according to claim 1, wherein Y is a cyano group; and $R_1$ is an optionally substituted, saturated or unsaturated, linear or branched alkyl group having 1 to 18 carbon atoms.

* * * * *